US011333977B2

(12) United States Patent
Ishiji et al.

(10) Patent No.: US 11,333,977 B2
(45) Date of Patent: May 17, 2022

(54) CURABLE COMPOSITION, LITHOGRAPHIC PRINTING PLATE PRECURSOR, METHOD FOR PRODUCING LITHOGRAPHIC PRINTING PLATE, AND COMPOUND

(71) Applicant: FUJIFILM Corporation, Tokyo (JP)

(72) Inventors: Yohei Ishiji, Shizuoka (JP); Keisuke Nogoshi, Shizuoka (JP); Kazuaki Enomoto, Shizuoka (JP); Yuuya Miyagawa, Shizuoka (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 16/540,338

(22) Filed: Aug. 14, 2019

(65) Prior Publication Data
US 2019/0369495 A1    Dec. 5, 2019

Related U.S. Application Data

(63) Continuation of application No. PCT/JP2018/007359, filed on Feb. 27, 2018.

(30) Foreign Application Priority Data

Feb. 28, 2017 (JP) .............. JP2017-037779
Sep. 29, 2017 (JP) .............. JP2017-191496
Dec. 27, 2017 (JP) .............. JP2017-252560

(51) Int. Cl.
| | | |
|---|---|---|
| *G03F 7/031* | (2006.01) | |
| *B41N 1/14* | (2006.01) | |
| *C07C 311/48* | (2006.01) | |
| *B41C 1/10* | (2006.01) | |
| *G03F 7/20* | (2006.01) | |
| *G03F 7/32* | (2006.01) | |

(52) U.S. Cl.
CPC ............ *G03F 7/031* (2013.01); *B41C 1/1008* (2013.01); *B41N 1/14* (2013.01); *C07C 311/48* (2013.01); *G03F 7/2006* (2013.01); *G03F 7/325* (2013.01); *G03F 7/327* (2013.01)

(58) Field of Classification Search
CPC ............................................. G03F 7/32
See application file for complete search history.

(56) References Cited

U.S. PATENT DOCUMENTS

| | | | | |
|---|---|---|---|---|
| 2002/0025489 A1* | 2/2002 | Shimada | ............... | B41C 1/1008 430/270.1 |
| 2004/0067435 A1* | 4/2004 | Iwato | ............... | B41C 1/1008 430/270.1 |
| 2005/0059835 A1* | 3/2005 | Wassmann-Wilken | ...... | C07F 7/1804 556/437 |
| 2005/0202343 A1* | 9/2005 | Fujimaki | ............... | B41C 1/1008 430/270.1 |
| 2007/0160815 A1* | 7/2007 | Tsuchimura | ......... | C09D 11/101 428/195.1 |
| 2007/0275322 A1 | 11/2007 | Tao et al. | | |
| 2008/0096132 A1* | 4/2008 | Araki | .................... | B41C 1/1016 430/286.1 |
| 2008/0241740 A1* | 10/2008 | Oohashi | ................... | B41N 3/00 430/270.1 |
| 2009/0233221 A1* | 9/2009 | Kanchiku | ............. | B41C 1/1016 430/270.1 |

FOREIGN PATENT DOCUMENTS

| | | | |
|---|---|---|---|
| EP | 1 808 466 A1 | 7/2007 | |
| JP | 2006-241406 A | 9/2006 | |
| JP | 2007-238777 A | 9/2007 | |
| JP | 2009-538446 A | 11/2009 | |
| JP | 2015-96598 A | 5/2015 | |
| JP | 2015-118267 A | 6/2015 | |
| JP | 2015118267 A * | 6/2015 | |
| WO | 2008/058490 A1 | 5/2008 | |
| WO | WO-2008058490 A1 * | 5/2008 | ............. C07F 5/022 |

OTHER PUBLICATIONS

Search Report dated Feb. 27, 2020 by the European Patent Office in counterpart European Patent Application No. 18761904.4.
International Search Report (PCT/ISA/210) dated May 15, 2018 issued by the International Searching Authority in International Application No. PCT/JP2018/007359.
Written Opinion (PCT/ISA/237) dated May 15, 2018 issued by the International Searching Authority in International Application No. PCT/JP2018/007359.
Japanese Office Action dated Oct. 6, 2020 issued by the Japanese Patent Office in counterpart Application No. 2019-503036.
Communication dated May 18, 2020 from the Indian Patent Office in counterpart application No. 201947034609.
Office Action dated Jun. 1, 2021 issued by the Japanese Intellectual Property Office in counterpart Japanese Application No. 2019-503036.
Office Action dated May 19, 2021 issued by the Intellectual Property India Patent Office in Indian application No. 201947034609.
Office Action dated Mar. 12, 2021 by the State Intellectual Property Office of P.R. China in counterpart Chinese Patent Application No. 201880014350.X.
Office Action dated Jun. 16, 2021 issued by the Intellectual Property Office of the P.R. China in Chinese application No. 201880014350.X.

(Continued)

*Primary Examiner* — Chanceity N Robinson
(74) *Attorney, Agent, or Firm* — Sughrue Mion, PLLC

(57) ABSTRACT

A curable composition includes a salt compound having a) an organic anion in which, in Hansen solubility parameter, δd is 16 or more, δp is 16 or more and 32 or less, and δH is 60% or less of δp and b) a counter cation. A lithographic printing plate precursor having an image-recording layer containing the curable composition, a method for producing a lithographic printing plate using the lithographic printing plate precursor, and a compound that is used in the image-recording layer in the lithographic printing plate precursor are also set out.

1 Claim, No Drawings

(56) References Cited

OTHER PUBLICATIONS

Office Action dated Nov. 30, 2021, issued by the Japan Patent Office in counterpart Japanese Patent Application No. 2019-503036.
Communication dated Sep. 14, 2021 by the State Intellectual Property Office of the People's Republic of China in Chinese Patent Application No. 201880014350.X.

* cited by examiner

CURABLE COMPOSITION, LITHOGRAPHIC PRINTING PLATE PRECURSOR, METHOD FOR PRODUCING LITHOGRAPHIC PRINTING PLATE, AND COMPOUND

This is a continuation of International Application No. PCT/JP2018/007359 filed on Feb. 27, 2018, and claims priorities from Japanese Patent Application No. 2017-037779 filed on Feb. 28, 2017, Japanese Patent Application No. 2017-191496 filed on Sep. 29, 2017, and Japanese Patent Application No. 2017-252560 filed on Dec. 27, 2017, and the contents thereof are incorporated herein by reference.

BACKGROUND OF THE INVENTION

1. Field of the Invention

The present invasion relates to a curable composition, a lithographic printing plate precursor, a method for producing a lithographic printing plate, and a compound.

2. Description of the Related Art

A curable composition, particularly, a photocurable composition is a composition having a property of being cured in an irradiated portion by the irradiation with light, and it is possible to produce an image-forming material by applying and drying a coating fluid formed by appropriately dissolving or dispersing this composition in a solvent on an appropriate support to form a photocurable film. As the image-forming material, image-forming materials for which curing by image exposure is used, such as lithographic printing plate precursors, printed-wiring boards, color filters, and photo masks are exemplified.

Hereinafter, a lithographic printing plate precursor will be described as an example.

Generally, a lithographic printing plate includes a lyophilic image area that receives ink in a printing process and a hydrophilic non-image area that receives dampening water Lithographic printing is a method in which the properties of water and oil-based ink that repel each other are used, the lipophilic image area of the lithographic printing plate is used as an ink-receiving portion, the hydrophilic non-image area is used as a dampening water-receiving portion (non-ink-receiving portion), a difference in the adhesive property of ink is caused on the surface of the lithographic printing plate, the die ink is absorbed only in the image area, and then the ink is transferred to a body to be printed such as paper, thereby carrying out printing.

In a plate making step of producing a lithographic printing plate from a lithographic printing plate precursor, al the moment, image exposure is carried out using a computer to plate (CTP) technology. Hat is, image exposure is directly carried out on a lithographic printing plate precursor by means of scanning, exposure, or the like using a laser or a laser diode without using a lith film.

In addition, regarding the plate of lithographic printing plate precursors, doe to the intensifying interest in the global environment, an environmental issue of waste liquid generated by wet processes such as a development process has gathered attention, and accordingly, there have been attempts to simplify or remove development processes. As one of simple development processes, a method called "on-machine development" has been proposed. The on-machine development refers to a method in which, after the image exposure of a lithographic printing plate precursor, a development process of the related art is not carried out, and instead, the lithographic printing plate precursor is attached to a printer, and a non-image area in an image-recording layer is removed at the initial phase of an ordinary printing step.

Generally, lithographic printing plate precursors have an image-recording layer on a support such as an aluminum plate. In the case of a negative-type image-recording layer, the image-recording layer has a function of forming an image area by being cured in an exposed portion by image exposure. Therefore, the image-recording layer contains a component for forming an image by image exposure. As one component that is included in the image-recording layer, a photopolymerization initiator generating a radical by exposure is exemplified.

As the photopolymerization initiator that is included in the image-recording layer, salt compounds including an onium such as iodonium or sulfonium and an inorganic or organic anion as a counter anion are used. As the inorganic or organic anion as the counter anion, a sulfonate anion, a carboxylate anion, a tetrafluoroborate anion, a hexafluorophosphate anion, a p-toluenesulfonate anion, a tosylate anion, and the like are known. For example, JP2009-538446A describes a radiation sensitive composition containing a salt compound including a diaryliodonium cation having a specific structure and a borate anion having a specific structure as a photopolymerization initiator.

Generally, as a previous step of attaching the lithographic printing plate to the printer, an operation of inspecting and identifying an image on the lithographic printing plate (the inspection of the plate) in order to check whether or not the image is recorded as intended on the lithographic printing plate is earned out. Particularly, in polychromatic printing, the capability of determining a register mark which serves as a mark for registration is critical m printing operations.

In lithographic printing plate precursors that are subjected to an ordinary development process step, an image-recording layer is adored, thereby obtaining a colored image by means of a development process, and thus it is possible to easily check the image before the lithographic printing plate et attached to a printer.

However, in on-machine development-type or process-less (development-less)-type lithographic printing plate precursors on which an ordinary development process step is not carried out, it is difficult to check an image on the lithographic printing plate precursor in a phase of attaching the lithographic printing plate precursor to a printer, and thus it is impossible to sufficiently inspect the plate. Therefore, for on-machine development-type or process-less (development-less)-type lithographic printing plate precursors, there is a demand for means for checking an image in a phase of being exposed, that is, the formation of a so-called print-out image in which an exposed region develops or does not develop a color without adversely affecting on-machine development.

As means for forming the print-out image, a method in which a photo-acid generator and an acid color-developing dye (leuco dye) are added to an image-recording layer, and the acid color-developing dye is caused to develop color by an action of an acid generated from the photo-acid generator by image exposure, thereby forming a colored image is known.

Furthermore, lithographic printing plate precursors desirably have favorable thermal and temporal stability. In a case in which the thermal and temporal stability is poor, dark polymerization processes in the lithographic printing plate precursors due to thermal aging, and consequently, on-machine developability degrades. In addition, in lithographic printing plate precursors including an acid color-developing dye such as a leuco dye, there is a problem of the occurrence of ring-shaped color development due to thermal aging. Therefore, the thermal and temporal stability is an important characteristic to lithographic printing plate precursors.

SUMMARY OF THE INVENTION

An object of the present invention is to provide a curable composition that can be used to produce lithographic printing plate precursors having excellent on-machine developability.

Another object of the present invention is to provide a curable composition having favorable thermal and temporal stability.

Still another object of the present invention is to provide a lithographic printing plate precursor which has favorable thermal and temporal stability, is excellent in terms of on-machine developability, and can be used to produce lithographic printing plates having excellent printing resistance.

Still another object of the present invention is to provide a lithographic printing plate precursor which has favorable thermal and temporal stability, is excellent in terms of a plate inspection property and on-machine developability, and can be used to produce lithographic printing plates having excellent printing resistance.

Still another object of the present invention is to provide a lithographic printing plate precursor which has favorable thermal and temporal stability and can be used to produce lithographic printing plates having excellent printing resistance.

Still another object of the present invention is to provide a method for producing a lithographic printing plate using the lithographic printing plate precursor and to provide a compound that is used in an image-recording layer in the lithographic printing plate precursor.

Means for achieving the above-described objects will be described below.

[1] A curable composition comprising a salt compound having a) an organic anion m which, in Hansen solubility parameter, $\delta d$ is 16 or more, $\delta p$ is 16 or more and 32 or less, and $\delta H$ is 60% or less of $\delta p$; and b) a counter cation.

[2] The curable composition according to [1], in which the organic anion is an organic anion having an aromatic ring or a hetero ring in a molecule.

[3] The curable composition according to [1], in which the organic anion is (A) an organic anion having a sulfonamide anion structure tot bonds to a ring or a sulfonimide anion structure that bonds to a ring.

[4] The curable composition according to [2], in which the organic anion is an organic anion represented by Formula (V).

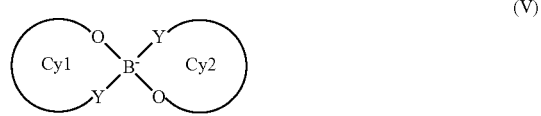

In Formula (V), Cy1 and Cy2 may be identical to or different from each other and each represent a ring structure formed with all of a boron atom, an oxygen atom, and Y, Y's each independently represent —O— or —NR$_5$—, and R$_5$ represents a hydrogen atom, an alkyl carbonyl group, an aryl carbonyl group, an alkyl sulfonyl group, an aryl sulfonyl group, an alkoxycarbonyl group, an aryl group, or a heteroaryl group.

The ring structure represented by Cy1 is fused with an aromatic ring having at least one group selected from the group consisting of an alkylamide group, an alkenylamide group, an arylamido group, an alkylurea group, an arylurea group, a group having a sulfonamide structure, and a group having a sulfonimide structure, and the ring structure represented by Cy2 is fused with an aromatic ring having at least one group selected from the group consisting of an alkylamide group, an alkenylamide group, an arylamide group, an alkylurea group, an arylurea group, a group having a sulfonamide structure, and a group having a sulfonimide structure.

[5] The curable composition according to [4], in which the organic anion is an organic anion represented by Formula (VI).

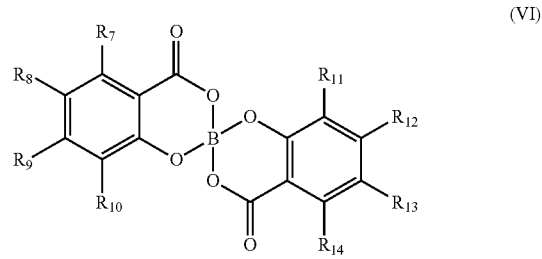

In Formula (VI), R$_7$ to R$_{14}$ may be identical to or different from each other and each independently represent a hydrogen atom, an alkyl group, an alkylamide group, an alkenylamide group, an arylamide group, an alkylurea group, an arylurea group, a group having a sulfonamide structure, or a group having a sulfonimide structure.

At least one of R$_7$, R$_8$, R$_9$, or R$_{10}$ represents an alkylamide group, an alkenylamide group, an arylamide group, an alkylurea group, an acylurea group, a group having a sulfonamide structure, or a group having a sulfonimide structure, and at least one of R$_{11}$, R$_{12}$, R$_{13}$, or R$_{14}$ represents an alkylamide group, an alkenylamide group, an arylamide group, an alkylurea group, an arylurea group, a group having a sulfonamide structure, or a group having a sulfonimide structure.

[6] A curable composition comprising: a salt compound having (A) an organic anion having a sulfonamide anion structure that bonds to a ring or a sulfonimide anion structure that bonds to a ring and (B) a counter cation.

[7] The curable composition according to [6], in which the organic anion is represented by General Formula (I).

In General Formula (I), Cy represents an aryl group, a heteroaryl group, or an alicyclic group that may have an unsaturated bond.

X represents an alkyl group, an aryl group, a heteroaryl group, $SO_2R_a$, $SOR_b$, $COR_c$, $PO_3R_d$, $PO(R_e)(R_f)$, or H. $R_a$, $R_b$, $R_c$, $R_d$, $R_e$, and $R_f$ represent a group selected from the group consisting of an alkyl group, an alkoxy group, an aryl group, a heteroaryl group, and H. $R_a$, $R_b$, $R_c$, $R_d$, $R_e$, or $R_f$ may bond to Cy to form a ring,

[8] The curable composition according to [7], in which the organic anion is represented by General Formula (II).

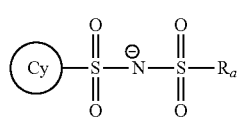

In General Formula (II), Cy represents an aryl group, a heteroaryl group, or an alicyclic group that may have an unsaturated bond.

$R_a$ represents a group selected from the group consisting of an alkyl group, an alkoxy group, an aryl group, a hetetoaryl group, and H. $R_a$ may bond to Cy to form a ring.

[9] The curable composition according to [8], in which the organic anion is represented by General Formula (III) or (IV).

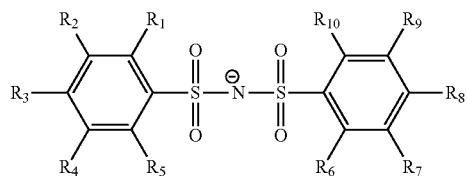

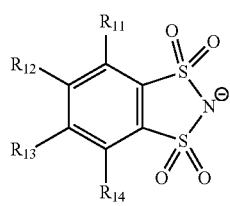

In General Formula (III), $R_1$ to $R_{10}$ each independently represent a hydrogen atom or a monovalent substituent.

In General Formula (IV), $R_{11}$ to $R_{14}$ each independently represent a hydrogen atom or a monovalent substituent.

[10] The curable composition according to any one of [1] to [9], in which the counter cation is a diaryliodonium cation or a triarylsulfonium cation.

[11] The curable composition according to any one of [1] to [9], in which the counter cation is a counter cation in a cyanine-based colorant.

[12] The curable composition according to any one of [1] to [9], in which the counter cation is an alkali metal ion, an alkali earth metal ion or an organic cation having a positive charge present on a nitrogen atom.

[13] The curable composition according to any one of [1] to [10] and [12], further comprising: an infrared absorber.

[14] The curable composition according to [13], in which the infrared absorber is a cyanine-based colorant.

[15] The curable composition according to any one of [1] to [14], further comprising: a polymerizable compound.

[16] The curable composition according to any one of [1] to [15], further comprising: an acid color-developing agent.

[17] The curable composition according to any one of [1] to [16], further comprising: a polymer particle.

[18] The curable composition according to any one of [1] to [17], further comprising: a binder polymer.

[19] The curable composition according to any one of [1] to [18] which is used far a lithographic printing plate.

[20] A lithographic printing plate precursor comprising: an image-recording layer containing the curable composition according to any one of [1] to [19] on a support.

[21] The lithographic printing plate precursor according to [20], further comprising: a protective layer on the image-recording layer.

[22] A method far producing a lithographic printing plate comprising: a step of image-exposing the lithographic printing plate precursor according to [20] or [21]; and a step of removing a non-exposed portion of the image-recording layer on a printer using at least one selected from the group consisting of printing ink and dampening water.

[23] A method far producing a lithographic printing plate comprising: a step of image-exposing the lithographic printing plate precursor according to [20] or [21]; and a step of removing a non-exposed portion of the image-recording layer using a developer having pH of 2 to 11.

[24] A compound comprising: an organic anion which is represented by General Formula (III) or (IV); and a counter cation which is a diaryliodonium cation or a triarylsulfonium cation.

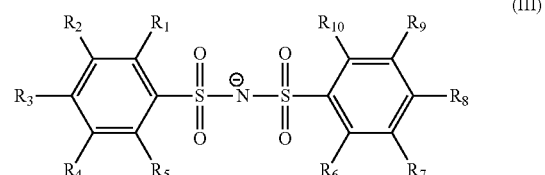

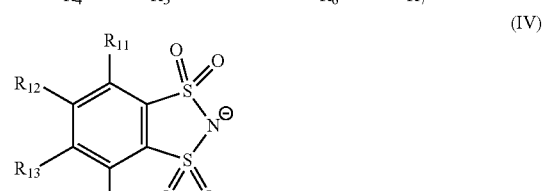

In General Formula (III), $R_1$ to $R_{10}$ each independently represent a hydrogen atom or a monovalent substituent.

In General Formula (IV), $R_{11}$ to $R_{14}$ each independently represent a hydrogen atom or a monovalent substituent.

[25] A compound comprising: an organic anion which is represented by General Formula (III) or (IV); and a counter cation which is a counter cation in a cyanine colorant.

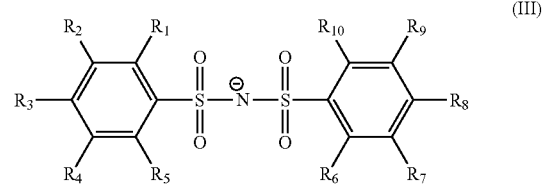

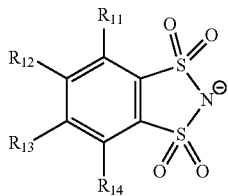

(IV)

In General Formula (III), $R_1$ to $R_{10}$ each independently represent a hydrogen atom or a monovalent substituent.

In General Formula (IV), $R_{11}$ to $R_{14}$ each independently represent a hydrogen atom or a monovalent substituent.

According to the present invention, h is possible to provide a curable composition that can be used to produce lithographic printing plate precursors having excellent on-machine developability.

In addition, according to the present invention, it is possible to provide a curable composition having favorable thermal and temporal stability.

In addition, according to the present invention, it is possible to provide a lithographic printing plate precursor which has favorable thermal and temporal stability, is excellent in terms of on-machine developability, and can be used to produce lithographic printing plates having excellent printing resistance.

Furthermore, according to the present invention, it is possible to provide a lithographic printing plate precursor which has favorable thermal and temporal stability, is excellent in terms of a plate inspection property and on-machine developability, and can be used to produce lithographic printing plates having excellent printing resistance.

Furthermore, according to the present invention, it is possible to provide a lithographic printing plate precursor which has favorable thermal and temporal stability and can be used to produce lithographic printing plates having excellent printing resistance.

Furthermore, according to toe present invention, it is possible to provide a method for producing a lithographic printing plate using toe lithographic printing plate precursor and a compound that is used in an image-recording layer in toe lithographic printing plate precursor.

DESCRIPTION OF THE PREFERRED EMBODIMENTS

Hereinafter, toe present invention will be described in detail.

Meanwhile, in the present specification, the expression "xx to yy" indicates a numerical range including xx and yy.

In addition, in toe present specification, "(meth)acryl" represents either or both of acryl and methacryl, and "(meth) acrylate" represents either or both of acrylate and methacrylate.

In addition, in the present invention, "% by mass" and "% by weight" have toe same meaning, and "parts by mass" and "parts by weight" have toe same meaning.

In addition, in toe present invention, a combination of two or more preferred aspects is a more preferred aspect.

In addition, unless particularly otherwise described, toe weight-average molecular weight (Mw) in toe present invention refers to a molecular weight that is detected using a gel permeation chromatography (GPC) analyzer in which columns of TSKgel GMHxL, TSKgel G4000HxL, and TSKgel G2000HxL (all are trade names manufactured by Tosoh Corporation) are used, solvent tetrahydrofuran (THF), and a differential refractometer and is converted using polystyrene as a standard substance.

In the present specification, regarding toe expression of a group in a compound represented by a formula, in a case in which there is no description of whether toe group is substituted or unsubstituted, unless particularly otherwise described, the group refers not only to an unsubstituted group but also to toe group having a substituent as long as the group is capable of having a substituent. For example, for a formula, in a case in which there is a description "R represents an alkyl group, an aryl group, or a monovalent heterocyclic group", it means that "R represents an unsubstituted alkyl group, a substituted alkyl group, an unsubstituted aryl group, a substituted aryl group, an unsubstituted monovalent heterocyclic group, or a monovalent heterocyclic group having a substituent".

In the present specification, toe term "step" refers not only to an independent step but also to a step that is not clearly differentiated from other steps as long as the intended object is achieved.

[Curable Composition]

As a first aspect, a curable composition of an embodiment of the present invention contains a salt compound (hereinafter, also referred to as "parameter-regulating compound") having a) an organic anion (hereinafter, also referred to as "a) organic anion" or "first organic anion") in which, in Hansen solubility parameter, $\delta d$ is 16 or more, $\delta p$ is 16 or more and 32 or less, and $\delta H$ is 60% or less of $\delta p$; and b) a counter cation.

Meanwhile, the units of $\delta d$, $\delta p$, and $\delta H$ are $MPa^{0.5}$.

The curable composition (also referred to as "first composition") according to the first aspect of the present invention is a composition that can be used to produce lithographic printing plate precursors that are excellent in terms of on-machine developability due to the above-described constitution.

The reason therefor is not clear, but is assumed as described below.

First, the present inventors assumed that, in the on-machine development of lithographic printing plate precursors using ink and dampening water, generally, the difference between the solubility parameter (SP value) of ink and the solubility parameter (SP value) of water is great, and thus a non-image area in an image-forming layer that is supposed to be removed in on-machine development is originally exposed to an environment having a weak affinity to both ink and dampening water, which causes the degradation of on-machine developability.

Meanwhile, as the solubility parameter (SP value), Hansen solubility parameter is exemplified, and, as the Hansen solubility parameter, $\delta d$ that contributes to dispersibility, $\delta p$ that contributes to polarity, and $\delta H$ that contributes to a hydrogen bond are known. Recently, the present inventors have found that an on-machine developability for lithographic printing plate precursors is improved by adding a specific salt compound having an organic anion regulated using these three parameters to the curable, composition and completed the above-described constitution.

Specifically, first, the curable composition is constituted so that, in a case in which $\delta d$ is set to 16 or more in the organic anion of the salt compound, a sufficient intermolecular force is developed between these salt compounds due to the interaction or the like between a lipophilic group and a lipophilic group that the mutual compounds have. Therefore, it is considered that, before on-machine development, the image-forming layer is put into a desired state, and, during on-machine development, the intermolecular force is likely to decrease due to the ink relaxing the interaction or the like.

In addition, it is considered that, in a case in which δp is set to 16 or more in the organic anion of the salt compound, the degree of polarity of the salt compound is increased, and thus, during on-machine development, the non-image area in the image-forming layer also has an affinity to water.

However, as a result of intensive studies, the present inventors found that it is not to simply a salt compound having an organic anion halving δp of 16 or more to the image-recording layer, and, first, it is necessary to set δp to 32 or less. This is assumed to be because, in a case in which the degree of polarity of the salt compound is too high, the non-affinity to ink increases, and consequently, the non-image area is not smoothly removed.

In addition, as a result of intensive studies, the present inventors found that it is also necessary to set δH to 60% or less of δp. The detailed reason therefor is not clear, but is assumed that, in the on-machine development of lithographic printing plate precursors using ink and dampening water, for the removal of the non-image area and, furthermore, the improvement of on-machine developability, it becomes necessary to set δH to be a certain value or less of δp, that is, set the contribution of a hydrogen bond to be a certain degree or less and then increase the degree of polarity of the salt compound.

As described above, the salt compound is considered to have a property of selectively solvating ink and dampening water present during the on-machine development of lithographic printing plate precursors and, furthermore, have an affinity to both ink and dampening water. As a result, it is considered that the curable composition according to the first aspect of the present invention can be used to produce lithographic printing plate precursors that are excellent in terms of on-machine developability.

δd, δp, and δH in Hansen solubility parameter can be respectively computed using commercially available Hansen Solubility Parameter in Practice version 4.1.07.

δd in Hansen solubility parameter is 16 or more, preferably 18 or more, and still more preferably 20 or more.

The upper limit value of δd in Hansen solubility parameter is not particularly limited, but is preferably 32 or less and more preferably 28 or less.

δp in Hansen solubility parameter is 16 or more and 32 or less, preferably 18 or more and 30 or less, and still more preferably 20 or more and 28 or less.

δH in Hansen solubility parameter is 60% or less of δp, preferably 55% or less of δp, and more preferably 50% or less of δp.

δH is preferably 20% or more of δp and more preferably 30% or more of δp.

The salt compound that is contained in the curable composition according to the first aspect of the present invention is a compound in which a) the organic anion and b) the counter cation bond to each other through an ionic bond.

[a] Organic Anion a) The organic anion is preferably an organic anion having an aromatic ring or a hetero ring in the molecule from the viewpoint of easily satisfying the above-described requirement "in Hansen solubility parameter. δd is 16 or more, δp is 16 or mote and 32 or less, and δH is 60% or less of δp".

The aromatic ring is specifically an aromatic hydrocarbon ring, and, as the aromatic hydrocarbon ring, aromatic hydrocarbon rings having 6 to 20 carbon atoms are exemplified, and, specifically, benzene, naphthalene, anthraquinone, and the like are exemplified.

The hetero ring is a hetero ring including at least one hetero atom selected from an oxygen atom, a sulfur atom, and a nitrogen atom. The hetero ring is preferably a five-membered ring to an eight-membered ring. The hetero ring may be saturated or unsaturated. The hetero ring is preferably an aromatic hetero ring.

Examples of the hetero ring include a pyridine ring, a pyrimidine ring, a pyrroline ring, and the like.

The parameter-regulating compound is not particularly limited as long as the organic anion satisfies the requirement "in Hansen solubility parameter, δd is 16 or more, δp is 16 or more and 32 or less, and δH is 60% or less of δp", but a) the organic anion is preferably is (A) an organic anion having a sulfonamide anion structure that bonds to a ring or a sulfonimide anion structure that bonds to a ring, whereby the above-described requirement can be easily satisfied.

Meanwhile, (A) the organic anion having a sulfonamide anion structure that bonds to a ring or a sulfonimide anion structure that bonds to a ring is as described below.

In addition, a) the organic anion is also preferably a borate anion and, particularly, preferably an organic anion represented by Formula (V). In such a case, the requirement "in Hansen solubility parameter, δd is 16 or more, δp is 16 or more and 32 or less, and δH is 60% or less of δp" can be easily satisfied.

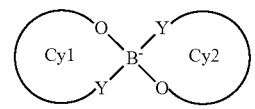

(V)

In Formula (V), Cy1 and Cy2 may be identical to or different from each other and each represent a ring structure formed with all of a boron atom, an oxygen atom, and Y, Y's each independently represent —O— or —NR$_5$—, and R$_5$ represents a hydrogen atom, an alkyl carbonyl group, an aryl carbonyl group, an alkyl sulfanyl group, an aryl sulfanyl group, an alkoxycarbonyl group, an aryl group, or a heteroaryl group.

The ring structure represented by Cy1 is fused with an aromatic ring having at least one group selected from the group consisting of an alkylamide group, an alkenylamide group, an arylamido group, an alkylurea group, an arylurea group, a group having a sulfenamide structure, and a group having a sulfonimide structure, and the ring structure represented by Cy2 is fused with an aromatic ring having at least one group selected from the group consisting of an alkylamide group, an alkenylamide group, an arylamido group, an alkylurea group, an arylurea group, a group having a sulfonamide structure, and a group having a sulfonimide structure.

As the aromatic ring, for example, a benzene ring, a naphthalene ring, and an anthracene ring are exemplified.

In Formula (V), an atomic chain that constitutes the ring structure represented by Cy1 or Cy2 is represented by, for example, —O—C—C—O—, —O—C—C—C—O—, —O—C—C—NR$_5$—, —O—C—C—C—NR$_5$—. Here, both —O— and —NR$_5$— at both ends directly bond to a boron atom. A carbon atom that constitutes the ring structure may have a substituent, and examples thereof include an oxy group (=O), an alkyl group, and an aryl group. In addition, adjacent two carbon atoms are fused with an aromatic ring. As the aromatic ring that is fused to adjacent two carbon atoms, the above-described aromatic rings are exemplified.

The aromatic ring has at least one group selected from the group consisting of an alkylamide group, an alkenylamide group, an arylamido group, an alkylurea group, an arylurea group, a group having a sulfonamide structure, and a group having a sulfonimide structure.

The aromatic ring may have a substituent, and examples of the substituent include an alkyl group and the like.

In Formula (V), Y is preferably —O—. Examples of ring structure represented by Cy1 or Cy2 include ring structures formed of catechol, salicylic acid, an oxalic acid derivative, and a central atom B and the like.

The ring structure represented by Cy1 is fused with an aromatic ring having at least one group selected from the group consisting of an alkylamide group, an alkenylamide group, an arylamido group, an alkylurea group, an arylurea group, a group having a sulfonamide structure, and a group flaying a sulfonimide structure, and the ring structure represented by Cy2 is fused with an aromatic ring having at least one group selected from the group consisting of an alkylamide group, an alkenylamide group, an arylamido group, an alkylurea group, an acylurea group, a group having a sulfonamide structure, and a group having a sulfonimide structure.

In the at least one group selected from the group consisting of an alkylamide group, an alkenylamide group, an arylamido group, an alkylurea group, an arylurea group, a group having a sulfonamide structure, and a group having a sulfonimide structure, an alkyl group in the alkylamide group and an alkyl group in the alkylurea group are preferably an alkyl group having 1 to 12 carbon atoms, more preferably an alkyl group having 1 to 8 carbon atoms, and still more preferably an alkyl group having 1 to 4 carbon atoms. The alkyl group may be linear or branched. Examples of the alkyl group include a methyl group, an ethyl group, a propyl group, an isopropyl group, a butyl group, an isobutyl group, a sec-butyl group, a tert-butyl group, a pentyl group, an isopentyl group, a hexyl group, an octyl group, a tert-octyl group, a nonyl group, a decyl group, a dodecyl group, and the like. The alkyl group may have a substituent, and examples of the substituent include an alkoxy group, an aryloxy group, an aryl group, an alkoxycarbonyl group, a cyano group, and the like.

In the at least one group selected from the group consisting of an alkylamide group, an alkenylamide group, an arylamido group, an alkylurea group, an arylurea group, a group having a sulfonamide structure, and a group having a sulfonimide structure, an alkenyl group in the alkenylamide group is preferably an alkenyl group having 2 to 12 carbon atoms and more preferably an alkenyl group having 2 to 6 carbon atoms. The alkenyl group may be linear or branched. Examples of the alkenyl group include an ethenyl group, a propenyl group, and the hire. The alkenyl group may have a substituent, and examples of the substituent include an alkoxy group, an alkyl carbonyl group, and the like.

In the at least one group selected from the group consisting of an alkylamide group, an alkenylamide group, an arylamido group, an alkylurea group, an arylurea group, a group having a sulfonamide structure, and a group having a sulfonimide structure, an aryl group in the arylamido group and an aryl group in the arylurea group are preferably an aryl group having 6 to 20 carbon atoms and more preferably an aryl group having 6 to 10 carbon atoms. Examples of the aryl group include a phenyl group, a naphthyl group, and the like. The aryl group may have a substituent, and examples of the substituent include an alkyl group, an alkoxy group, an aryloxy group, an aryl group, an alkoxycarbonyl group, a cyano group, an amide group, a urea group, a halogen atom, and the like.

In the al least one group selected from the group consisting of an alkylamide group, an alkenylamide group, an arylamido group, an alkylurea group, an acylurea group, a group having a sulfonamide structure, and a group having a sulfonimide structure, the sulfonamide structure in the group having a sulfonamide structure represents the following structure. Meanwhile, in the following structure, * represents a bonding site.

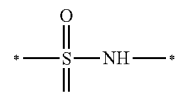

Sulfonamide structure

In the at least one group selected from the group consisting of an alkylamide group, an alkenylamide group, an arylamide group, an alkylurea group, an arylurea group, a group having a sulfonamide structure, and a group having a sulfonamide structure, the sulfonimide structure in the group having a sulfonimide structure represents the following structure. Meanwhile, in the following structure, * represents a bonding site.

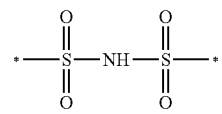

Sulfonimide structure a) The organic anion is preferably an organic anion represented by Formula (VI).

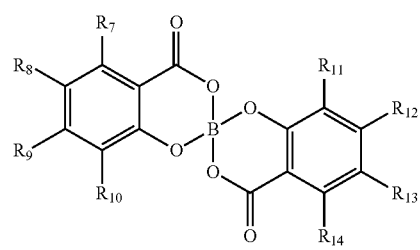

(VI)

In Formula (VI), $R_7$ to $R_{14}$ may be identical to or different from each other and each independently represent a hydrogen atom, an alkyl group, an alkylamide group, an alkenylamide group, an arylamide group, an alkylurea group, an acylurea group, a group having a sulfonamide structure, or a group having a sulfonimide structure.

At least one of $R_7$, $R_8$, $R_9$, or $R_{10}$ represents an alkylamide group, an alkenylamide group, an arylamide group, an alkylurea group, an arylurea group, a group having a sulfonamide structure, or a group having a sulfonimide structure, and al least one of $R_{11}$, $R_{12}$, $R_{13}$, or $R_{14}$ represents an alkylamide group, an alkenylamide group, an arylamide group, an alkylurea group, an arylurea group, a group having a sulfonamide structure, or a group having a sulfonimide structure.

The alkyl group as $R_7$ to $R_{14}$ is identical to the alkyl group in the alkylamide group and the alkyl group in the alkylurea group in the ring structure represented by Cy1 that is fused with an aromatic ring having al least one group selected from the group consisting of an alkylamide group, an alkenylamide group, an arylamide group, an alkylurea group, an arylurea group, a group having a sulfonamide structure, and a group having a sulfonimide structure, and a preferred range thereof is also identical thereto.

The alkylamide group, the alkenylamide group, the arylamide group, the alkylurea group, the arylurea group, the group having a sulfonamide structure, and the group having a sulfonimide structure are respectively identical to the alkylamide group, the alkenylamide group, the arylamide group, the alkylurea group, the arylurea group, the group having a sulfonamide structure, and the group having a sulfonimide structure in the at least one group selected from the group consisting of an alkylamide group, an alkenylamide group, an arylamide group, an alkylurea group, an acylurea group, a group having a sulfonamide structure, and a group having a sulfonimide structure that the aromatic ring to which the ring structure represented by Cy1 or Cy2 is fused has, and preferred ranges thereof are also identical thereto.

Specific examples of the borate anion as a) the organic anion will be illustrated below as an anion portion, fort the present invention is not limited thereto.

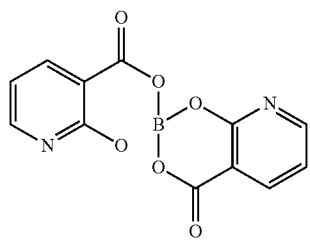
B-1

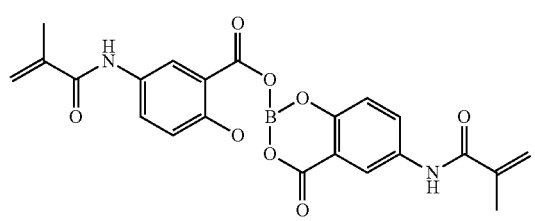
B-2

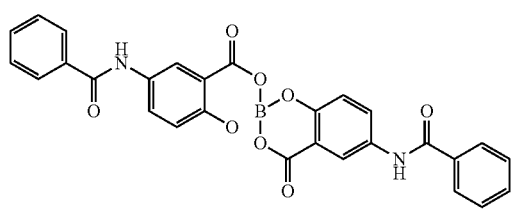
B-3

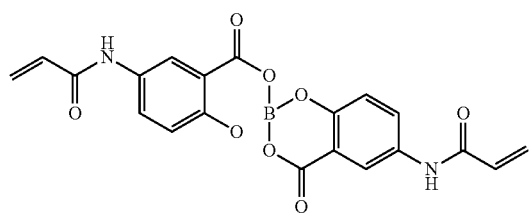
B-4

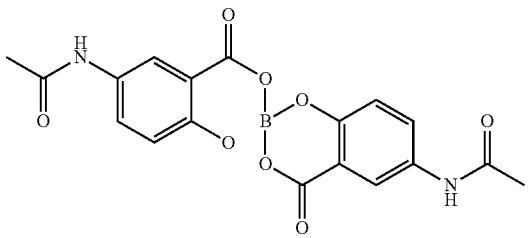
B-5

δd, δp, δH, and the percentage (%) of δH to δp ((δH/δp)×100) in Hansen solubility parameters of B-1, B-2, B-3, B-4, and B-5 are shown in the following table.

|  | δd | δp | δH | δH/δp |
|---|---|---|---|---|
| B-1 | 20.7 | 16.5 | 6.5 | 39% |
| B-2 | 19.6 | 19.7 | 10.4 | 53% |
| B-3 | 19.8 | 18.9 | 10.8 | 57% |
| B-4 | 20.4 | 22.1 | 12 | 54% |
| B-5 | 20.2 | 21.1 | 11.6 | 55% |

[b) Counter Cation]

b) The counter cation is identical to (B) a counter cation described below.

The parameter-regulating confound according to foe present invention may be used singly or two or more parameter-regulating compounds may be jointly used. In foe first composition of the embodiment of the present invention, the content of the parameter-regulating confound is identical to foe content of a specific compound described below.

[Curable Composition]

As a second aspect, a curable composition of the embodiment of the present invention contains a salt compound having (A) an organic anion (hereinafter, also referred to as "(A) organic anion" or "second organic anion") having a sulfonamide anion structure dot bonds to a ring or a sulfonimide anion structure that bonds to a ring and (B) a counter cation.

The salt compound (hereinafter, also simply referred to as "specific compound") that is contained in the curable composition (hereinafter, also simply referred to as "Second composition") according to the embodiment of the present invention is a compound in which (A) the organic anion and (B) the counter cation bond to each other through an ionic bond.

[(A) Organic Anion]

The sulfonamide anion structure in (A) the organic anion represents an anion structure formed by removing a hydrogen atom from the following sulfonamide structure. Meanwhile, in the following structure, * represents a bonding she.

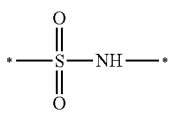 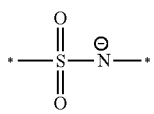

Sulfonamide structure   Sulfonamide anion structure

The sulfonimide anion structure in (A) the organic anion represents an anion structure formed by removing a hydrogen atom from the following sulfonimide structure. Meanwhile, in the following structure, * represents a bonding site.

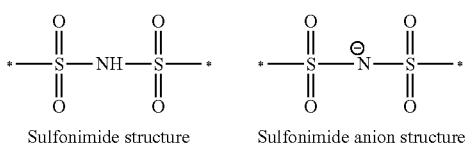

Sulfonimide structure    Sulfonimide anion structure (A) The organic anion in the present invention has a negative charge present on a nitrogen atom, but may be a structure that can be described by, for example, a resonant structure and has a negative charge present at a location other than the nitrogen atom. For example; as an example, a resonant structure in a sulfonimide anion will be illustrated below.

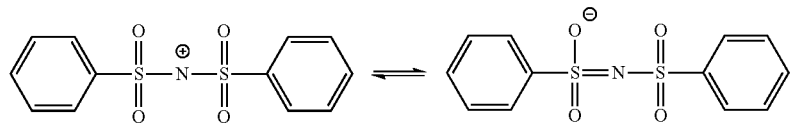 [SMILES: O=S(=O)([NH2+]S(=O)(=O)c1ccccc1)c1ccccc1 ; O=S(=O)(N=S(=O)([O-])c1ccccc1)c1ccccc1]

(A) The organic anion in the present invention may be a form having one sulfonamide anion structure and one sulfonimide anion structure or a form having two or more sulfinamide anion structures and two or mote sulfonimide anion structures.

A ring in the organic anion that constitutes the specific compound according to the present invention is not particularly limited, and an aromatic hydrocarbon ring, an alicyclic hydrocarbon ring, a hetero ring, and the like are exemplified.

As aromatic hydrocarbon ring, aromatic hydrocarbon rings having 6 to 20 carbon atoms are exemplified, and, specifically, benzene, naphthalene, anthraquinone, and the like are exemplified.

As the alicyclic hydrocarbon ring, alicyclic hydrocarbon rings having 3 to 30 carbon atoms are exemplified meanwhile, the alicyclic hydrocarbon ring may have an unsaturated bond.

The hetero ring is a hetero ring including at least one hetero atom selected from an oxygen atom, a sulfur atom, or a nitrogen atom. The hetero ring is preferably a five-membered ring to an eight-membered ring. The hetero ring may be saturated or unsaturated. The hetero ring is preferably an aromatic hetero ring.

Examples of the hetero ring include a pyridine ring, a pyrimidine ring, a pyrroline ring, and the like.

(A) The organic anion in the present invention is preferably an organic anion represented by General Formula (I). Meanwhile, the organic anion according to the present invention, similar to an ordinary anion, can be represented by a plurality of resonant structure formulae according to the electron disposition; however, in the present specification, as illustrated below, the organic anion is illustrated using a resonant structure formula having a negative charge on a nitrogen atom.

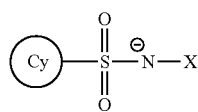 (I)

In General Formula (I), Cy represents an aryl group, a heteroaryl group, or an alicyclic group that may have an unsaturated bond.

X represents an alkyl group, an aryl group, a heteroaryl group, $SO_2R_a$, $SOR_b$, $COR_c$, $PO_3R_d$, $PO(R_a)(R_f)$, or H. $R_a$, $R_b$, $R_c$, $R_d$, $R_e$, and $R_f$ represent a group selected from the group consisting of an alkyl group, an alkoxy group, an aryl group, a heteroaryl group, and H. $R_a$, $R_b$, $R_c$, $R_d$, $R_e$, or $R_f$ may bond to Cy to form a ring.

The aryl group represented by Cy is preferably an aryl group having 6 to 20 carbon atoms, more preferably an aryl group having 6 to 15 carbon atoms, and still more preferably an aryl group having 6 to 10 carbon atoms. Examples of the aryl group include a phenyl group, a naphthyl group, and the like. A phenyl group or the like is preferred.

The heteroaryl group represented by Cy is a group formed of a hetero ring including at least one hetero atom selected from an oxygen atom, a sulfur atom, or a nitrogen atom. The hetero ring is preferably a five-membered ring to an eight-membered ring and more preferably a five-membered ring or a six-membered ring. Examples of the heteroaryl group include a pyridyl poop, a pyrimidyl group, a pyrrolyl group, furanyl group, an imidazolyl group, a pyrazolyl group, a triazolyl group, a tetrazolyl group, an indolyl group, a quinolinyl group, an oxadiazolyl group, a benzoxazolyl group, and the like.

The alicyclic group represented by Cy is a group formed of an alicycle having 3 to 30 carbon atoms and preferably an alicycle having 4 to 9 carbon atoms. The alicycle may be monocyclic or polycyclic. In addition, the alicycle may have an unsaturated bond.

Examples of the alicyclic group that may have an un saturated bond include a cyclopentanyl group, a cyclopentadienyl group, a cyclohexenyl group, a cyclohexathenyl group, a cycloheptenyl group, a cycloheptathenyl group, a norbornene group, and the like.

The aryl group or the heteroaryl group may have a substituent, and examples of the substituent include groups formed of one or a combination of two or mote of an alkyl group, an alkoxy group, an aryloxy group, an aryl group, a carbonyl group, an alkoxycarbonyl group, a cyano group, an amide group, a urea group, a urethane group, an alkenyl group, an allyl group, an acrylic group, a methacrylic group, an acrylamide group, a methacrylamide group, and a halogen atom and the like.

In Formula (I), the alkyl group represented by X is preferably an alkyl group having 1 to 12 carbon atoms, more preferably an alkyl group having 1 to 10 carbon atoms, and still more preferably an alkyl group having 1 to 8 carbon atoms. The alkyl group may be linear or branched. Examples of the alkyl group include a methyl group, an ethyl group, a propyl group, an isopropyl poop, a butyl group, an isobutyl group, a secbutyl group, a tertbutyl group, a pentyl group, an isopentyl group, a hexyl group, an octyl group, a tert-octyl group, a nonyl group, a decyl group, a dodecyl group, an ethylhexyl group, and the like. As foe alkyl group, a methyl group, an ethyl group, and a tertbutyl group are preferred.

In Formula (I), the aryl group and the heteroaryl group represented by X are identical to the aryl group and the heteroaryl group represented by Cy in Formula (I), and preferred ranges thereof are also identical thereto.

In Formula (I), the alkyl group, the aryl group, and the heteroaryl group represented by $R_a$, $R_b$, $R_c$, $R_d$, $R_e$, and $R_f$ are identical to the alkyl group, the aryl group, and the heteroaryl group represented by X in Formula (I), and preferred ranges thereof are also identical thereto meaning.

In Formula (I), the alkoxy group represented by $R_a$, $R_b$, $R_c$, $R_d$, $R_e$, and $R_f$ is preferably an alkoxy group having 1 to 20 carbon atoms, more preferably an alkoxy group having 1 to 16 carbon atoms, and still more preferably an alkoxy group having 1 to 12 carbon atoms.

The alkyl group, the aryl group, or the heteroaryl group represented by X may have a substituent, and examples of the substituent include groups formed of one or a combination of two or more of an alkyl group, an alkoxy group, an aryloxy group, an aryl group, a carbonyl group, an alkoxycarbonyl group, a cyano group, an amide group, a urea group, a urethane group, an alkenyl group, an allyl group, an acrylic group, a methacrylic group, an acrylamide group, a methacrylamide group, and a halogen atom and the like.

In addition, the alkyl group, the alkoxy group, the aryl group, or the heteroaryl group represented by $R_a$, $R_b$, $R_c$, $R_d$, $R_e$, $R_f$, and $R_g$ may have a substituent, and examples of the substituent include groups formed of one or a combination of two or more of an alkyl group, an alkoxy group, an aryloxy group, an aryl group, a carbonyl group, an alkoxycarbonyl group, a cyano group, an amide group, a urea group, a urethane group, alkenyl group, an allyl group, an acrylic group, a methacrylic group, an acrylamide group, a methacrylamide group, and a halogen atom and the like.

X is preferably an alkyl group, a heteroaryl group, $SO_2R_a$, $SOR_b$, $COR_c$, $PO_3R_d$, $PO(R_e)(R_f)$, or H.

$R_a$, $R_b$, $R_c$, $R_d$, $R_e$, or $R_f$ may bond to Cy to form a ring. Meanwhile, the fact that X is $SO_2R_a$, $R_a$ is H (hydrogen atom), and $R_a$ bonds to Cy to form a ring indicates that H as $R_a$ is desorbed, and $SO_2$ bonds to Cy.

(A) The organic anion in the present invention is preferably an organic anion represented by General Formula (II).

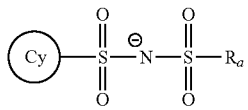

(II)

In General Formula (II), Cy represents an aryl group, a heteroaryl group, or an alicyclic group that may have an unsaturated bond.

$R_a$ represents a group selected from the group consisting of an alkyl group, an alkoxy group, an aryl group, a heteroaryl group, and H. $R_a$ may bond to Cy to form a ring, In Formula (II), the aryl group, the heteroaryl group, and the alicyclic poop that may have an unsaturated bond represented by Cy are identical to the aryl group, the heteroaryl group, and the alicyclic group that may have an unsaturated bond represented by Cy in Formula (I), and preferred ranges thereof are also identical thereto.

The aryl group or the heteroaryl group represented by Cy may have a substituent, and examples of the substituent include groups formed of one or a combination of two or more of an alkyl group, an alkoxy group, an aryloxy group, an aryl group, a carbonyl group, an alkoxycarbonyl group, a cyano group, an amide group, a urea group, a urethane group, an alkenyl group, an allyl group, an acrylic group, a methacrylic group, an acrylamide group, a methacrylamide group, and a halogen atom and the like.

$R_a$ in General Formula (II) is identical to $R_a$ in X in General Formula (I), and a preferred range thereof is also identical thereto.

In addition, the alkyl group, the alkoxy group, the aryl group, or the heteroaryl group represented by $R_a$ may have a substituent, and examples of the substituent include groups formed of one or a combination of two or more of an alkyl group, an alkoxy group, an aryloxy group, an aryl group, a carbonyl group, an alkoxycarbonyl group, a cyano group, an amide group, a urea group, a urethane group, an alkenyl group, an allyl group, an acrylic group, a methacrylic group, an acrylamide group, a methacrylamide group, and a halogen atom and the like.

(A) The organic anion in the present invention is preferably an organic anion represented by General Formula (III) or (IV).

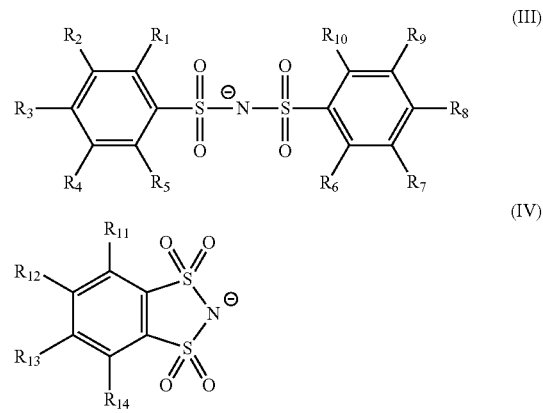

In General Formula (III), $R_1$ to $R_{10}$ each independently represent a hydrogen atom or a monovalent substituent.

In General Formula (IV), $R_{11}$ to $R_{14}$ each independently represent a hydrogen atom or a monovalent substituent.

In General Formula (III), the monovalent substituent represented by $R_1$ to $R_{10}$ is not particularly limited as long as the effects of the present invention are not impaired, and examples thereof include groups formed of one or a combination of two or more of an alkyl group (an alkyl group having 1 to 12 carbon atoms is preferred, an alkyl group having 1 to 10 carbon atoms is more preferred, and an alkyl group having 1 to 8 carbon atoms is still more preferred. The alkyl group may be linear or branched.), an alkoxy group (an alkyl group in the alkoxy group is preferably an alkyl group having 1 to 12 carbon atoms, mote preferably an alkyl group having 1 to 10 carbon atoms, and still more preferably an alkyl group having 1 to 8 carbon atoms. The alkyl group may be linear or branched), an aryloxy group (an aryl group in the aryloxy group is preferably an aryl group having 6 to 20 carbon atoms, more preferably an aryl group having 6 to 15 carbon atoms, and still more preferably an aryl group having 6 to 10 carbon atoms.), an aryl group (an aryl group having 6 to 20 carbon atoms is preferred, an aryl group having 6 to 15 carbon atoms is more preferred, and an aryl group having 6 to 10 carbon atoms is still more preferred.), a carbonyl group, an alkoxycarbonyl group (an alkyl group in the alkoxycarbonyl group is preferably an alkyl group having 1 to 12 carbon atoms, more preferably an alkyl group having 1 to 10 carbon atoms, and still more preferably an alkyl group having 1 to 8 carbon atoms. The alkyl group may be linear or branched.), a cyano group, an amide group, a urea group, a urethane group, an alkoxyl group (an alkenyl group preferably having 2 to 15 carbon atoms and more preferably having 2 to 6 carbon atoms), an allyl group, an acrylic gimp, a methacrylic group, an acrylamide group, a methacrylamide group, and a halogen atom (a fluorine atom, a chlorine atom, a bromine atom, or an iodine atom) and the like.

The groups exemplified as the monovalent substituent may be further substituted with a different group.

In General Formula (III), as the group represented by $R_1$ to $R_{10}$, a hydrogen atom and the above-described monovalent substituent are preferred, and an alkyl group, a halogen group, and an alkoxycarbonyl group are more preferred.

In General Formula (IV), the monovalent substituent represented by $R_{11}$ to $R_{14}$ is not particularly limited as long as the effects of the present invention are not impaired, and examples thereof include groups formed of one or a combination of two or more of an alkyl group (an alkyl group having 1 to 12 carbon atoms is preferred, an alkyl group having 1 to 10 carbon atoms is mote preferred, and an alkyl group having 1 to 8 carbon atoms is still more preferred. The alkyl gimp may be linear or branched.), an alkoxy group (an alkyl group in the alkoxy group is preferably an alkyl group having 1 to 12 carbon atoms, more preferably an alkyl group having 1 to 10 carbon atoms, and still mote preferably an alkyl group having 1 to 8 carbon atoms. The alkyl group may be linear or branched), an aryloxy group (an aryl group in the aryloxy group is preferably an aryl group having 6 to 20 carbon atoms, more preferably an aryl group having 6 to 15 carbon atoms, and still more preferably an aryl group having 6 to 10 carbon atoms), an aryl group (an aryl group having 6 to 20 carbon adorns is preferred, an aryl group having 6 to 15 carbon atoms is more preferred and an aryl group having 6 to 10 carbon atoms is still more preferred), a carbonyl group, an alkoxycarbonyl group (an alkyl group in the alkoxycarbonyl group is preferably an alkyl group having 1 to 12 carbon atoms, more preferably an alkyl group having 1 to 10 carbon atoms, and still more preferably an alkyl group having 1 to 8 carbon atoms. The alkyl group may be linear or branched), a cyano group, an amide group, a urea group, a urethane group, an alkenyl group (an alkenyl group preferably having 2 to 15 carbon atoms and more preferably having 2 to 6 carbon atoms), an allyl group, an acrylic group, a methacrylic group, an acrylamide group, a methacrylamide group, and a halogen atom (a fluorine atom, a chlorine atom, a bromine atom, or an iodine atom) and the like.

The groups exemplified as the monovalent substituent may be further substituted with a different group.

In General Formula (IV), as the group represented by $R_{11}$ to $R_{14}$, a hydrogen atom and the above-described monovalent substituent are preferred rod an alkyl group, a halogen group, and an alkoxycarbonyl group are more preferred.

Organic anions having two or more sulfonimide anion structures through any of $R_1$ to $R_{10}$ are also represented by General Formula (III).

Specific examples of (A) the organic anion will be illustrated below as an anion portion, but the present invention is not limited thereto.

Anion portion

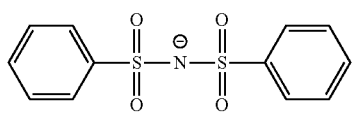
I-1

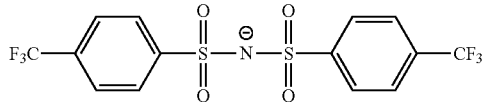
I-2

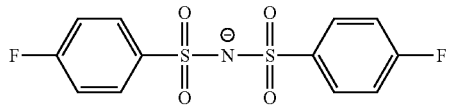
I-3

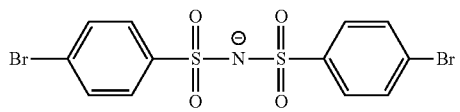
I-4

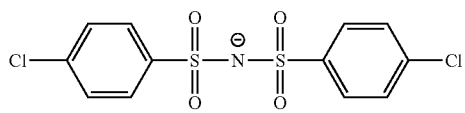
I-5

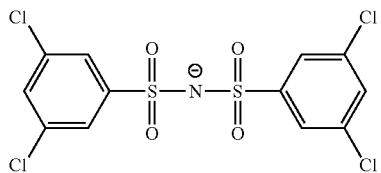
I-6

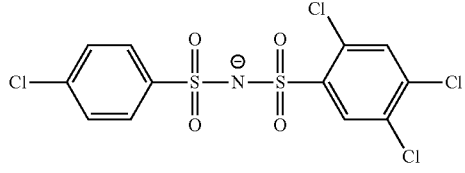
I-7

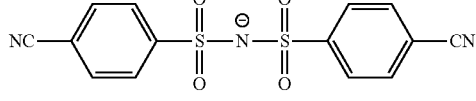
I-8

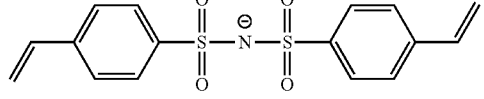
I-9

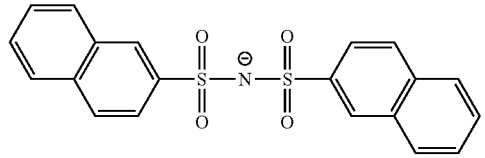
I-10

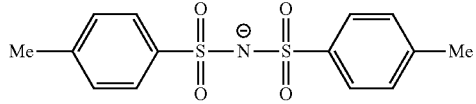
I-11

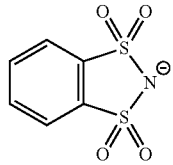
I-12

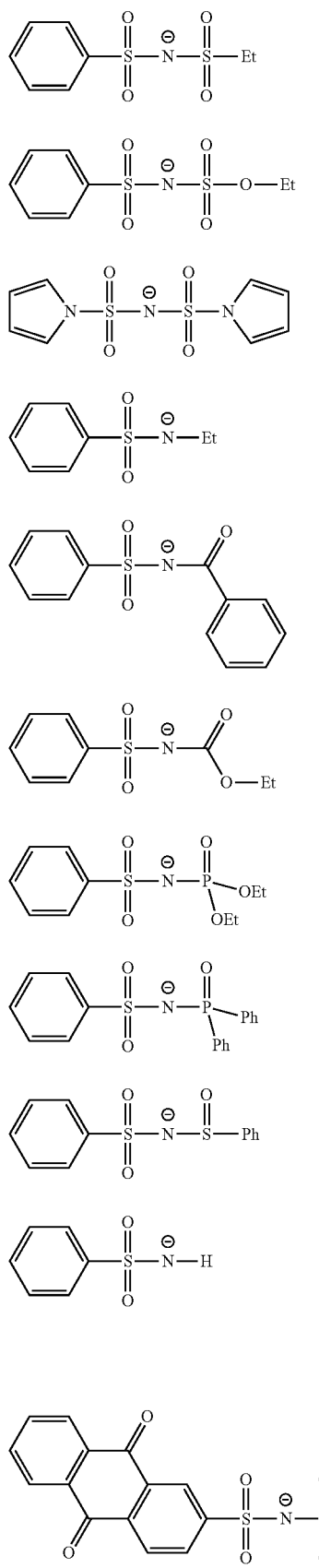
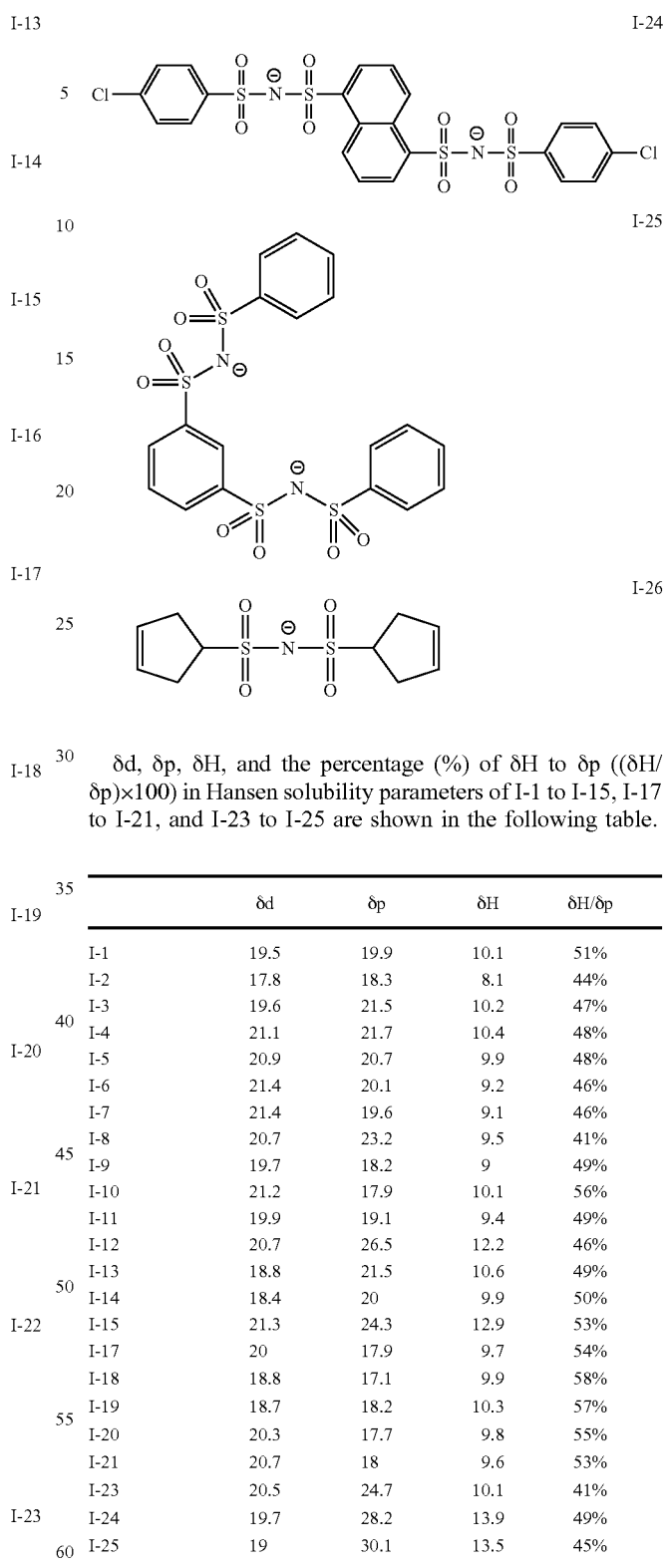

δd, δp, δH, and the percentage (%) of δH to δp ((δH/δp)×100) in Hansen solubility parameters of I-1 to I-15, I-17 to I-21, and I-23 to I-25 are shown in the following table.

|      | δd   | δp   | δH   | δH/δp |
|------|------|------|------|-------|
| I-1  | 19.5 | 19.9 | 10.1 | 51%   |
| I-2  | 17.8 | 18.3 | 8.1  | 44%   |
| I-3  | 19.6 | 21.5 | 10.2 | 47%   |
| I-4  | 21.1 | 21.7 | 10.4 | 48%   |
| I-5  | 20.9 | 20.7 | 9.9  | 48%   |
| I-6  | 21.4 | 20.1 | 9.2  | 46%   |
| I-7  | 21.4 | 19.6 | 9.1  | 46%   |
| I-8  | 20.7 | 23.2 | 9.5  | 41%   |
| I-9  | 19.7 | 18.2 | 9    | 49%   |
| I-10 | 21.2 | 17.9 | 10.1 | 56%   |
| I-11 | 19.9 | 19.1 | 9.4  | 49%   |
| I-12 | 20.7 | 26.5 | 12.2 | 46%   |
| I-13 | 18.8 | 21.5 | 10.6 | 49%   |
| I-14 | 18.4 | 20   | 9.9  | 50%   |
| I-15 | 21.3 | 24.3 | 12.9 | 53%   |
| I-17 | 20   | 17.9 | 9.7  | 54%   |
| I-18 | 18.8 | 17.1 | 9.9  | 58%   |
| I-19 | 18.7 | 18.2 | 10.3 | 57%   |
| I-20 | 20.3 | 17.7 | 9.8  | 55%   |
| I-21 | 20.7 | 18   | 9.6  | 53%   |
| I-23 | 20.5 | 24.7 | 10.1 | 41%   |
| I-24 | 19.7 | 28.2 | 13.9 | 49%   |
| I-25 | 19   | 30.1 | 13.5 | 45%   |

Since the requirement "in Hansen solubility parameter, δd is 16 or more, δp is 16 or more and 32 or less, and δH is 60% or less of δp" can be easily satisfied, a) the organic anion is preferably an organic anion represented by General Formula (IA).

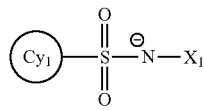

(IA)

In General Formula (IA), $Cy_1$ represents an aryl group or a heteroaryl group.

$X_1$ represents $SO_2R_a$, $SOR_b$, $COR_c$, $PO_3R_d$, or $PO(R_e)(R_f)$. $R_a$, $R_b$, $R_c$, $R_d$, $R_e$, and $R_f$ represent a group selected from the group consisting of an alkyl group, an alkoxy group, an aryl group, a heteroaryl group, and H. $R_a$, $R_b$, $R_c$, $R_d$, $R_e$ or $R_f$ may bond to $Cy_1$ to form a ring. The aryl group and the heteroaryl group represented by $Cy_1$ are identical to the aryl group and the heteroaryl group represented by Cy, and preferred ranges thereof are also identical thereto.

The alkyl group, the alkoxy group, the aryl group, and the heteroaryl group as $R_a$, $R_b$, $R_c$, $R_d$, $R_e$ and $R_f$ in General Formula (IA) are identical to the alkyl group, the alkoxy group, the aryl group, and the heteroaryl group as $R_a$, $R_b$, $R_c$, $R_d$, $R_e$, and $R_f$ in General Formula (I), and preferred ranges thereof are also identical thereto.

The oronic anion represented by General Formula (IA) as a) the organic anion in the present invention is preferably an organic anion represented by General Formula (III) or (IV).

[Counter Cation]

The counter cation ((B) counter cation) that constitutes the specific compound according to the present invention needs to be a cation capable of forming a salt compound with the organic anion having a negative charge present on an aluminum atom or a phosphorus atom through an ionic bond.

The counter cation may be an inorganic cation or an organic cation. As the inorganic cation, alkali metal ions such as a lithium ion, a sodium ion, and a potassium ion, alkali earth metal ions such as a magnesium ion, and a calcium ion, and the like are exemplified.

As the organic cation, organic cations having a positive charge present on a nitrogen atom are exemplified. An ammonium cation, a pyridinium cation, an imidazolium cation, and the like represented by a formula: $N^+(R^{01})(R^{02})(R^{03})(R^{04})$ (here, $R^{01}$, $R^{02}$, $R^{03}$, and $R^{04}$ each independently represent an alkyl group or an aryl group) are also regarded as the organic cation having a positive charge present on a nitrogen atom.

Examples of the ammonium cation include tetramethyl ammonium, tetraethyl ammonium, tetrabutyl ammonium, and the like.

The counter cation is preferably a diaryliodonium cation or a triarylsulfonium cation. The specific compound having a diaryliodonium cation or a triarylsulfonium cation as the counter cation is extremely useful as a photopolymerization initiator.

For example, an iodonium cation represented by Formula (C1) and a cation represented by Formula (C2) are regarded as the diaryliodonium cation and the triarylsulfonium cation respectively.

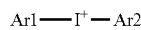
(C1)

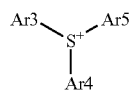
(C2)

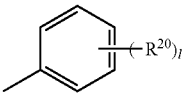
(C3)

In Formulae (C1) and (C2), Ar1, Ar2, Ar3, Ar4, and Ar5 each independently represent a group represented by Formula (C3). In Formula (C3), $R^{20}$ represents an alkyl group, an alkoxy group, a vinyl group, or a halogen atom, and a plurality of $R^{20}$'s may be identical to or different from each other, l represents an integer of 0 to 5.

Specific examples of the diaryliodonium cation include a diphenyliodonium cation, a 4-methoxyphenyl-4-(2-methylpropyl) phenyliodonium cation, a 4-chlorophenyl-4-phenyliodonium cation, a 4-(2-methylpropyl) phenyl-p-tolyliodonium cation, a 4-hexyloxyphenyl-2,4,6-trimethoxyphenyliodonium cation, a 4-hexyloxyphenyl-2,4-diethoxyphenyliodonium cation, a 4-octyloxyphenyl-2,4,6-trimethoxyphenyliodonium cation, and a bis(4-tert-butylphenyl) iodonium cation.

Specific examples of the triarylsulfonium cation include a triphenylsulfonium cation, a bis(4-chlorophenyl)phenylsulfonium cation, a bis(4-chlorophenyl)-4-methylphenylsulfonium cation, a tris(4-chlorophenyl)sulfonium cation, a tris(2,4-dichlorophenyl)sulfonium cation, a bis(2,4-dichlorophenyl)phenylsulfonium cation, and a bis(2,4-dichlorophenyl) 4-methoxyphenylsulfonium cation.

As the counter cation, the counter cation in the cyanine colorant that is used as the infrared absorber is also useful. The counter cation in the cyanine colorant will be described in the description of the infrared absorber described below.

Specific examples of the courier cation will be illustrated below as a cation portion, but the present invention is not limited thereto.

Cation portion

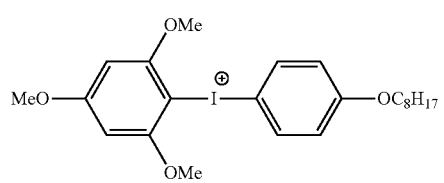
j-1

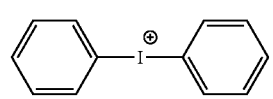
j-2

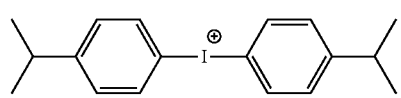
j-3

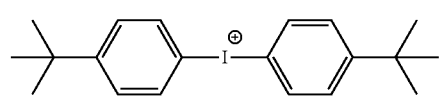
j-4

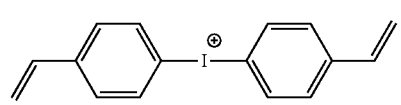
j-5

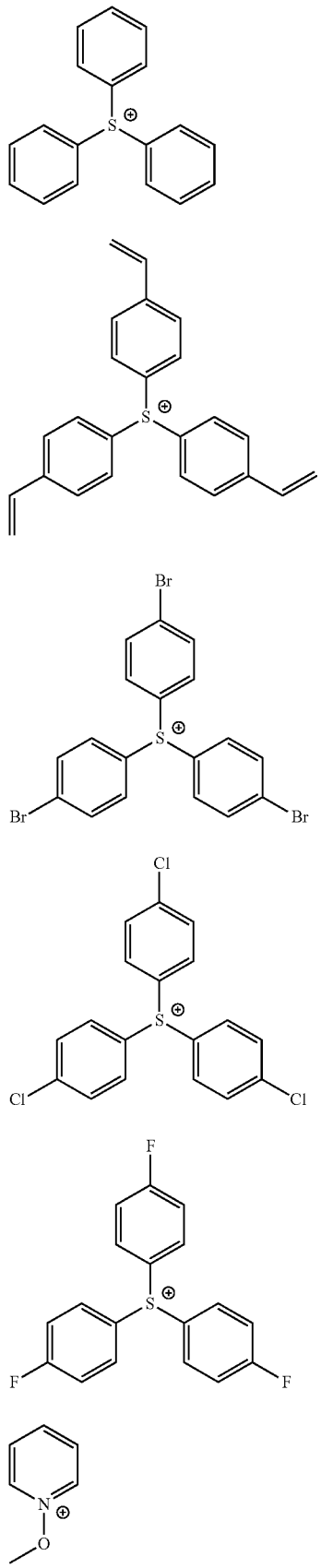

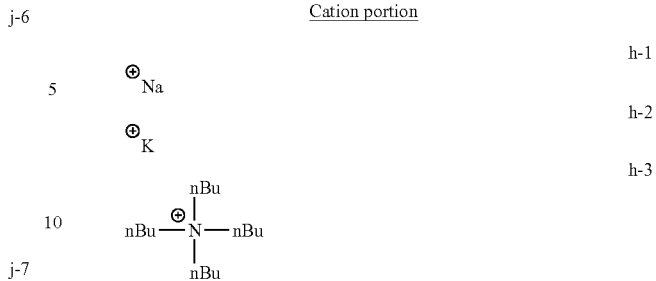

The parameter-regulating compound and the specific compound of the present invention are respectively made of a combination of the anion portion and the cation portion, and the anion portion and the cation portion can be a random combination of structures selected from the respective groups.

Examples of the structure of the specific anion portion and the specific cation portion are as illustrated above, but the present inversion is not limited thereto.

In addition, in examples, the specific compound will be indicated by describing the anion portion and the cation portion like I-1-j-1.

The specific compound according to the presort invention may be used singly or two or more specific compounds may be jointly used. In the second composition of the embodiment of the present invention, the content of the specific compound significantly varies depending on the structure of the specific compound, an intended effect or use, and the like. Generally, the content is preferably 0.1% to 50% by mass, more preferably 0.5% to 40% by mass, and still more preferably 1% to 30% by mass of the total solid content of the composition. In the present specification, the total solid content refers to the total amount of components in the composition of the embodiment of the present invention excluding a volatile component such as a solvent.

The specific compound according to the present invention exhibits a variety of effects. The composition of the embodiment of the present invention containing the specific compound has a favorable thermal and temporal stability (developability after finable thermal aging). This is considered to be attributed to the excellent characteristics of the organic anion that constitutes the specific compound, and, even in the case of being compared to the borate anion described in JP2009-538446A, an effect for significantly improving the thermal and temporal stability is admitted. Therefore, lithographic printing plate precursors to which the composition of the embodiment of the present invention is applied also have excellent thermal and temporal stability.

In addition, the second composition of the embodiment of the present invention that contains the specific compound is excellent in terms of the electron migration efficiency from an infrared absorber to the specific compound that is attributed to exposure to infrared rays or the photothermal conversion efficiency. Therefore, it is considered that a curing reaction called the polymerization or thermal fusion of a polymerizable compound is accelerated and a favorable curing property is exhibited. Therefore, for examide, lithographic printing plates produced from lithographic printing plate precursors to which the composition of the embodiment of the present invention is applied have excellent printing resistance.

Furthermore, in the organic anion that constitutes the specific compound, the sulfonamide anion structure or the sulfonimide anion structure has a negative charge on a nitrogen atom and has a relatively hydrophilic portion and a relatively hydrophobic portion that is present in the vicinity of the relatively hydrophilic portion and has a rigid ring structure as a hydrophobic portion and thus the organic anion has an emulsifying property. Therefore, for example, lithographic printing plate precursors to which the composition of the embodiment of the present invention is applied exhibit favorable on-machine developability.

Furthermore, the organic anion that constitutes the specific compound functions as an acid, and thus, as described below, in the case of jointly using an acid color-developing agent such as a leuco dye in the composition of the embodiment of the present invention, a color-developing image can be formed. The organic anion that constitutes the specific compound is excellent in terms of color-developing performance, and thus, for example, lithographic printing plate precursors to which the composition of the embodiment of the present invention is applied exhibit an excellent plate inspection property.

Furthermore, lithographic printing plate precursors for which a polymerization initiator including well-known $PF_6^-$ as the inorganic anion is jointly used with an acid color-developing agent such as a leuco dye have a problem of the occurrence of ring-shaped color development due to thermal aging. The ring-shaped color development refers to a phenomenon in which fine ring-shaped color development occurs throughout the entire surface of a lithographic printing plate precursor and acts as a drag on a plate inspection operation. Lithographic printing plate precursors for which a polymerization including the organic anion according to the present invention instead of $PF_6^-$ is jointly used with an acid color-developing agent such as a leuco dye have an advantage that ring-shaped color development does not occur due to thermal aging.

In addition, the present invention also relates to a specific compound. As the specific compound, for example, the following compounds are exemplified.

<1> A compound in which an organic anion is represented by General Formula (III) or (IV) and a counter cation is a diaryliodonium cation or a triarylsulfonium cation.

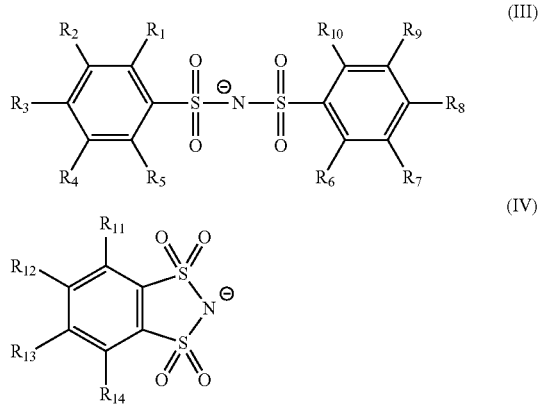

In General Formula (m), $R_1$ to $R_{10}$ each independently represent a hydrogen atom or a monovalent substituent.

In General Formula (IV), $R_{11}$ to $R_{14}$ each independently represent a hydrogen atom or a monovalent substituent.

<2> A compound in which an organic anion is represented by General Formula (III) or (IV) and a counter cation is a counter cation in a cyanine colorant.

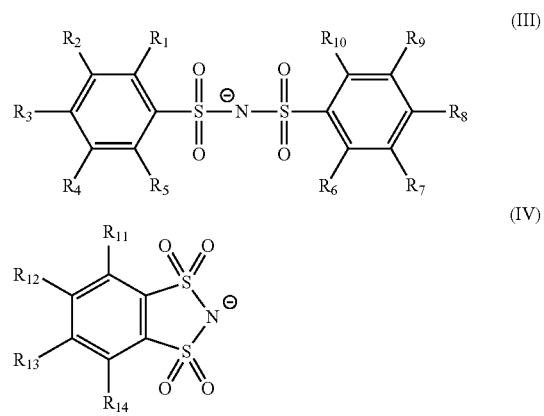

In General Formula (III), $R_1$ to $R_{10}$ each independently represent a hydrogen atom or a monovalent substituent.

In General Formula (IV), $R_{11}$ to $R_{14}$ each independently represent a hydrogen atom or a monovalent substituent.

The respective groups in General Formulae (III) and (IV) are respectively identical to the respective group described above, and preferred ranges thereof are also identical thereto.

The diaryliodonium cation and the triarylsulfonium cation are identical to the diaryliodonium cation and the triarylsulfonium cation described above, and preferred ranges thereof are also identical thereto.

The second composition of the embodiment of the present invention is preferably a composition in any of the following forms (1) to (3).

A composition in a form (1) includes one or more of the specific compound, an infrared absorber, a binder polymer, and a polymer particle and a polymerizable compound.

A composition in a form. (2) includes one or more of the specific compound, an acid color-developing agent, an infrared absorber; a binder polymer, and a polymer particle and a polymerizable compound.

A composition in a form (3) includes one or more of the specific confound, an acid color-developing agent, an infrared absorber, a binder polymer, and a polymer particle, a polymerizable compound, and a polymerization initiator.

The specific compound in the composition of the form (1) is preferably a polymerization initiator in which the counter cation is a diaryliodonium cation or a triarylsulfonium cation.

The specific compound in the composition of the form (2) is preferably a polymerization initiator in which the counter cation is a diaryliodonium cation or a triarylsulfonium cation.

The specific compound in the composition of the form (3) is preferably an additive in which foe counter cation is an alkali metal ion, an alkali earth metal ion, or an organic cation having a charge on a nitrogen atom.

Hereinafter, components that the first and second compositions of the embodiment of the present invention (hereinafter; also collectively referred to as "the composition of the embodiment of the present invention") may have swill be described.

[Infrared Absorber]

The composition of the embodiment of the present inversion preferably contains an infrared absorber. The infrared absorber has a function of migrating electron and/or migrating energy to a polymerization initiator or the like by being excited by infrared rays. In addition, the infrared absorber has a function of converting the absorbed infrared rays to heat. Tire infrared absorber preferably has the maximum absorption in a wavelength range of 750 to 1,400 nm. As the infrared absorber; a dye or a pigment is exemplified, and a dye is preferably used.

As the dye, it is possible to use a commercially available dye and a well-known dye described in publications, for example, "Dye Handbooks" (edited by the Society of Synthetic Organic Chemistry, Japan and published on 1970). Specific examples thereof include dyes such as an azo dye, a metal complex azo dye, a pyrazolone azo dye, a naphthoquinone dye, an anthraquinone dye, a phthalocyanine dye, a carbonium dye, a quinoneimine dye, a methine dye, a cyanine dye, a squarylium colorant, a pyrylium salt, and a metal thiolate complex.

Among these dyes, a cyanine colorant, a squarylium colorant, and a pyrylium salt are preferred, a cyanine colorant is more preferred, and an indolenine cyanine colorant is particularly preferred.

In addition, as the infrared absorber, it is possible to use a compound described in Paragraph 0021 of EP1736312A and a compound described in Paragraphs 0069 to 0080 of WO2016/027886A.

Specific examples of the cyanine colorant include a compound described in Paragraphs 0017 to 0019 of JP2001-133969A, a compound described in Paragraphs 0016 to 0021 of JP2002-023360A and Paragraphs 0012 to 0037 of JP2002-040638A, preferably a compound described in Paragraphs 0034 to 0041 of JP2002-278057A and Paragraphs 0080 to 0086 of JP2008-195018A, and particularly preferably a compound described in Paragraphs 0035 to 0043 of JP2007-090850A.

In addition, it is also possible to preferably use a compound described in Paragraphs 0008 and 0009 of JP1993-005005A (JP-H05-005005A) and Paragraphs 0022 to 0025 of JP2001-222101A.

As the pigment, a compound described in Paragraphs 0072 to 0076 of JP2008-195018A is preferred.

The cyanine colorant may contain the organic anion according to the present invention as a counter ion that neutralizes a charge. In this case, the cyanine colorant corresponds to the specific compound according to the present invention.

The infrared absorber may be used singly or two or more infrared absorbers may be jointly used.

The infrared absorber can be added to the composition in a random amount. The content of the infrared absorber is preferably 0.05% to 30% by mass, more preferably 0.1% to 20% by mass, and still more preferably 0.2% to 10% by mass of the total solid content of the composition.

[Polymerizable Compound]

The composition of the embodiment of the present invention preferably contains a polymerizable compound. The polymerizable compound may be, for example, a radical polymerizable compound or a cationic polymerizable compound, but is preferably an addition polymerizable compound having at least one ethylenically unsaturated bond (ethylenically unsaturated compound). The ethylenically unsaturated compound is preferably a compound having at feast one terminal ethylenically unsaturated bond and more preferably a compound having two or more terminal ethylenically unsaturated bonds. The polymerizable compound may have a chemical form, foe example, a monomer, a prepolymer, that is, a dimer, a trimer, or an oligomer, or a mixture thereof.

Examples of the monomer include unsaturated carboxylic acids (for example, acrylic acid, methacrylic acid, itaconic acid, crotonic acid, isocrotonic acid, and maleic acid), esters thereof, and amides thereof and esters of unsaturated carboxylic acids and polyvalent amine compounds and amides of unsaturated carboxylic acids and polyhydric alcohol confounds are preferably used fir addition, addition reaction product between unsaturated carboxylic acid esters or amides having nucleophilic substituents such as hydroxy poops, amino groups, or mercapto groups and monofunctional or polyfunctional isocyanates or epoxies, dehydration condensation reaction product with monofunctional or polyfunctional caboxylic acids, and the like are also preferably used. In addition, addition reaction product between unsaturated carboxylic acid esters or amides having electrophilic substituents such as isocyanate groups and epoxy groups and monofunctional or polyfunctional alcohols, amines, or thiols, furthermore, substitution reaction product between unsaturated carboxylic acid esters or amides having dissociable substituents such as halogen atoms and tosyloxy groups and monofunctional or polyfunctional alcohols, amines, or thiols are also preferred. In addition, as additional examples, compound groups obtained by substituting the unsaturated carboxylic acid with unsaturated phosphonic acids, styrene, vinyl ethers, or the like can also be used. These compounds are described in JP2006-508380A, JP2002-287344A, JP2008-256850A, JP2001-342222A, JP1997-179296A (JP-H09-179296A), JP1997-179297A (JP-H09-179297A), JP1997-179298A (JP-H09-179298A), JP2004-294935A, JP2006-243493A, JP2002-278129A, JP2003-064130A, JP2003-280187A, JP1998-333321A (JP-H10-333321A), and the like.

As specific examples of monomers of esters of polyhydric alcohol compounds and unsaturated carboxylic acids, examples of acrylic acid esters include ethylene glycol diacrylate, 1,3-butanediol diacrylate, tetramethylene glycol diacrylate, propylene glycol diacrylate, trimethylolpropane triacrylate, hexanediol diacrylate, tetraethylene glycol diacrylate, pentaerythritol tetraacrylate, sorbitol triacrylate, isocyanuric acid ethylene oxide (EO)-modified triacrylate, polyester acrylate oligomers, and the like. Examples of methacrylic acid esters include tetramethylene glycol dimethacrylate, neopentyl glycol dimethacrylate, trimethylolpropane trimethacrylate, ethylene glycol dimethacrylate, pentaerythritol trimethacrylate, bis[p-(3-methacryloxy-2-hydroxypropoxy)phenyl] dimethyl methane, bis[p-(methacryloxyethoxy)phenyl] dimethyl methane, and the like. In addition, specific examples of monomers of amides of polyvalent amine compounds and unsaturated carboxylic acid include methylene bisacrylamide, methylene bismethacrylamide, 1,6-hexamethylene bisacrylamide, 1,6-hexamethylene bismethacrylamide, diethylenetriamine trisacrylamide, xylylene bisacrylamide, xylylene bismethacrylamide, and the like.

In addition, urethane-based addition polymerizable compounds produced using an addition reaction between an isocyanate and a hydroxy group are also preferred, and specific examples thereof include vinyl urethane compounds having two or more polymerizable vinyl groups in one molecule obtained by adding vinyl monomers having a hydroxy group represented by Formula (M) to a polyisocyanate compound having two or more isocyanate groups in one molecule which is described in, for example, JP1973-041708B (JP-S48-041108B).

$$CH_2=C(R^{M4})COOCH_2CH(R^{M5})OH \quad (M)$$

In Formula (M), $R^{M4}$ and $R^{M5}$ each independently represent a hydrogen atom or a methyl group.

In addition, urethane acrylates described in JP1976-037193A (JP-S51-037193A), JP1990-032293B (JP-H02-032293B), JP1990-016765B (JP-H02-016765B), JP2003-344997A, and JP2006-065210A, methane compounds having ethylene oxide-based skeletons described in JP1983-049860B (JP-S58-049860B), JP1981-017654B (JP-S56-017654B), JP1987-039417B (JP-S62-039417B), JP1987-039418B (JP-S62-039418B), JP2000-250211A, and JP2007-094138A, and urethane compounds having hydrophilic groups described in U.S. Pat. No. 7,153,632B. JP1996-505958A (JP-H08-505958A), JP2007-293221A, and JP2007-293223A are also preferred.

The details of the structures of the polymerizable compound and the method for using the polymerizable compound such as whether to use the polymerizable compound singly or jointly and the amount of the polymerizable compound added can be randomly set m consideration of the final applications and the like of the composition.

The content of the polymerizable compound is preferably in a range of 5% to 75% by mass, more preferably in a range of 10% to 70% by mass, and still more preferably in a range of 15% to 60% by mass of the total solid content of the composition.

[Polymerization Initiator]

The composition of the embodiment of the present invention preferably contains a polymerization initiator. The polymerization initiator is a compound that generates a polymerization-initiating species such as a radical or a cation with the energy of heat, light, or both, and Et is possible to appropriately select from a well-known thermopolymerization initiator, a compound having a bond with a small bond dissociation energy, a photopolyfiim ration initiator, and the like and use it.

The polymerization intiator is preferably an infrared-sensitive polymerization initiator. In addition, the polymerization initiator is preferably a radical polymerization initiator.

Examples of the radical polymerization initiator include an organic halide, a carbonyl compound, an azo compound, an organic peroxide, a metallocene compound, an azide compound, a hexaarylbiimidazole compound, a disulfone compound, an oxime ester compound, and an onium salt compound.

As the oronic halide, for example, a compound described in Paragraphs 0022 and 0023 of JP2008-195018A is preferred.

As the carbonyl compound, for example, a compound described in Paragraph 0024 of JP2008-195018A is preferred.

As the azo compound, for example, an azo compound described in JP1996-108621A (JP-H08-108621A) is exemplified.

As the organic peroxide, for example, a compound described in Paragraph 0025 of JP2008-195018A is preferred.

As the metallocene compound, for example, a confound described in Paragraph 0026 of JP2008-195018A is preferred.

As the azide compound, for example, a compound such as 2,6-bis(4-azidobenzylidene)-4-methylcyclohexanone is exemplified.

As the hexaarylbiimidazole compound, for ample, a compound described in Paragraph 0027 of JP2008-195018A is preferred.

As the disulfone compound, for example, a compound described in each of JP1986-166544A (JP-S61-166544A) and JP2002-328465A exemplified.

As the oxime ester compound, for example, a confound described in Paragraphs 0028 to 0030 of JP2008-19S018A is preferred.

As the polymerization initiators, from the viewpoint of foe curing property, an oxime ester and an onium salt are more preferably exemplified, and onium salts such as an iodonium salt a sulfonium salt, and an azinium salt are still more preferably exemplified. In the case of applying the composition of the embodiment of the present invention to a lithographic printing plate precursor, an iodonium salt and a sulfonium salt are particularly preferred. Specific examples of the iodonium salt and the sulfonium salt will be described below, but the present invention is not limited thereto.

An example of the iodonium salt is preferably a diphenyl iodonium salt, particularly, preferably a diphenyl iodonium salt having an electron-donating group as a substitutent, for example, a diphenyl iodonium salt substituted with an alkyl group or an alkoxyl group, and preferably an asymmetric diphenyl iodonium salt specific examples thereof include diphenyliodonium=hexafluorophosphate, 4-methoxyphenyl-4-(2-methylpropyl) phenylliodonium=hexafluorophosphate, 4-(2-methylpropyl) phenyl-p-tolyloidonium=hexafluorophosphate, 4-hexyloxyphenyl-2,4,6-trimethoxyphenyl iodonium=hexafluorophosphate, 4-hexyloxyphenyl-2,4-diethoxyphenyl iodonium=tetrafluoroborate, 4-octyloxyphenyl-2,4,6-trimethoxyphenyl iodonium=1-perfluorobutane sulfonate, 4-octyloxyphenyl-2,4,6-trimethoxyphenyliodonium=4hexafluorophosphate, and bis (4-t-butylphenyl)iodonium=hexafluorophosphate.

The sulfonium salts are preferably triarylsulfonium salts, particularly preferably triarylsulfonium salts having an election-attracting group as a substituent, for example, triarylsulfonium salts in which at least some of groups on the aromatic ring are substituted with a halogen atom, and still more preferably triarylsulfonium salts in which the total number of substituting halogen atoms on the aromatic ring is four or greater. Specific examples thereof include triphneylsulfonium=hexafluorophosphate, triphenylsulfonium=benzoyl formate, bis(4-chlorophenyl) phenylsulfonium=benzoyl formate, bis(4-chlorophenyl)-4-methylphenylsulfonium=tetrafluoroborate, tris(4-chlorophenyl)sulfonium=3,5-bis(methoxycarbonyl) benzenesulfonate, tris(4-chlorophenyl) sulfonium=hexafluorophosphate, and tris(2,4-dichlorophenyl)sulfonium=hexafluorophosphate.

The polymerization initiator may contain an organic anion according to the present invention as an anion. In this case, the polymerization initiator corresponds to the specific compound according to the present invention.

The polymerization initiator may be used singly or two or more polymerization initiators may be jointly used.

The content of the polymerization initiator is preferably 0.1% to 50% by mass, more preferably 0.5% to 30% by mass, and still more preferably 0.8% to 20% by mass of the total solid content of the composition.

[Binder Polymer]

In a case in which the composition of the embodiment of the present invention preferably contains a binder polymer. The binder polymer is preferably a polymer having a film property, and it is possible to preferably use well-known binder polymers that are used in the composition. Among them, as the binder polymer, a (meth)acrylic resin, a polyvinyl acetal resin, and a polyurethane resin are preferred.

In a casein which the composition of the embodiment of the present invention is applied to an image-recording layer in a lithographic printing plate precursor, as the binder polymer, it is possible to preferably use well-known binder polymers that can be used in the image-recording layer in the lithographic printing plate precursor. As an example, a binder polymer that is used for an on-machine development-type lithographic printing plate precursor (hereinafter, also referred to as the binder polymer for on-machine development) will be described in detail.

As the binder polymer for on-machine development, a binder polymer having an alkylene oxide chain b preferred. The binder polymer having an alkylene oxide chain may have a polyalkylene oxide) portion in a main chain or in a side chain. In addition, the binder polymer may be a graft polymer having polyalkylene oxide) in a side drain or a block copolymer of a block constituted of a poly(alkylene oxide)-containing repeating unit and a block constituted of an (alkylene oxide)-non-containing repeating unit.

In the case of having a polyalkylene oxide) portion in the main chain, the binder polymer is preferably a polyurethane resin. As a polymer in the main chain in a case in which the tender polymer has a polyalkylene oxide) portion in the side chain, a (meth)acrylic resin, a polyvinyl acetal resin, a polyurethane resin, a polyurea resin, a polyimide resin, a polyamide resin, an epoxy resin, a polystyrene resin, a novolac-type phenol resin, a polyester resin, synthetic rubber, and natural rubber are exemplified, and, particularly, a (meth)acrylic resin is preferred.

The alkylene oxide is preferably alkylene oxide having 2 to 6 carbon atoms and particularly preferably ethylene oxide or propylene oxide.

The number of times of repetition of the alkylene oxide in the polyalkylene oxide) portion is preferably 2 to 120, more preferably 2 to 70, and still more preferably 2 to 50.

In a case in which the comber of times of repetition of the alkylene oxide is 120 or less, neither the printing resistance against wear nor the printing resistance against the ink-receiving property degrades, which is preferable.

The polyalkylene oxide) portion is preferably contained in a form of a structure represented by Formula (AO) as the side chain of the tender polymer and more preferably contained in a form of the structure represented by Formula (AO) as the side chain of the (meth)acrylic resin.

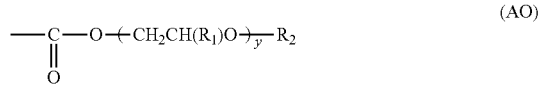

(AO)

In Formula (AO), y represents 2 to 120, $R_1$ represents a hydrogen atom or an alkyl group, and $R_2$ represents a hydrogen atom or a monovalent organic group.

The monovalent organic group is preferably an alkyl group having 1 to 6 carbon atoms. Specific examples thereof include a methyl group, an ethyl group, an n-propyl group, an isopropyl group, an n-butyl group, a sec-butyl group, an isobutyl group, a tert-butyl group, an n-pentyl group, an isopentyl group, a neopentyl group, an n-hexyl group, an isohexyl group, a 1,1-dimethylbutyl group, a 2,2-dimethylbutyl group, a cyclopentyl group, and a cyclohexyl group.

In Formula (AO), y is preferably 2 to 70 and more preferably 2 to 50. $R_1$ is preferably a hydrogen atom or a methyl group and particularly preferably a hydrogen atom. $R_2$ is particularly preferably a hydrogen atom or a methyl group.

The binder polymer may have a crosslinking property in order to improve the membrane hardness of an image area. In order to provide a crosslinking property to the polymer, a crosslinking functional group such as an ethylenically unsaturated bond may be introduced to a main chain or a side chain of a polymer. The crosslinking functional group may be introduced by copolymerisation or may be introduced fry a polymer reaction.

Examples of a polymer having an ethylenically unsaturated bond in the main chain of the molecule include poly-1,4-butadiene, poly-1,4-isoprene, and the like.

Examples of a polymer having an ethylenically unsaturated bond in the side chain of the molecule include polymers that are an ester or an of acrylic acid or methacrylic acid and in which a residue (R in —COOH or —CONHR) of the ester or the amide is a polymer having an ethylenically unsaturated bond.

Examples of the residue (the R) having an ethylenically unsaturated bond can include —$(CH_3)_n CR^{14}$=$CR^{24}R^{14}$, —$(CH_2O)_n CH_2 CR^{14}$=$CR^{24}R^{34}$, —$(CH_2 CH_2O)_n CH_2 CR^{14}$=$CR^{24}R^{34}$, —$(CH_2)_n NH$—CO—O—$CH_2 CR^{14}$=$CR^{24}R^{34}$, —$(CH_2)_n$—O—CO—$CR^{14}$=$CR^{24}R^{34}$, and —$(CH_2 CH_2O)_2$—$X^A$ (in the formulae, $R^{41}$ to $R^{43}$ each independently represent a hydrogen atom, a halogen atom, an alkyl group having 1 to 20 carbon atoms, an aryl group, an alkoxy group, or an aryloxy group, and $R^{41}$ and $R^{42}$ or $R^{43}$ may be bonded to each other to form a ring, n represents an integer of 1 to 10. $X^A$ represents a dicyclopentadienyl residue.).

Specific examples of an ester residue include —$CH_2CH$=$CH_2$, —$CH_3CH_2O$—$CH_2CH$=$CH_3$, —$CH_2C(CH_3)$=$CH_2$, —$CH_2CH$=$CH$—$C_6H_5$, —$CH_2CH_2OCOCH$=$CH$—$C_6H_5$, —$CH_2CH_2$—$NHCOO$—$CH_2CH$=$CH_2$, and —$CH_2CH_2O$—X (in the formula, X represents a dichyclopentadienyl residue.).

Specific examples of an amide residue include —$CH_2CH$=$CH_2$, —$CH_2CH_2$—Y (in the formula, Y represents a cyclohexene residue.), and —$CH_2CH_2$—OCO—CH=$CH_2$.

The binder polymer having a crosslinking property is cored as follows: for example, a free radical (a polymerization initiation radical or a growth radical in a polymerization process of a polymerizable compound) is added to the crosslinking functional group, addition polymerization occurs between polymers directly or through the polymerization chain of the polymerizable compound, and a crosslink is formed between the polymer molecules, whereby the polymer is cured. Alternatively, an atom in the polymer (for trample, a hydrogen atom on a carbon atom adjacent to the crosslinking functional group) is pulled off by a free radical, polymer radicals are generated, and the polymer radicals are bonded to each other, whereby a crosslink is formed between the polymer molecules, and the polymer is cured.

The content of the crosslinking group in the binder polymer (the content of an unsaturated double bond that is radical polymerizable by iodimetry) is preferably 0.1 to 10.0 mmol, more preferably 1.0 to 7.0 mmol, and still more preferably 2.0 to 5.5 mmol per gram of the binder polymer from the viewpoint of a favorable sensitivity and a favorable storage stability.

Hereinafter, specific examples 1 to 11 of the binder polymer will be illustrated, but the present invention is not limited thereto. In the following exemplary compounds, numerical values described together with individual repeating units (numerical values described together with main chain repealing units) represent the molar percentages of the repealing units. Numerical values described together with side chain repeating units represent the number of times of repetition of the repeating portions. In addition, Me represents a methyl group, Et represents an ethyl group, and Ph represents a phenyl group.
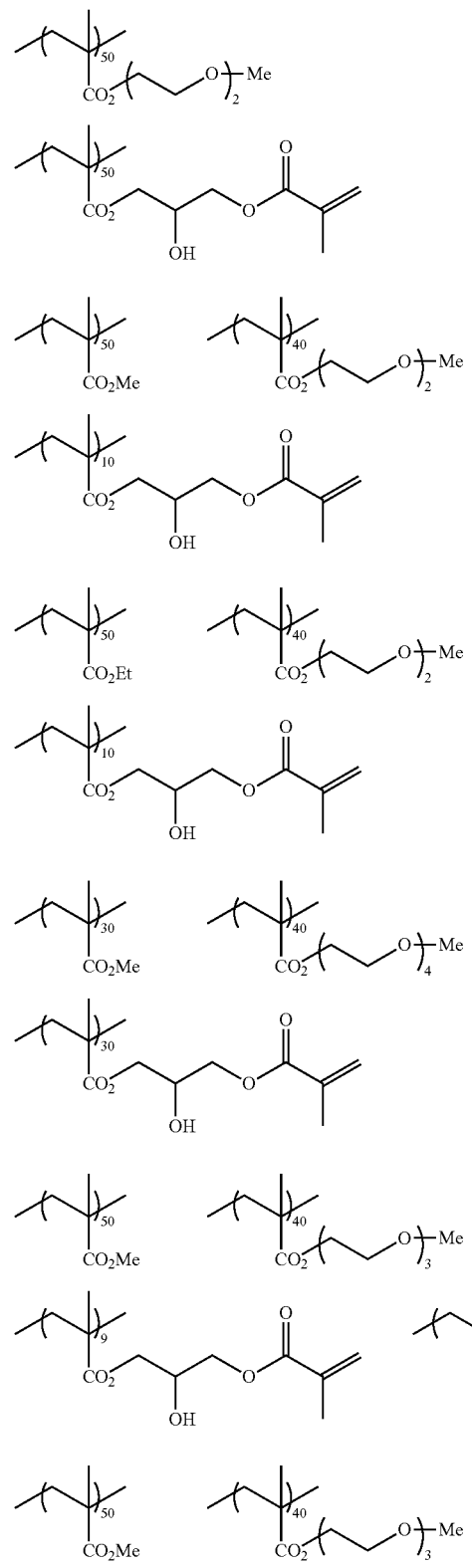
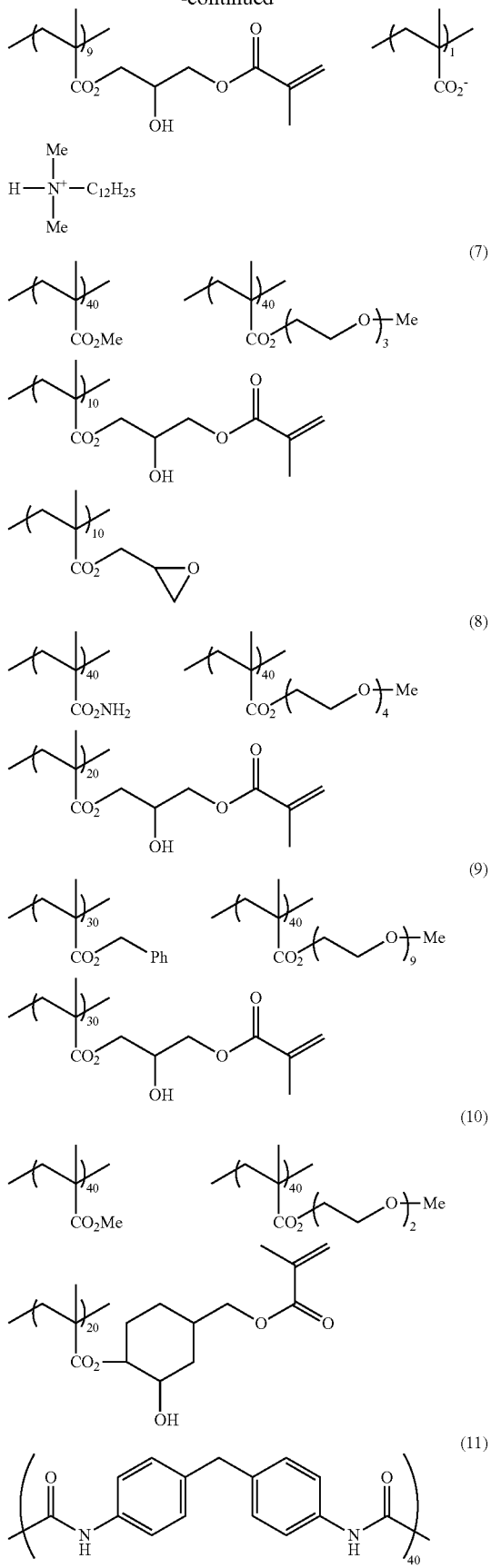

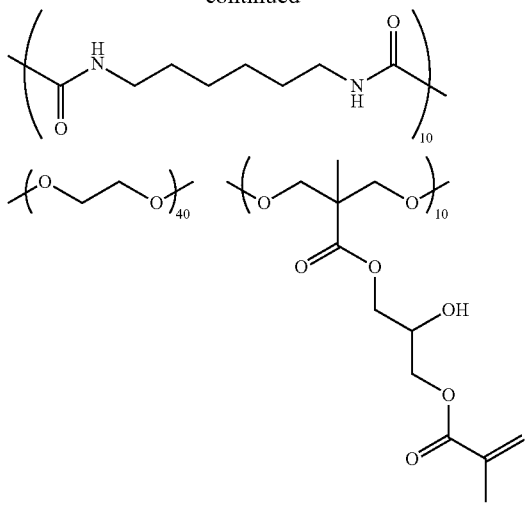

Regarding the molecular weight of the binder polymer, the weight-average molecular weight (Mw) as a polystyrene equivalent value by a GPC method is 2,000 or more, preferably 5,000 or more, and more preferably 10,000 to 300,000.

In addition, in the present invention, an oligomer refers to a substance having Mw of 800 or more and less than 2,000, and a polymer refers to a substance having Mw of 2,000 or more.

If necessary, it is possible to jointly use a hydrophilic polymer such as polyacrylic acid or polyvinyl alcohol described in JP2008-195018A. In addition, it is also possible to jointly use a lipophilic polymer and a hydrophilic polymer.

In a case in which the composition of the embodiment of the present invention is applied to the image-recording layer in the lithographic printing plate precursor, the binder polymer may be present as a polymer that functions as a binder of the respective components or may be present in a particle shape in the composition. In a case in which the binder polymer is present in a particle shape, the volume average primary particle diameter is preferably 10 to 1,000 nm, more preferably 20 to 300 nm and still mote preferably 30 to 120 nm.

In the present invention, the volume average primary particle diameter is obtained by capturing an electron micrograph of particles, measuring the particle diameters of a tonal of 5,000 particles on the photograph, and computing the arithmetical average value.

For a non-spherical particle, the particle diameter value of a spherical particle having the same particle area as the particle area on the photograph was measured as the particle diameter (circle-equivalent diameter).

The above-described method for measuring the volume average primary particle diameter shall apply to the particle of any substances other than the binder polymer which is present in a particle shape as long as there is no special description.

The binder polymer may be used singly or two or mote binder polymers may be jointly used.

The binder polymer can be added to the composition in a random amount. The content of the binder polymer can be appropriately selected depending on the application or the like of the composition of the embodiment of the present invention, but is preferably 1% to 90% by mass and more preferably 5% to 80% by mass of the total solid coded of the composition.

[Add Color-Developing Agent]

The composition of the embodiment of the present invention may contain an acid color-developing agent. The acid color-developing agent is a compound having a property of developing color by receiving an electron-receiving compound (for example, a proton such as an acid). The acid color-developing agent is preferably a colorless compound which has a partial skeleton of lactone, lactam, a sultone, a spiropyran, an ester, an amide, or the like and in which these partial skeletons are ring-opened or cleaved in a case in which the compound comes into contact with an electron-receiving compound.

Examples of the above-described acid color-developing agent include phthalides such as 3,3-bis(4-dimethylaminophenyl)-6-dimethylaminophthalide (referred to as "crystal violet lactone"), 3,3-bis(4-dimethylaminophenyl) phthalide, 3-(4-dimethylaminophenyl)-3-(4-diethylamino-2-methylphenyl)-6-dimethylaminophthalide, 3-(4-dimethylaminophenyl)-3-(1,2-dimethylindol-3-yl) phthalide, 3-(4-dimethylaminophenyl)-3-(2-methylindol-3-yl) phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, 3-(4-dimethylaminophenyl)-3-(1-methylpyrrole-3-yl)-6-dimethylaminophthalide, 3,3-bis[1,1-bis(4-dimethylaminophneyl) ethylene-2-yl]-4,5,67-tetrachlorophthalide, 3,3-bis[1,1-bis(4-pyrrolidinophenyl) ethylene-2-yl]-4,5,6,7-tetrabromophthalide, 3,3-bis[1-(4-dimethylaminophenyl)-1-(4-methoxyphenyl) ethylene-2-yl]-4,5,6,7-tetrachlorophthalide, 3,3-bis[1-(4-pyrrolidinophenyl)-1-(4-methoxyphenyl) ethylene-2-yl]-4,5,6,7-tetrachlorophthalide, 3-[1,1-di(1-ethyl-2-methylindol-3-yl) ethylene-2-yl]-3-(4-diethylaminophenyl)phthalide, 3-[1,1-di(1-ethyl-2-methylindol-3-yl) ethylene-2-yl]-3-(4-N-ethyl-N-phenylaminophenyl) phthalide, 3-(2-ethoxy-4-diethylaminophenyl)-3-(1-n-octyl-2-methylindol-3-yl)-phthalide, 3,3-bis(1-n-octyl-2-methylindol-3-yl)-phthalide, and 3-(2-methyl-diethylaminophenyl)-3-(1-n-octyl-2-methylindol-3-yl)-phthalide, 4,4-bis-dimethylaminobenzhydrin benzyl ether, N-halophenyl-leucoauramine, N-2,4,5-trichlorophenyleucoauramine, rhodamine-B-anilinolactam, rhodamine-(4-nitroanilino) lactam, rhodamine-B-(4-chloroanilino) lactam 3,7-bis(diethylamino)-10-benzoylphenoxazine, benzoyl leuco methylene blue, 4-nitrobenzoyl methylene blue, fluoranes such as 3,6-dimethyoxyfluoran, 3-dimethylamino-7-methoxyfluoran, 3-diethylamino-6-methoxyfluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-N-cyclohexyl-N-n-butylamino-7-methylfluoran, 3-diethylamino-7-dibenzylaminofluoran, 3-diethylamino-7-octylaminofluoran, 3-diethylamino-7-di-n-hexylaminofluoran, 3-diethylamino-7-anilinofluoran, 3-diethylamino-7-(2'-fluorophenylamino) fluoran, 3-diethylamino-7-(2'-chlorophenylamino)fluoran, 3-diethylamino-7-(3'-chlorophenylamino)fluoran, 3-diethylamino-7-(2',3'-dichlorophenylamino)fluoran, 3-diethylamino-7-(3'-trifluoromethylphenylamino)fluoran, 3-di-n-butylamino-7-(2'-fluorophenylamino)fluoran, 3-di-n-butylamino-7-(2'-chlorophenylamino)fluoran, 3-N-isopentyl-N-ethylamino-7-(2'-chlorophenylamino)fluoran, 3-N-n-hexyl-N-ethylamino-7-(2'-chlorophenylamino) fluorane, 3-diethylamino-6-chloro-7-anilinofluorane, 3-di-n- butylamino-6-chloro-7-anilinofluorane, 3-diethylamino-6-methoxy-7-anilinofluorane, 3-di-n-butylamino-6-ethoxy-7-anilinofluorane, 3-pyrrolidino-6-methyl-7-anilinofluorane, 3-piperidino-6-methyl-7-anilinofluorane, 3-morpholino-6-methyl-7-anilinofluorane, 3-dimethylamino-6-methyl-7-anilinofluorane, 3-diethylamino-6-methyl-7-anilinofluorane, 3-di-n-butylamino-6-methyl-7-anilinofluorane, 3-di-n-pentylamino-6-methyl-7-anilinofluorane, 3-N-ethyl-N-methylamino-6-methyl-7-anilinofluorane, 3-Nn-propyl-N-methylamino-6-methyl-7-anilinofluorane, 3-N-n-propyl-N-ethylamino-6-methyl-7-anilinofluorane, 3-N-n-butyl-N-methylamino-6-methyl-7-anilinofluorane, 3-N-n-butyl-N-ethylamino-6-methyl-7-anilinofluorane, 3-N-isobutyl-N-methylamino-6-methyl-7-anilinofluorane, 3-N-isobutyl-N-ethylamino-6-methyl-7-anilinofluorane, 3-N-isopentyl-N-ethylamino-6-methyl-7-anilinofluorane 3-N-n-hexyl-N-methylamino-6-methyl-7-anilinofluorane, 3-N-cyclohexyl-N-ethylamino-6-methyl-7-anilinofluorane, 3-N-cyclohexyl-N-n-propylamino-6-methyl-7-anilinofluorane, 3-N-cyclohexyl-N-n-butylamino-6-methyl-7-anilinofluorane, 3-N-cyclohexyl-N-n-hexylamino-6-methyl-7-anilinofluorane, 3-N-cyclohexyl-N-n-octylamino-6-methyl-7-anilinofluorane, 3-N-(2'-methoxyethyl)-N-methylamino-6-methyl-7-anilinofluorane, 3-N-(2'-methoxyethyl)-N-ethylamino-6-methyl-7-anilinofluorane, 3-N-(2'-methoxyethyl)-N-isobutylamino-6-methyl-7-anilinofluorane, 3-N-(3'-ethoxypropyl)-N-methylamino-6-methyl-7-anilinofluorane, 3-N'-ethoxyethyl)-N-ethylamino-6-methyl-7-anilinofluorane, 3-N-(3'-methoxypropyl)-N-methylamino-6-methyl-7-anilinofluorane, 3-N-(3'-methoxypropyl)-N-ethylamino-6-methyl-7-anilinofluorane, 3-N-(3'-ethoxypropyl)-N-methylamino-6-methyl-7-anilinofluorane, 3-N-(3'-ethoxypropyl)-N-ethylamino-6-methyl-7-anilinofluorane, 3-N-(2'-tetrahydrofurfuryl)-N-ethylamino-6-methyl-7-anilinofluorane, 3-N-(4'-methylphenyl)-N-ethylamino-6-methyl-7-anilinofluorane, 3-diethylamino-6-ethyl-7-anilinofluorane, 3-diethylamino-6-methyl-7-(3'-methylphenylamino)fluorane, 3-diethylamino-6-methyl-7-(2',6'-dimethylphenylamino)fluorane, 3-di-n-butylamino-6-methyl-7-(2',6'-dimethylphenylamino)fluorane, 3-di-n-butylamino-7-(2',6'-dimethylphenylamino)fluorane, 2,2-bis[4'-(3-N-cyclohexyl-N-methylamino-6-methylfluorane)-7-ylaminophneyl]propane, 3-[4'-(4-phenylaminophenyl) aminophenyl]amino-6-methyl-7-chlorofluorane, and 3-[4'-(dimethylaminophenyl)]amino-5,7-dimethylfluoran, phthalides such as 3-(2-methyl-4-diethylaminophenyl)-3-(1-ethyl-2-methylindol-3-yl)-4-azaphthalide, 3-(2-n-propoyxcarbonylamino-4-di-n-propylaminophenyl)-3-(1-ethyl-2-methylindol-3-yl)-4-azaphthalide, 3-(2-methylamino-4-di-n-propylaminophenyl)-3-(1-ethyl-2-methylindol-3-yl)-4-azaphthalide, 3-(2-methyl-4-di-n-hexylaminophenyl)-3-(1-n-octyl-2-methylindole-3-yl)-4,7-diazaphthalide, 3,3-bis(2-ethoxy-4-diethylaminophenyl)-4-azaphthalide, 3,3-bis(1-n-octyl-2-methylindole-3-yl)-4-azaphthalide, 3-(2-ethoxy-4-diethylaminophenyl)-3-(1-ethyl-2-methylindole-3-yl)-4-azaphthalide, 3-(2-ethoxy-4-diethylaminophenyl)-3-(1-octyl-2-methylindole-3-yl)-4 or 7-azaphthalide, 3-(2-ethoxy-4-diethylaminophenyl)-3-(1-ethyl-2-methylindol-3-yl)-4 or 7-azaphthalide, 3-(2-hexyloxy-4-diethylaminophenyl)-3-(1-ethyl-2-methylindol-3-yl)-4 or 7-azaphthalide 3-(2-ethoxy-4-diethylaminophenyl)-3-(1-ethyl-2-phenylindol-3-yl)-4 or 7-azaphthalide; 3-(2-butoxy-4-diethylaminophenyl)-3-(1-ethyl-2-phenylindol-3-yl)-4 or 7-azaphthalide, 3-methyl-spiro-dinapthopyran, 3-ethyl-spiro-dinaphthopyran, 3-phenyl-spiro-dinaphthopyran, 3-benzyl-spiro-dinaphthopyran, 3-methyl-naphtho-(3-methoxybenzo)spiropyran, 3-propyl-spiro-dinaphthopyran-3,6-bis(dimethylamino)fluorene-9-spiro-3'-(6'-dimethylamino)phthalide, and 3,6-bis(diethylamino) fluoren-9-spiro-3'-(6'-dimethylamino)phthalide, furthermore, 2'-anilino-6'-(N-ethyl-N-isopentyl)amino-3'-methylspiro(isobenzofuran-1 (3H), 9'-(9H) xanthen-3-one, 2'-anilino-6'-(N-ethyl-N-(4-methylphenyl))amino-3'-methylspiro[isobenzofuran-1 (3H), 9'-(9H) xanthene]-3-one, 3'-N,N-dibenzylamino-6'-N,N-diethylaminospiro[isobenzofuran-1 (3H), 9'-(9H) xanthene]-3-one, 2'-(N-methyl-N-phenyl)amino-6'-(N-ethyl-N-(4-methylphenyl))aminospiro [isobenzofuran-1 (3H), 9'-(9H) xanthene]-3-one, and the like are exemplified.

The acid color-developing agent is preferably at least one compound selected from the group consisting of a spiropyran compound, a spirooxazine compound, a spirolactone confound, and a spirolactam compound.

The hue of the colorant after color development is preferably green, bloc, or black from the viewpoint of visibility.

As the acid color-developing agent, it is also possible to use commercially available products. For example, ETAC, RED 500, RED 520, CVL, S-205, BLACK 305, BLACK 400, BLACK 100, BLACK 500, H-7001, GREEN 300, NIRBLACK 78, BLUE 220, H-3035, BLUE 203, ATP, H-1046, H-2114 (all manufactured by Fukui Yamada Chemical Co., Ltd.), ORANGE-DCF, Vermilion-DCF, PINK-DCF, RED-DCF, BLMB, CVL, GREEN-DCF, TH-107 (all manufactured by Hodogaya Chemical Co., Ltd.), ODB, ODB-2, ODB-4, ODB-250, ODB-BlackXV, Blue-63, Blue-502, GN-169, GN-2, Green-118, Red40, Red-8 (all manufactured by Yamamoto Chemicals Inc.), crystal violet lactone (manufactured by Tokyo Chemical Industry Co., Ltd.), and the like. Among these commercially available products, ETAC, S-205, BLACK 305, BLACK 400, BLACK 100, BLACK 500, H-7001. GREEN 300, NIRBLACK 78, H-3035, ATP, H-1046, H-2114, GREEN-DCF, Blue-63, GN-169, crystal violet lactone are preferred since the color development characteristic in exposure to infrared rays is favorable.

The acid color-developing agent may be used singly or two or more acid color-developing agents may be jointly used.

The content of the acid color-developing agent is preferably 0.1% to 20% by mass, more preferably 1% to 15% by mass, and still more preferably 2% to 10% by mass of the total solid content of the composition of the embodiment of the present invention.

The acid color-developing agent develops color by being jointly used with an acid-generating agent. The acid-generating agent is a compound that generates an acid by the migration of electrons and/or the migration of energy from the infrared absorber excited by infrared rays. The generated acid reacts with the acid color-developing agent, whereby color is developed. As an acid to be generated, sulfonic acid, hydrochloric acid, hexafluorophosphoric acid, tetrafluoroboric acid, and the like are useful.

As the acid-generating agent, onium salts such as iodonium salts, sulfonium salts, phosphonium salts, diazonium salts, and azinium salts are exemplified. Specifically, compounds described in the specification of U.S. Pat. No. 4,708,925A, JP1995-020629A (JP-H07-020629A), and JP2008-195018A can be exemplified. In addition, benzyl sulfonates described in the specification of U.S. Pat. No. 5,135,838A or U.S. Pat. No. 5,200,544A are also preferred. Furthermore, active sulfonic acid esters described in JP1990-1000S4A (JP-H02-100054A), JP1990-1000S5A (JP-H02-100055A), and JP1997-197671A (JP-H09-

197671A), imide esters such as sulfinic acid esters of N-hydroxyamide compounds described in JP2008-001740A, or disulfone compounds described in JP1986-166544A (JP-S61-166544A), JP2003-328465A, and the like are also preferred. In addition, oxime ester compounds described in J. C. S. Perkin II (1979) 1653 to 1660, J. C. S. Perkin II (1979) 156 to 162, Journal of Photopolymer Science and Technology (1995) 202 to 232, JP2000-066385A, JP2000-080068A, and JP2008-19S018A are also preferred. Additionally, haloalkyl-substituted s-triazine compounds described in JP1995-271029A (JP-H07-271029A) are also preferred.

As the acid-generating agent, the iodonium salts, the sulfonium salts, and the azidium salts are particularly preferred.

Regarding the iodonium salts and the sulfonium salts, it is possible to incorporate the description of the iodonium salts and the sulfonium salts in the section of the polymerization initiator.

As examples of the azinium salts, 1-cyclohexylmethyloxypridinium=hexafluorophosphate, 1-cyclohexyloxy-4-phenylpyridinium=hexafluorophosphate, 1-ethoxy-4-phenylpyridinium=hexafluorophosphate, 1-(2-ethylhexyloxy)-4-phenylpyridinium=hexafluorophosphate, 4-chloro-1-cyclohexylmethyloxypyridinium=hexafluorophosphate, 1-ethoxy-4-cyanopyridinium=hexafluorophosphate, 3,4-dichloro-1-(2-ethylhexyloxy) pyridnium=hexafluorophosphate, 1-benzyloxy-4-phenylpyridinium=hexafluorophosphate, 1-phenethyloxy-4-phenylpyridinium=hexafluorophosphate, 1-(2-ethylhexyoloxy)-4-phenylpyridinium=p-toluenesulfonate, 1-(2-ethylhexyloxy)-4-phenylpyridinium=perfluorobutanesulfonate, 1-(2-ethylhexyloxy)-4-phenylpyridinium=bromide, and 1-(2-ethylhexyloxy)-4-phenylpyridinium=tetrafluoroborate are exemplified.

The acid-generating agent may contain the organic anion according to the present invention as an anion. In this case, the acid-generating agent corresponds to the specific compound according to the present invention.

The acid-generating agent may be used singly or two or more acid-generating agents may be jointly used.

The content of the acid-generating agent is preferably 1 to 30% by mass, more preferably 3 to 20% by mass, and still more preferably 6 to 15% by mass of the total solid content of the composition of the embodiment of the present invention.

[Radical Production Aid]

The composition of the embodiment of the present invention may contain a radical production aid. The radical production aid contributes to the improvement of the printing resistance of lithographic printing plates produced from lithographic printing plate precursors in a case in which the composition of the embodiment of the present invention is applied to image-recording layers in the lithographic printing plate precursors. Examples of the radical production aid include five kinds of radical production aids described below, (i) Alkyl or arylate complexes: B is considered that carbon-hetero bonds are oxidatively cleaved and active radicals are generated. Specific examples thereof include berate compounds and the like, (n) Amino acetate compounds: It is considered that C—X bonds on carbon adjacent to nitrogen are cleaved due to oxidation and active radicals are generated. X is preferably a hydrogen atom, a carboxy group, a trimethylsilyl group, or a benzyl group. Specific examples thereof include N-phenylglycines (which may have a substituent in a phenyl group), N-phenyl iminodiacetic acids (which may have a substituent in a phenyl group), and the like, (iii) Sulfur-containing compounds: The above-described amino acetate compounds in which a nitrogen atom is substituted with a sulfur atom are capable of generating active, radicals by means of the same action. Specific examples thereof include phenylthioacetic acids (which may have a substituent in a phenyl group) and the like, (iv) Tin-containing compounds: The above-described amino acetate compounds in which a nitrogen atom is substituted with a tin atom are capable of generating active radicals by means of the same action, (v) Sulfinate: Active radicals can be generated by means of oxidation. Specific examines thereof include sodium aryl sulfinate and the like.

Among these radical production aids, a borate compound is preferred. The borate compound is preferably a tetraaryl borate compound or a monoalkyltriaryl borate compound, mote preferably a tetraaryl borate compound from the viewpoint of the stability of the compound.

A counter cation in the borate compound is preferably an alkali metal ion or a tetraalkyl ammonium ion and more preferably a sodium ion, a potassium ion, or a tetrabutylammonium ion.

Specific examples of the borate compound include compounds illustrated below. Here, $X_c^+$ represents a monovalent cation and is preferably an alkali metal ion or a tetraalkyl ammonium ion and more preferably an alkali metal ion or a tetrabutylammonium ion. In addition, Bu represents an n-butyl group.

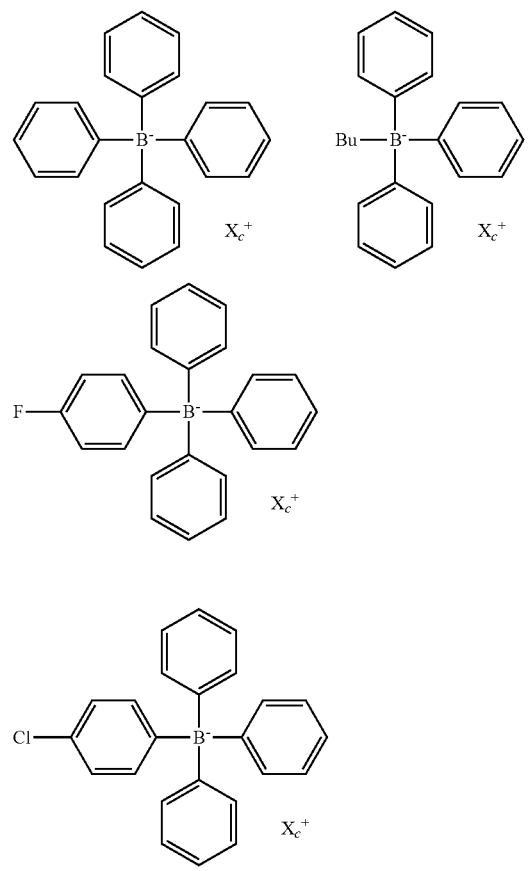

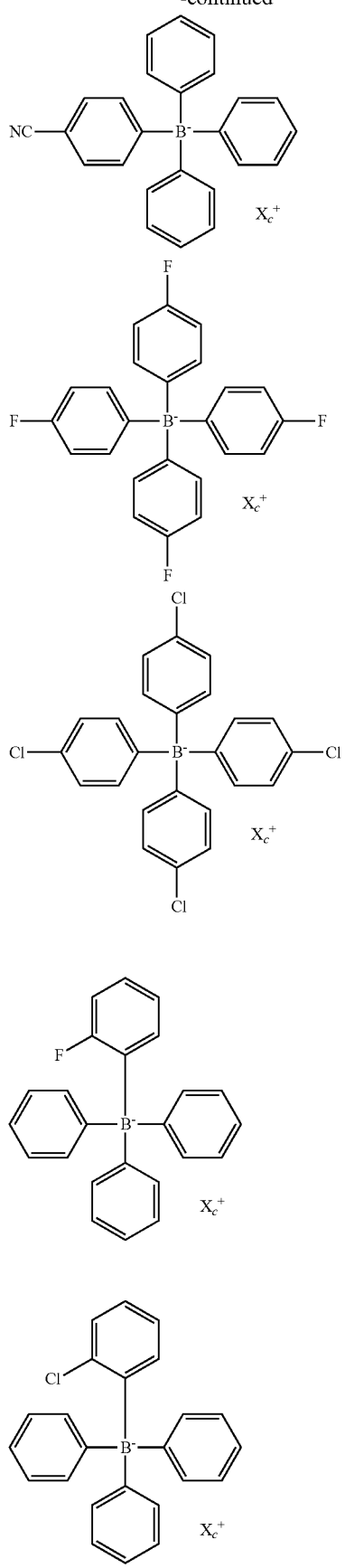
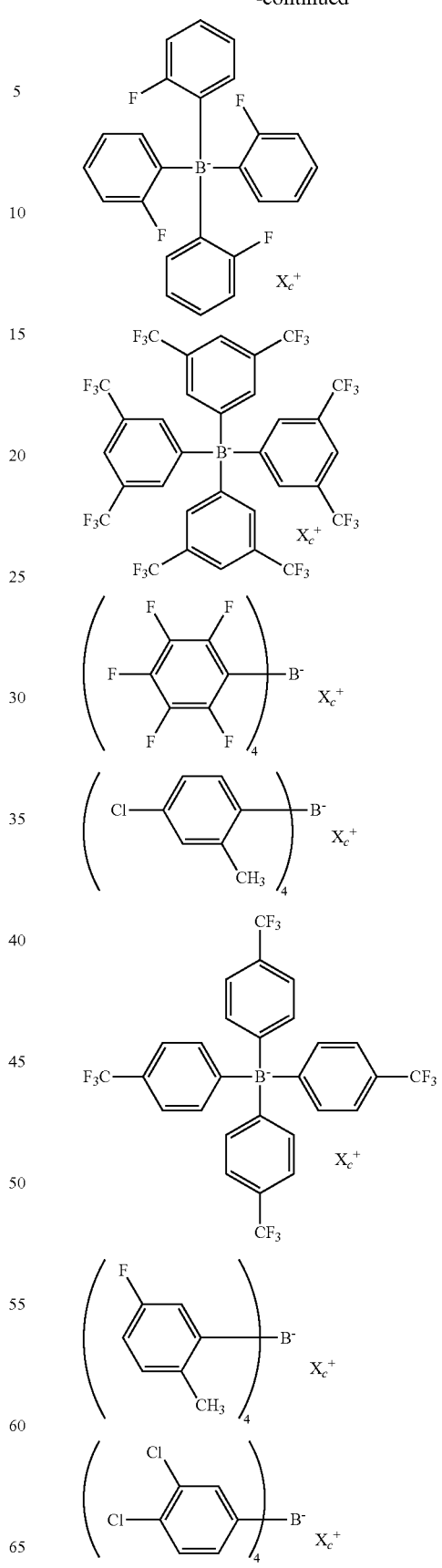

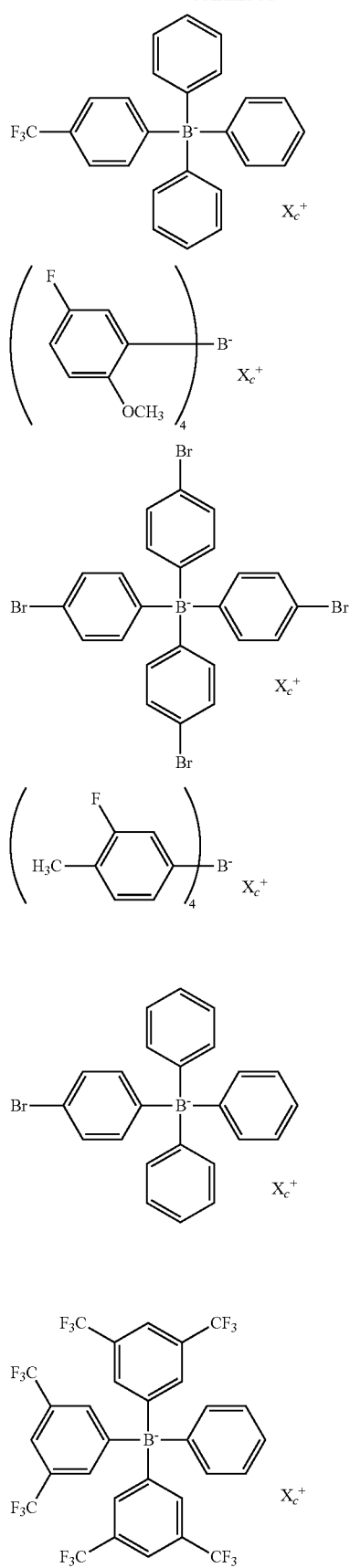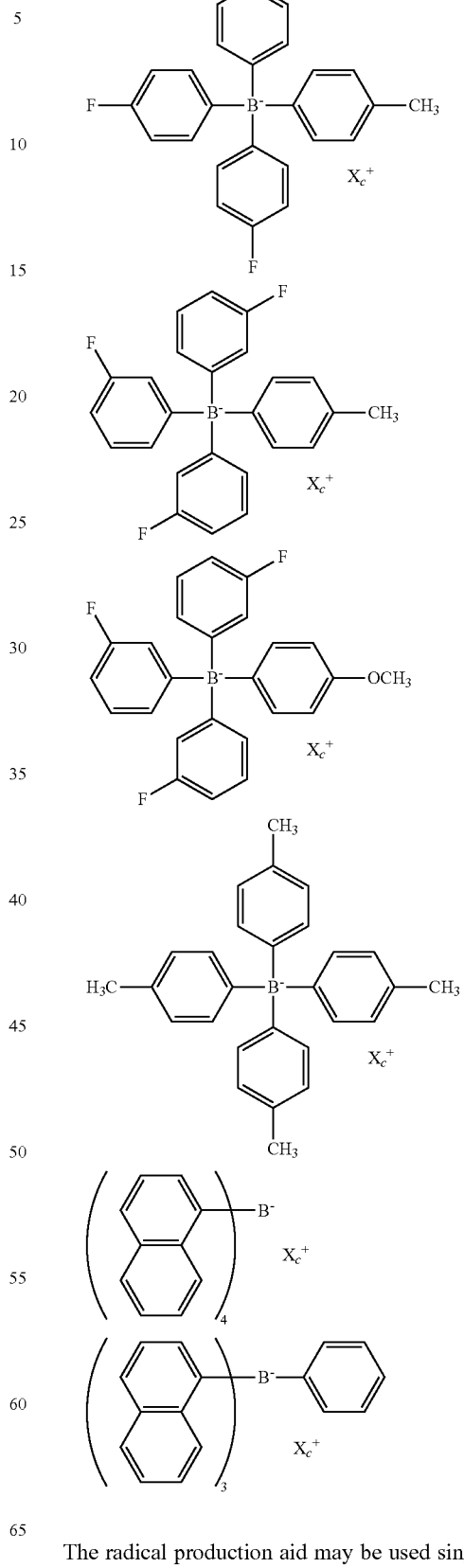
The radical production aid may be used singly or two or more radical production aids may be jointly used.

The content of the radical production aid is preferably 0.01% to 30% by mass, more preferably 0.05% to 25% by mass, and still more preferably 0.1% to 20% by mass of the total solid content of the composition of the embodiment of the present invention.

[Polymer Particle]

In a case in which the composition of the embodiment of the present invention is applied to an image-recording layer of a lithographic printing plate precursor, from the viewpoint of improving the on-machine developability of the lithographic printing plate precursor, the composition according to the embodiment of the present invention may contain a polymer particle. The polymer particle is preferably a polymer particle capable of converting the image-recording layer to be hydrophobic in the case of being irradiated with heat, preferably, heat generated by exposure.

The polymer particle is preferably at least one selected from a thermally adhesive particle, a thermally reactive polymer particle, a polymer particle having a polymerizable group, a microcapsule including a hydrophobic compound, or a micro gel (crosslinking polymer particle). Among these, a polymer particle having a polymerizable group and a micro gel are preferred.

Preferred examples of the thermally adhesive particle include a thermoplastic polymer particle described in Research Disclosure No. 33303 of January 1992 and the specifications of JP1997-123387A (JP-H09-123387A), JP1997-131850A (JP-H09-131850A), JP1997-171249A (JP-H09-171249AX JP1997-171250A (JP-H09-171250A), and EP931647B.

Specific examples of polymers that constitute the thermally adhesive particle include homopolymers or copolymers of monomers of ethylene, styrene, vinyl chloride, methyl acrylate, ethyl acrylate, methyl methacrylate, ethyl methacrylate, vinylidene chloride, acrylonitrile, vinylcarbazole, acrylates or methacrylates having polyalkylene structures, and the like and mixtures thereof preferred examples thereof include copolymers having polystyrene, styrene, and acrylonitrile and polymethyl methacrylate. The number-average primary particle diameter of the thermally adhesive particles is preferably in a range of 0.01 to 2.0 μm.

Examples of the thermally reactive polymer particle include a polymer particle having a thermally reactive group. The polymer particle having a thermally reactive group forms a hydrophobilized region through crosslinking by a thermal fraction and a change in a functional group at this time.

The thermally reactive group in the polymer particle having a thermally reactive group may be a functional group that causes any reactions as long as chemical bonds are formed, but is preferably a polymerizable group. Preferred examples thereof include ethylenically unsaturated groups that cause radical polymerization reactions (fin examide, acryloyl groups, methacryloyl groups, vinyl groups, allyl groups, and the like), cationic polymerizable groups (for example, vinyl groups, vinyloxy groups, epoxy groups, oxetanyl groups, and the like), isocyanato groups that cause addition reactions or blocked bodies thereof, epoxy groups, vinyloxy groups, functional groups having active hydrogen atoms that are reaction partners thereof (for example, amino groups, hydroxy groups, carboxy groups, and the like), carboxy groups that cause condensation reactions, hydroxy groups or amino groups that are reaction partners, acid anhydrides that cause ring-opening addition reactions, amino groups or hydroxy groups which are reaction partners, and the like.

Examples of the microcapsules include microcapsules including all or part of the constituent components of the image-recording layer as described in JP2901-277740A and JP2001-277742A. The constituent components of the image-recording layer can also be added outride the microcapsules. A preferred aspect of the image-recording layer including the microcapsules is an image-recording layer including hydrophobic constitutent components in the microcapsules and including hydrophilic constituent components outside the microcapsules.

Micro gels (crosslinking polymer particles) are capable of containing some of the constituent components of the composition of the embodiment of the present invention in at least one of the inside or surface thereof, and particularly, an aspect of micro capsules that have radical polymerizable groups on the surfaces and tints turn into reactive micro gels is preferred from the viewpoint of image-forming sensitivity or printing resistance.

In order to pot the constituent components of the composition of the embodiment of the present invention into microcapsules or micro gels, well-known methods can be used.

The volume average particle diameter of the microcapsules or the micro gels is preferably in a range of 0.01 to 3.0 μm, more preferably in a range of 0.05 to 2.0 μm, and still more preferably in a range of 0.10 to 1.0 μm. Within this range, favorable resolution and temporal stability can be obtained.

The volume average particle diameter is measured using a dynamic light scattering-type particle size distribution analyzer LB-500 (manufactured by Horiba Ltd.) and a light scattering method.

The content of the polymer particle is preferably 5% to 90% by mass of the total solid content of the composition of the embodiment of the present invention.

[Chain Transfer Agent]

The composition of the embodiment of the present invention may also contain a chain transfer agent. The chain transfer agent contributes to the improvement of the printing resistance of a lithographic printing plate practiced from a lithographic printing plate precursor in a case in which the composition of the embodiment of the present invention is applied to the image-recording layer in the lithographic printing plate precursor.

The chain transfer agent is preferably a thiol compound, from the viewpoint of the boiling point (the difficulty of volatilization), more preferably thiol having 7 or more carbon atoms, and still more preferably a compound having a mercapto group on an aromatic ring (an aromatic dried compound). The above-described dried compound is preferably a monofunctional thiol compound.

Specific examples of the chain transfer agent include the following compounds.

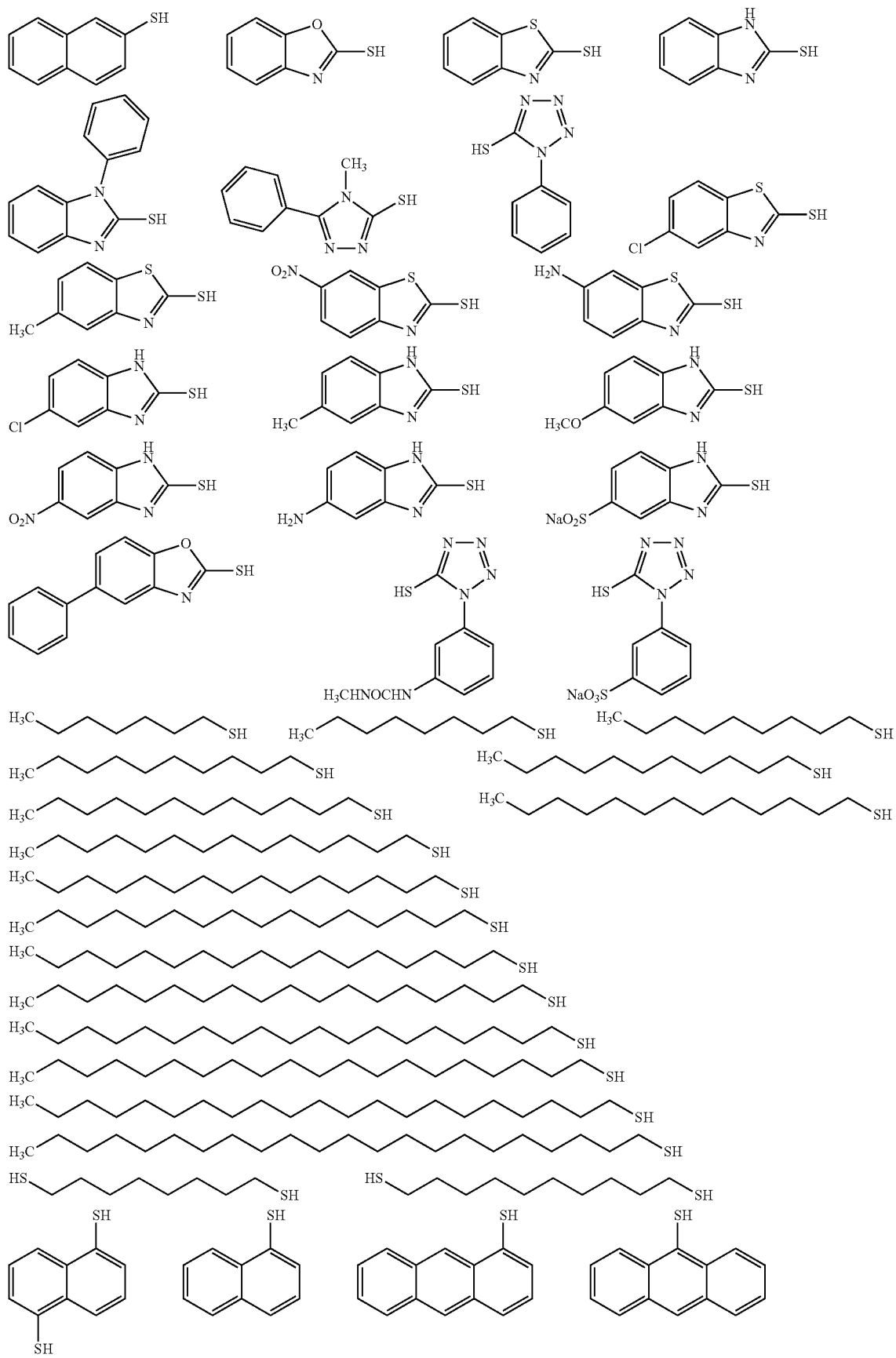

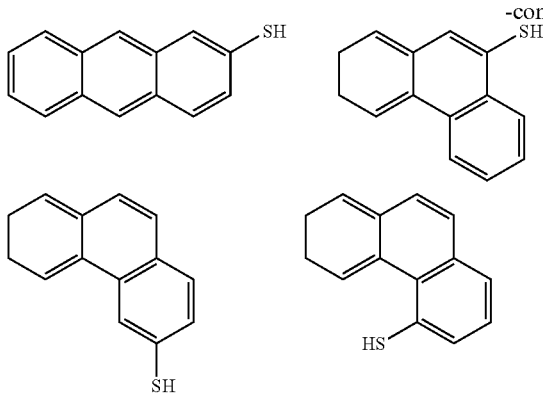
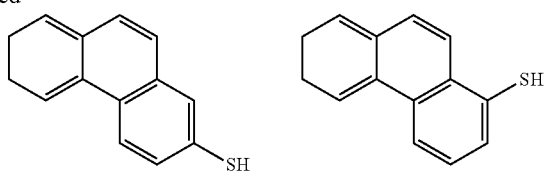

The chain transfer agent may be used singly or two or mote chain transfer agents may be jointly used.

The content of the chain transfer agent is preferably 0.01% to 50% by mass, more preferably 0.05% to 40% by mass, and still more preferably 0.1% to 30% by mass of the total solid contort of the composition of the embodiment of the present invention.

[Low-Molecular-Weight Hydrophilic Compound]

In the case of being applied to the image-recording layer in the lithographic printing plate precursor, in order to improve the on-machine developability of the lithographic printing plate precursor without degrading printing resistance al the lithographic printing plate produced from the lithographic printing plate precursor, the composition of the embodiment of the present invention may include a low-molecular-weight hydrophilic compound. Meanwhile, the low-molecular-weight hydrophilic compound is preferably a compound having a molecular weight of smaller than 1,000, more preferably a compound having a molecular weight of smaller than 800, and still more preferably a compound having a molecular weight of smaller than 500.

As the low-molecular-weight hydrophilic compound, examples of water-soluble organic compounds include glycols such as ethylene glycol, diethylene glycol, triethylene glycol, propylene glycol, dipropylene glycol, and tripropylene glycol and ethers or ester derivative thereof, polyols such as glycerin, pentaerythritol, and tris(2-hydroxyethyl) isocyanurate, organic amines such as triethanolamine, diethanolamine, and monoethanolamine and salts thereof organic sulfonic acids such as alkyl sulfonic acid, toluenesulfonic acid, and benzenesulfonic acid and salts thereof organic sulfamic acids such as alkyl sulfamate and salts thereof, organic sulfone acids such as alkyl sulfates and alkyl ether sulfates and salts thereof organic phosphonic acids such as phenylphosphonic acid and salts thereof organic carboxylic acids such as tartaric acid, oxalic acid, citric acid, malic acid, lactic acid, gluconic acid, and amino acid and salts thereof betaines, and the like.

The low-molecular-weight hydrophilic compound is preferably at least one selected from polyols, organic sulfates, organic sulfonates, or betaines.

Specific examples of the organic sulfonates include alkyl sulfonates such as sodium n-butyl sulfonate, sodium n-hexyl sulfonate, sodium 2-ethylhexyl sulfonate, sodium cyclohexyl sulfonate, and sodium n-octyl sulfonate; alkyl sulfonates having ethylene oxide chains such as sodium 5,8,11-trioxapentadecane-1-sulfonate, sodium 5,8,11-trioxaheptadecane-1-sulfonate, sodium 13-ethyl-5,8,11-trioxaheptadecane-1-sulfonate, sodium 5,8,11,14-tetraoxatetracosane-1-sulfonate; aryl sulfonates such as sodium benzene sulfonate, sodium p-toluenesulfonate, sodium p-hydroxybenzene sulfonate, sodium p-styrene sulfonate, sodium dimethyl isophthalate-5-sulfonate, sodium 1-naphdiyl sulfonate, sodium 4-hydroxynaphthylsulfonate, sodium 1,5-naphthalene disulfonate, and trisodium 1,3,6-naphthalene trisulfonate; compounds described in Paragraphs 0026 to 0031 of JP2007-2764S4A and Paragraphs 0020 to 0047 of JP2009-154525A; and foe like. The salts may be potassium salts or lithium salts.

Examples of the organic sulfates include of alkyls, alkenyls, alkynyls, aryls, or heterocyclic monoethers of polyethylene oxides. The number of ethylene oxide units is preferably in a range of 1 to 4, and the salts are preferably sodium salts, potassium salts, or lithium salts. Specific examples thereof include compounds described in Paragraphs 0034 to 0038 of JP2007-276454A.

The betaines are preferably compounds in which the number of carbon atoms in hydrocarbon substituents into nitrogen atoms is in a range of 1 to 5, and specific examples thereof include trimethyl ammonium acetate, dimethyl propyl ammonium acetate, 3-hydroxy-4-trimethyl ammonio butyrate, 4-(1-pyridino) butyrate; 1-hydroxyethyl-1-imidazolio acetate, trimethyl ammonium methanesulfonate, dimethyl propyl ammonium methanesulfonate, 3-trimethylammonio-1-propane sulfonate, 3-(1-pyridinio)-1-propane sulfonate, and the like.

Since the low-molecular-weight hydrophilic compound has a small structure in hydrophobic portions and barely has surfactant actions, there are no cases in which dampening water permeates exposed portions (image areas) in the image-recording layer and thus the hydrophobic properties or membrane hardness of the image areas degrade, and it is possible to favorably maintain the ink-receiving properties or printing resistance of the image-recording layer.

The low-molecular-weight hydrophilic compound may be used singly or two or mote low-molecular-weight hydrophilic compounds may be jointly used.

The content of the low-molecular-weight hydrophilic compound is preferably in a range of 0.5% to 20% by mass, mote preferably in a range of 1% to 15% by mass, and still more preferably in a range of 2% to 10% by mass of the total solid content of the composition of the embodiment of the present invention.

[Sensitization Agent]

In a case in which the composition of the embodiment of the present invention is applied to the image-recording layer in the lithographic printing plate precursor, in order to improve the ink-absorbing property of ink (hereinafter, also simply referred to as the "ink-absorbing property") in a lithographic printing plate produced from the lithographic printing plate precursor, the composition of the embodiment of the present invention may contain a sensitization agent such as a phosphonium compound, a nitrogen-containing low-molecular-weight compound, or an ammonium group-containing polymer. Particularly, in a Case in which the lithographic printing plate precursor contains an inorganic lamellar compound in the protective layer, these compounds function as surface coating agents for the inorganic lamellar compound and are capable of suppressing the ink-absorbing properties from being degraded in the middle of printing due to the inorganic lamellar compound.

Among these, a phosphonium compound, a nitrogen-containing low-molecular-weight compound, and an ammonium group-containing polymer are preferably jointly used as the sensitization agent, and a phosphonium compound, quaternary ammonium salts, and an ammonium group-containing polymer are more preferably jointly used.

Examples of a phosphonium compound include phosphonium compounds described in JP2006-297907A and JP2007-050660A. Specific examples thereof include tetrabutylphosphonium iodide, butyltriphenylphosphonium bromide, tetraphenylphosphonium bromide, 1,4-bis(triphenylphosphonio)butane=di(hexafluorophosphate), 1,7-bis(triphenylphosphonio)heptane=sulfate, 1,9-bis(triphenylphosphonio)nonane=naphthalene-2,7-disulfonate, and the like.

Examples of the nitrogen-containing low-molecular-weight compound include amine salts and quaternary ammonium salts. In addition, examples thereof include imidazolinium salts, benzo imidazolium salts, pyridinium salts, and quinolinium salts. Among these, quaternary ammonium salts and pyridinium salts are preferred. Specific examples thereof include tetramethylammonium=hexaflurophosphate, tetrabutylammonium=hexaflurophosphate, dodecyltrimethylammonium=p-toluene sulfonate, benzyltriethylammonium=hexaflurophosphate, benzayldimethyooxtylammonium=hexaflurophosphate, benzyldimethyldodecylammonium=hexaflurophosphate, compounds described in Paragraphs 0021 to 0037 of JP2008-284858A and Paragraphs 0030 to 0057 of JP2009-090645A, and the like.

The ammonium group-containing polymer needs to have an ammonium group in the structure, and polymer including 5% by mol to 80% by mol of (meth)acrylate having ammonium groups in side chains as copolymerization components are preferred. Specific examples thereof include polymers described in Paragraphs 0089 to 0105 of JP2009-208458A.

In the ammonium group-containing polymer, the value of the reducing specific viscosity (unit ml/g) obtained according to the measurement method described in JP2009-208458A is preferably in a range of 5 to 120, more preferably in a range of 10 to 110, and particularly preferably in a range of 15 to 100. In a case in which the reducing specific viscosity is converted to the weight-average molecular weight (Mw), the weight-average molecular weight is preferably in a range of 10,000 to 150,000, more preferably in a range of 17,000 to 140,000, and particularly preferably in a range of 20,000 to 130,000.

Hereinafter, specific of the ammonium group-containing polymer will be described. (1) 2-(Trimethylammonio)ethyl methacrylate=p-toluenesulfonate/3,6-dioxaheptyl methacrylate copolymer (molar ratio: 10/90, Mw: 45,000) (2) 2-(Trimethylammonio)ethyl methacrylate=hexafluorophosphate/3,6-dioxaheptyl methacrylate copolymer (molar ratio: 20/80, Mw, 60,000) (3) 2-(Ethyldimethylammonio)ethyl methacrylate=p-toluenesulfonate/hexyl methacrylate copolymer (molar ratio: 30/70, Mw 45,000) (4) 2-(Trimethylammonio)ethyl methacrylate=hexafluorophosphate/2-ethylhexyl methacrylate copolymer (molar ratio: 20/80, Mw 60,000) (5) 2-(Trimethylammonio)ethyl methacrylate=methylsulfate/hexyl methacrylate copolymer (molar ratio: 40/60, Mw 70,000) (6) 2-(Butyldimethylammonio)ethyl methacrylate=hexafluorophosphate/3,6-dioxaheptyl methacrylate copolymer (molar ratio: 25/75, Mw 65,000) (7) 2-(Butyldimethylammonio)ethyl acrylate=hexafluorophosphate/3,6-dioxaheptyl methacrylate copolymer (molar ratio: 20/B0, Mw, 65,000) (8) 2-(Butyldimethylammonio)ethyl methacrylate=13-ethyl-5,8,11-trioxa-1-heptadecanesulfonate/3,6-dioxaheptyl methacrylate copolymer (molar ratio: 20/80, Mw: 75,000) (9) 2-(Butyldimethylammonio)ethyl methacrylate=hexafluorophosphate/3,6-dioxaheptyl methacrylate/2-hydroxy-3-methacryloyloxypropyl methacrylate copolymer (molar ratio: 15/80/5, Mw: 65,000).

The content of the sensitization agent is preferably in a range of 0.01% to 30% by mass, more preferably in a range of 0.1% to 15% by mass, and still more preferably in a range of 1% to 10% by mass of the total solid content in the composition of the embodiment of the present invention.

[Coloring Agent]

The image-recording layer in the lithographic printing plate precursor of the embodiment of the present invention may contain a dye having a high absorption in the visible light range as a adoring agent of images. Specific examples thereof include OIL YELLOW #101, OIL YELLOW #103, OIL PINK #312, OIL GREEN BG, OIL BLUE BOS, OIL BLUE #603, OIL BLACK BY, OIL BLACK BS, OIL BLACK T-505 (all manufactured by Orient Chemical Industries, Ltd.), VICTORIA PURE BLUE, CRYSTAL VIOLET (042555), METHYL VIOLET (CT42535), ETHYL VIOLET, ETHYL VIOLET 6HNAPS, RHODAMINE B (CI145170B), MALACHITE GREEN (042000), METHYLENE BLUE (052015), and dyes described in JP1987-293247A (JP-S62-293247A). In addition, pigments such as phthalocyanine-based pigment, azo-based pigments, carbon made, and titanium oxide can also be preferably used. The image-recording layer preferably contains a coloring agent since it becomes easy to differentiate an image area and a non-image area after the formation of an image in the case of containing the coloring agent.

The amount of the coloring agent added is preferably 0.005 to 10% by mass of the total solid content of the image-recording layer

[Other Components]

The composition of the embodiment of the preset invention may contain, as other components, a surfactant, a polymerization inhibitor, a higher-fatty acid derivative, a plasticizer, inorganic particles, an inorganic lamellar compound, or the like. Specifically, the composition may contain individual components described in Paragraphs 0114 to 0159 of JP2008-284817A,

[Lithographic Printing Plate Precursor]

The lithographic printing plate precursor of the embodiment of the present invention has an image-recording layer containing the composition of the embodiment of the present invention on a support.

Hereinafter, an on-machine development-type lithographic printing plate precursor from which the characteristics of the composition of the embodiment of the present invention are significantly developed will be described as an example, but a development process-type lithographic printing plate precursor that is used to produce lithographic printing plates by a development process also will be appropriately described.

[Image-Recording Layer]

According to one aspect of the image-recording layer; the image-recording layer contains an infrared absorber, a polymerizable compound, a polymerization initiator, and al least one of a binder polymer or a polymer particle. The image-recording layer preferably further contains a radical production aid and a chain transfer agent.

According to another aspect of the image-recording layer, the image-recording layer contains an infrared absorber, a thermally adhesive particle, and a tender polymer.

In order to improve the plate inspection property of the lithographic printing plate precursor, it is possible to acid an acid color-developing agent to the image-recording layer.

In the image-recording layer, as the polymerization initiator and the infrared absorber, the specific compound according to the present invention can be used. In addition, in the image-recording layer containing the acid color-developing agent, as the acid-generating agent with respect to the acid color-developing agent, the specific compound according to the present invention can be used.

Regarding the respective components such as an infrared absorber, a polymerizable compound, a polymerization initiator, a binder polymer, a polymer particle, a radical production aid, a chain transfer agent, and a thermally adhesive particle that are added to the image-recording layer and contents thereof, it is possible to refer to the description of the composition of the embodiment of the present invention.

<Formation of Image-Recording Layer>

The image-recording layer can be formed by, for example, as described in Paragraphs 0142 and 0143 of JP2008-195018A, preparing a coating fluid by dispersing or dissolving the respective necessary components described above in a solvent, applying the coating fluid onto a support using a well-known method such as bar coater coating, and drying the coating fluid.

As the solvent, a well-known solvent can be used. Specific examples thereof include water, acetone, methyl ethyl ketone (2-butanone), cyclohexane, ethyl acetate, ethylene dichloride, tetrahydrofuran, toluene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 1-methoxy-2-propanol, 3-methoxy-1-propanol, methoxy methoxyethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethylformamide, dimethyl sulfimide, γ-butyrolactone, methyl lactate, ethyl lactate, and the like. The solvent may be used singly or two or more solvents may be jointly used. The concentration of the solid content in the coating fluid is preferably approximately 1% to 50% by mass.

The coating amount (solid content) of the image-recording layer after application and drying varies depending cm applications, however, is preferably approximately 0.3 to 3.0 g/m² from the viewpoint of obtaining a favorable sensitivity and favorable membrane characteristics of the image-recording layer.

[Undercoat Layer]

The lithographic printing plate precursor according to the embodiment of the present invention preferably has an undercoat layer (in some cases, referred to as the interlayer) between the image-recording layer and the support. The undercoat layer strengthens adhesiveness between the support and the image-recording layer in exposed portions and facilitates peeling the image-recording layer from the support in non-exposed portions, and thus the undercoat layer contributes to improving developability without printing resistance. In addition, in the case of exposure using infrared lasers, the undercoat layer functions as an adiabatic layer and thus also has an effect of preventing the degradation of the sensitivity due to the diffusion of heat generated by exposure in the support.

Examples of compounds that can be used for the undercoat layer include polymers having adsorbent groups that can be adsorbed to the surface of the support and hydrophilic groups. In order to improve adhesiveness to the image-recording layer, polymers having adsorbent groups and hydrophilic groups and further having crosslinking groups are preferred. The compounds that can be used for the undercoat layer may be low-molecular-weight compounds or polymers. The compounds that can be used for the undercoat layer may be used in a mixed form of two or more kinds as necessary.

In a case in which the compounds that are used for the undercoat layer are polymers, copolymers of monomers having adsorbent groups, monomers having hydrophilic groups, and monomers having crosslinking groups are preferred.

The adsorbent groups that can be adsorbed to the surface of the support are preferably phenolic hydroxy groups, carboxy groups, $-PO_3H_2$, $-OPO_3H_2$, $-CONHSO_2-$, $-SO_2NHSO_2-$, $-COCH_2COCH_3$. The hydrophilic groups are preferably sulfo groups or sails thereof and salts of carboxy groups. The crosslinking groups are preferably acrylic groups, methacrylic groups, acrylamide groups, methacrylamide groups, allyl groups, and the like.

The polymers may have crosslinking groups introduced due to the formation of salts between polar substituents of the polymers and compounds having substituents having opposite charges of the above-described polar substituents and ethylenically unsaturated bonds and may be further copolymerized with monomers other than the above-described monomers, preferably, hydrophilic monomers.

Specifically, preferred examples thereof include silane coupling agents having ethylenic doable bond reactive groups that are capable of addition polymerization described in JP1998-282679A (JP-H10-282679A) and phosphorus compounds having ethylenic doable bond reactive groups described in JP1990-304441A (JP-H02-304441A). Low-molecular-weight or high-molecular-weight compounds having crosslinking groups (preferably ethylenically unsaturated bond groups), functional groups that interact with the surface of the support, and hydrophilic groups described in JP2005-238816A, JP2005-125749A, JP2006-239867A, and JP2006-215263A are also preferably used.

More preferred examples thereof include high-molecular-weight polymers having adsorbent groups foal can be adsorbed to the surface of the support, hydrophilic groups, and crosslinking groups described in JP2005-125749A and JP2006-188038A.

The content of ethylenically unsaturated bond groups in the polymer that is used in the undercoat layer is preferably in a range of 0.1 to 10.0 mmol and more preferably in a range of 0.2 to 5.5 mmol per gram of the polymer.

The weight-average molecular weight (Mw) of the polymer that is used in the undercoat layer is preferably 5,000 or biller and more preferably in a range of 10,000 to 300,000.

In addition to the above-described compounds for the undercoat layer, the undercoat layer may also include a chelating agent, secondary or tertiary amines, a polymerization inhibitor; compounds having amino groups or functional groups having a polymerization-inhibiting function and groups that interact with the surfaces of supports (for example, 1,4-diazabicyclo[2.2.2]octane (DABCO), 2,3,5,6-tetrahydroxy-p-quinone, chloranil, sulfophthalic acid, hydroxyethyl ethylene diamine triacetic acid, dihydroxyethyl ethylenediamine diacetic acid, hydroxyethyl iminodiacetic acid, and the like), and the like in order to prevent stain over time.

The undercoat layer is formed using well-known coating methods. The coating amount (solid content) of the undercoat layer is preferably in a range of 0.1 to 100 mg/m$^2$ and more preferably in a range of 1 to 30 mg/m$^2$,

[Protective Layer]

The lithographic printing plate precursor according to the embodiment of the present invention may have a protective layer (in some cases, also referred to as the overcoat layer) on the image-recording layer. The protective layer has a function of suppressing image formation-inhibiting reactions caused by the shielding of oxygen and additionally has a function of preventing the generation of damage in the image-recording layer and abrasion prevention during exposure using high-illuminance lasers.

Protective layers having the above-described characteristics are described m, fin example, the specification of U.S. Pat. No. 3,458,311A and JP1980-049729B (JP-S55-049729B). As poor oxygen-transmissible polymers that can be used for the protective layer; it is possible to appropriately select and use any one of water-soluble polymers and water-insoluble polymers, and, if necessary, it is also possible to use two or mote polymers in a mixed form. Specific examples thereof include polyvinyl alcohol, modified polyvinyl alcohol, polyvinyl pyrrolidone, water-soluble cellulose derivatives, poly(meth)acrylamide, and the like.

As the modified polyvinyl alcohol, acid-modified polyvinyl alcohol having carboxy groups or sulfo groups are preferably used. Specific examples thereof include modified-polyvinyl alcohols described in JP2005-2S0216A and JP2006-259137A.

The protective layer preferably includes inorganic lamellar compounds in order to enhance oxygen-shielding properties. The inorganic lamellar compounds refer to particles having dim flat plate shapes, and examples thereof include mica groups such as natural mica and synthetic mica, talc represented by Formula: $3MgO.4SiO.H_2O$, taeniolite, montmorillonite, saponite, hectorite, zirconium phosphate, and the like.

The inorganic lamellar compounds that can be preferably used are mica compounds. Examples of mica compounds include mica groups such as natural mica and synthetic mica represented by Formula: $A (B, C)_{2-5}D_4O_{10}(OH, F, O)_2$ (here, A is at least one element selected from the group of K, Na, and Ca, B and C are at least one element selected from the group consisting of Fe (II), Fe (III), Mn, Al, Mg, and V, and D is Si or Al.].

In the mica group, examples of natural mica include white mica, soda mica, gold mica, black mica, and lepidolite. Examples of synthetic mica include non-swelling mica such as fluorphlogopite $KMg_3(AlSi_3O_{10})F_2$, potassium tetrasilic mica $KMg_{2.5}(Si_4O_{10})F_2$, and, Na tetrasilylic mica $NaMg_{2.5}(Si_4O_{10})F_2$, swelling mica such as Na or Li taeniolite (Na, Li)$Mg_2Li(Si_4O_{10})F_2$, montmorillonite-based Na or Li hectorite (Na, Li)$_{1/g}Mg_{2/5}Li_{1/8}(Si_4O_{10})F_2$, and the like. Furthermore, synthetic smectite is also useful.

Among the above-described mica compounds, fluorine-based swelling mica is particularly useful. That is, swelling synthetic mica has a laminate structure consisting of unit crystal lattice layers having a thickness in a range of approximately 10 to 15 Å (1 Å is equal to 0.1 nm), and metal atoms in lattices are more actively substituted than many other clay minerals. As a result, positive charges are deficient in the lattice layers, and positive ions such as $Li^+$, $Na^+$, $Ca^{2+}$, and $Mg^{2+}$ are adsorbed between the layers in order to for the deficiency. Positive ions interposed between the layers are referred to as exchangeable positive ions and are exchangeable with various positive ions. Particularly, in a case in which the positive ions between the layers are $Li^+$ and $Na^+$ the ionic radii are small, and thus the bonds between lamellar crystal lattices are weak, and mica is significantly swollen by water. In a case in which shear is applied in this state, mica easily cleavages and forms a stable sol in water. The above-described tendency of swelling synthetic mica is strong, and the swelling synthetic mica is particularly preferably used.

From the viewpoint of diffusion control, regarding the shapes of the mica compounds, the thickness is preferably thin, and the planar size is preferably large as long as the smoothness and active light ray-transmitting properties of coated surfaces are not impaired. Therefore, the aspect ratio is preferably 20 or higher, more preferably 100 or higher, and particularly preferably 200 or higher. The aspect ratio is the ratio of the long diameter to the thickness of a particle and can be measured from projection views obtained from the microphotograph of the particle. As the aspect ratio increases, the obtained effect becomes stronger.

Regarding the particle diameters of the mica compound, the average long diameter thereof is preferably in a range of 0.3 to 20 μm, more preferably in a range of 0.5 to 10 μm, and particularly preferably in a range of 1 to 5 μm. The average thickness of the particles is preferably 0.1 μm or smaller, more preferably 0.05 μm or and particularly preferably 0.01 μm or smaller. Specifically, for example, in the case of swelling synthetic mica which is a typical compound, a preferred aspect has a thickness in a range of approximately 1 to 50 nm and a surface size (long diameter) in a range of approximately 1 to 20 μm.

The content of the inorganic lamellar compound is preferably in a range of 0% to 60% by mass and more preferably in a range of 3% to 50% by mass of the total solid content of the protective layer. Even in a case in which a plurality of lands of inorganic lamellar compounds are jointly used, the total amount of the inorganic lamellar compounds is preferably the above-described content within the above-described range, the oxygen-shielding properties improve, and a favorable sensitivity can be obtained, to addition, the degradation of the ink-absorbing properties can be prevented.

The protective layer may include well-known additives such as a plasticizer for imparting flexibility, a surfactant for improving coating properties, and inorganic particles fin controlling sliding properties on the surface. The protective layer may contain the specific compound according to the present invention. The protective layer may contain the sensitization agent described in the section of the image-recording layer.

The protective layer is formed using a well-known coating method. The coating amount of the protective layer (solid content) is preferably in a range of 0.01 to 10 g/m$^2$, more preferably in a range of 0.02 to 3 g/m², and particularly preferably in a range of 0.02 to 1 g/m².

[Support]

A support in the lithographic printing plate precursor according to foe embodiment of the present invention can be appropriately selected from well-known supports for a lithographic printing plate precursor and used. The support is preferably an aluminum plate which has been roughened using a well-known method and anodized.

On the aluminum plate, as necessary, enlargement processes or sealing processes of micropores in anodized films described in JP2001-253181A and JP2001-322365A, surface hydrophilization processes using alkali metal silicate as described in foe specifications of U.S. Pat. Nos. 2,714,066A, 3,181,461A, 3,280,734A, and 3,902,734A, and surface hydrophilization processes using polyvinyl phosphate or the like as described in the specifications of U.S. Pat. No. 3,276,868A, 4,153,461A, and 4,689,272A may be appropriately selected and carried out.

In the support, the center line average roughness is preferably in a range of 0.10 to 1.2 μm.

The support may have, as necessary, a backcoat layer including an organic polymer compound described in JP1993-045885A (JP-H05-045885A) or an alkoxy compound of silicon described in JP1994-G35174A (JP-H06-035174A) on foe surface opposite to the image-recording layer.

[Method for Producing Lithographic Printing Plate]

A method for producing a lithographic printing plate according to the embodiment of the present invention preferably includes a step of image-exposing the lithographic printing plate precursor according to the embodiment of the present invention (exposure step), and a step of removing a non-exposed portion in the image-recording layer using at least one selected from printing ink or dampening water in the lithographic printing plate precursor that has been exposed in an image pattern on a printer (on-machine development step).

In addition, the method for producing a lithographic printing plate according to the embodiment of the present invention preferably includes a step of image-exposing the lithographic printing plate precursor of the embodiment of the present invention (exposure step) and a step of removing a non-exposed portion of the image-recording layer from the image-exposed lithographic printing plate precursor using a developer having a pH of 2 to 11 (development process step).

[Exposure Step]

Image exposure is preferably earned out using a method in which digital data are scanned and exposed using an infrared laser or the like.

The wavelength of the exposure light source is preferably in a range of 750 nm to 1,400 nm. The light source having a wavelength in a range of 750 nm to 1,400 nm is preferably a solid-state laser or a semiconductor laser that radiates infrared rays. The exposure mechanism may be any one of in-plane drum methods, external surface drum methods, flat head methods, and the like.

The exposure step can be carried out using platesetters or the like and well-known methods. In addition, in the case of including the on-machine development step, exposure may be earned out on a printer using a printer comprising an exposure device after the lithographic printing plate precursor is mounted on the printer.

[On-Machine Development Step]

In the on-machine development step, in a case in which printing (on-machine development) is initiated by supplying at least one selected from printing ink or dampening water, preferably, printing ink and dampening water on the printer without carrying out any development processes on the image-exposed lithographic printing plate precursor, non-exposed portions on the lithographic printing plate precursor are removed at the initial stage of printing, and accordingly, the hydrophilic surface of the support is exposed, and non-image areas are formed. As the printing ink and dampening water, well-known printing ink and dampening water for lithographic printing are used. Any of printing ink and dampening water may be first supplied to the surface of the lithographic printing plate precursor, but it is preferable to first supply printing ink from the viewpoint of preventing contamination by the components of the image-recording layer from which dampening water is removed.

In the above-described manner, the lithographic printing plate precursor is on-machine-developed on an off-set printer and is used as it is for printing a number of pieces of papa.

The method for producing a lithographic printing plate according to the embodiment of the present invention may also include other well-known steps in addition to the above-described steps. Examples of other steps include a step of checking a position, a direction, or the like of a lithographic printing plate precursor before each step, or a checking step of checking a printed image after an on-machine development step.

[Development Process Step]

The lithographic printing plate, precursor according to the embodiment of the present invention can be used to produce lithographic printing plates by means of a development process in which a developer is used by appropriately selecting the binder polymer and the like which are the constituent components of the image-recording layer. Examples of the development process in which a developer is used include an aspect in which a developer having a high pH of 14 or less which includes an alkaline agent is used (also referred to as alkali development process) and an aspect in which a developer having a pH of 2 to 11 which may contain at least one compound selected from the group consisting of a surfactant and a water-soluble polymer compound is used (also referred to as simple development process).

In the alkali development process in which an alkali developer having a high pH is used, for example, the protective layer is removed by a prior water washing step, next; alkali development is carried out, an alkali is removed by means of water washing in a post water washing step, a gum liquid process is carried out, and the lithographic pruning plate precursor is dried in a drying step. In contrast, in the simple development process, the protective layer is also removed at the same time in the case of having the protective layer, and thus it becomes possible not to provide the prior water washing step.

In addition, in a case in which a water-soluble polymer compound is added to the developer as necessary, it is possible to carry out development and the gum liquid process step at the same time. Therefore, the post water washing step is not particularly necessary, and it is possible to carry out the drying step after carrying out development and the gum liquid process in a single step using a single liquid. Therefore, the development process in which a developer is used is preferably a method fin producing a lithographic printing plate including a step of developing the image-exposed lithographic printing plate precursor using a developer having a pH of 2 to 11. After the development process, it is preferable to remove the excess developer using a squeeze roller and then dry the lithographic printing plate precursor.

That is, in the development process step of the method for producing a lithographic printing plate according to the embodiment of the present invention, it is preferable to carry out the development process and the gum liquid process in a single step using a single liquid.

Carrying out the development process and the gum liquid process in a single step using a single liquid means that the development process and the gum liquid process are not carried out as separate steps, but the water-soluble polymer compound is added to the developer, and the development process and the gum liquid process are earned out in a single step using a single liquid.

The development process can be preferably carried out using means for supplying the developer and an automatic development processor comprising a rubbing member. The rubbing member is particularly preferably an automatic development processor in which a rotary brush roll is used.

The number of the rotary brash rolls is preferably two or mote. Furthermore, the automatic development processor preferably comprises, after the development process means, means for removing an excess developer such as a squeeze roller or drying means such as a hot air device. In addition, the automatic development processor may comprise, before the development process means, preheating means for heating the image-exposed lithographic printing plate precursor.

A process in the above-described automatic development processor has an advantage that there is no need for coping with development scum derived from the protective layer/a photosensitive layer that is generated in foe case of so-called on-machine development process.

In the development step, in the case of a manual process, as a development process method, for example, a method in which an aqueous solution is soaked into a sponge or an absorbent cotton, the lithographic printing plate precursor a processed while rubbing the entire surface of the plate with the sponge or the absorbent cotton, and, after the end of the process, the lithographic printing plate precursor is dried is preferably exemplified. In the case of an immersion process, for example, a method in which the lithographic printing plate precursor is immersed in a pad or a deep tank filled with an aqueous solution and stirred for approximately 60 seconds and then dried while bang rubbed with an absorbent codon, a sponge, or the like is preferably exemplified.

Is the development process, a device having a simplified structure and a simplified step is preferably used.

In the alkali development process, the protective layer is removed by the prior water washing step, next, development is carried oat using an alkaline developer having a high pH, after that, an alkali is removed in the post water washing step, a gum process is carried out in a gum-pulling step, and the lithographic printing plate precursor is dried in the drying step.

In the simple development process, it is possible to carry out development and gam pulling at the same time using a single liquid. Therefore, it becomes possible not to provide the post water washing step and the gum process step, and it is preferable to carry out development and gum polling (gum liquid process) using a single liquid and then carry oat the drying step as necessary.

Furthermore, it is preferable to carry out the removal of the protective layer, development, and gum pulling at the same time using a single liquid without carrying out the prior water washing step. In addition, it is preferable to, after development and gum polling, remove the excess developer using a squeeze roller and then dry the lithographic printing plate precursor:

In the development process step, a method in which the lithographic printing plate precursor is immersed in the developer once or a method in which the lithographic printing plate precursor is immersed in the developer twice or more may be used. Among these, a method in which the lithographic printing plate precursor is immersed in the developer once or twice b preferred.

For the immersion, the exposed lithographic pruning plate precursor may be immersed in a developer tank filled with the developer or the developer may be blown onto the plate surface of the exposed lithographic printing plate precursor by means of spraying or the like.

Meanwhile, even in the case of immersing the lithographic printing plate precursor in the developer twice or more, a case in which the lithographic printing plate precursor b immersed twice or more in the same developer or a developer and another developer (tired liquid) in which the components of the image-recording layer are dissolved or dispersed due to the development process is regarded as the development process using a single liquid (single liquid process).

In the development process, a rubbing member is preferably used, and, in a development bath for removing the non-image area of the image-recording layer, the robbing member such as a brush is preferably installed.

The development process can be carried out according to an ordinary method al a temperature of preferably 0° C. to 60° C. and more preferably 15° C. to 40° C. by, for example, immersing the exposed lithographic printing plate precursor in the developer and rubbing the lithographic priming plate precursor with a brush or drawing a process liquid prepared in an external tank using a pump, blowing the process liquid to the lithographic printing plate precursor from a quay nozzle, and robbing the lithographic printing plate precursor with a brush. This development process can be continuously carried out a plurality of times. For example, after a developer prepared in an external tank is drown using a pump and blown to the lithographic priming plate precursor from a spray nozzle, and the lithographic printing plate precursor is rubbed with a brush, again, it is possible to blow the developer from the spray nozzle and rub the lithographic printing plate precursor with the brush. In the case of carrying out the development process using an automatic developing machine, the developer becomes more the due to an increase in the process amount, and thus it is preferable to restore the process capability using a supplementary liquid or a fresh developer.

In the development process, it is also possible to use a gum coater or an automatic developing machine that has been known in the related art for presensitized plates (PS plates) and computer to plates (CTP). In the case of using an automatic developing machine, for example, it is possible to apply any method of a method in which a developer prepared in a development tank or a developer prepared in an external tank is drawn using a pump and blown to a lithographic printing plate precursor from a spray nozzle, a method in which a printing plate is immersed and transported in a liquid in a tank filled with a developer using a guide roll or the like, or a so-called single-use process method in which only a necessary amount of a substantially unused developer is supplied to each plate and is processed. In any of the methods, a rubbing mechanism such as a brush or a moulton roller is more preferably provided. For example, it is possible to use commercially available automatic developing machines (Clean Out Unit C85/C125, Clean-Out Unit+ C85/120, FGF 85V, FGF 125V, FGF News (manufactured by Glunz & Jensen), Azura CX85, Azura CX125, Azura CX150 (manufactured by AGFA GRAPHICS). In addition, it is also possible to use a device into which a laser-exposed portion and an automatic developing machine portion are integrally combined.

The details of components and the like of the developer that is used in the development process step will be described below.

[pH]

The pH of the developer is preferably 2 to 11, more, preferably 5 to 9, and still more preferably 7 to 9. From the viewpoint of developability or the dispersibility of the image-recording layer; it is advantageous to set the value of pH to be high; however, regarding a printing property, particularly, the suppression of stain, it is effective to set the value of pH to below.

Here, the pH is a value dot is measured at 25° C. using a pH meter (model No.: HM-31, manufactured by DKK-Toa Corporation).

[Surfactant]

The developer may contain a surfactant such as an anionic surfactant, a nonionic surfactant, a cationic surfactant, or an amphoteric surfactant.

From the viewpoint of a blanket stain property, the developer preferably me hides at least one selected from the group consisting of an anionic surfactant and an amphoteric surfactant.

In addition, the developer preferably includes a nonionic surfactant and more preferably includes a nonionic surfactant and at least one selected from the group consisting of an anionic surfactant and an amphoteric surfactant.

As the anionic surfactant, a compound represented by Formula (I) is preferably exemplified.

$$R^1-Y^1-X^1 \quad (I)$$

In Formula (I), $R^1$ represents an alkyl group, a cycloalkyl group, an alkenyl group, an aralkyl group, or an aryl group which may have a substituent.

As the alkyl group, for example, an alkyl group having 1 to 20 carbon atoms is preferred, and, specifically, a methyl group, an ethyl group, a propyl group, an n-butyl group, a sec-butyl group, a hexyl group, a 2-ethylhexyl group, an octyl group, a decyl group, a dodecyl group, a hexadecyl group, a stearyl group, and the like can be preferably exemplified.

The cycloalkyl group may be a monocyclic cycloalkyl group or a polycyclic cycloalkyl group. As the monocyclic cycloalkyl group, a monocyclic cycloalkyl group having 3 to 8 carbon atoms is preferred, and a cyclopropyl group, a cyclopentyl group, a cyclohexyl group, or a cyclooctyl group is more preferred. As the polycyclic cycloalkyl group, for example, an adamantyl group, a norbornyl group, an isobornyl group, a camphanyl group, a dicyclopentyl group, an α-pinel group, a tricyclodecanyl group, and the like can be preferably exemplified.

As the alkenyl group, fin example an alkenyl group having 2 to 20 carbon atoms is preferred, and, specifically, a vinyl group, an allyl group, a butenyl group, a cyclohexenyl group, and the like can be preferably exemplified.

As the aralkyl group, for example, an aralkyl group having 7 to 12 carbon atoms is preferred, and, specifically, a benzyl group, a phenethyl group, a naphthylmethyl group, and the like can be preferably exemplified.

As the aryl group, for example, an aryl group having 6 to 15 carbon atoms is preferred, and, specifically, a phenyl group, a tolyl group, a dimethylphenyl group, a 2,4,6-trimethylphenyl group, a naphthyl group, an anthryl group, a 9,10-dimethoxyanthryl group, and the like can be preferably exemplified.

As the substituent, monovalent non-metal atomic groups excluding a hydrogen atom are used, and preferred examples thereof include a halogen atom (F, Cl, Br, or I), a hydroxy group, an alkoxy group, an aryloxy group, an acyl group, an amide group, an ester group, an acyloxy group, a carboxy group, a carboxylic acid anion group, a sulfonic acid anion group, and the like.

As specific examples of the alkoxy group in the substituent, alkoxy groups preferably having 1 to 40 carbon atoms and more preferably having 1 to 20 carbon atoms such as a methoxy group, an ethoxy group, a propyloxy group, an isopropyloxy group, a butyloxy group, a pentyloxy group, a hexyloxy group, a dodecyloxy group, a stearyloxy group, a methoxyethoxy group, a polyethyleneoxy) group, and a poly(propyleneoxy) group are exemplified. As the aryloxy group, aryloxy groups having 6 to 18 carbon atoms such as a phenoxy group, a tolyloxy group, a xylyloxy group, a mesityloxy group, a cumenyl oxy group, a methoxyphenyloxy group, an ethoxyphenyloxy group, a chlorophenyloxy group, a bromophenyloxy group, and a naphthyloxy group are exemplified. As the acyl group, acyl groups having 2 to 24 carbon atoms such as an acetyl group, a propanoyl group, a butanoyl group, a benzoyl group, and a naphthoyl group are exemplified. As the amide group, amide groups having 2 to 24 carbon atoms such as an acetamide group, a propionic acid amide group, a dodecanoic acid amide group, a palmitic acid amide group, a stearic acid amide group, a benzoic acid amide group, and a naphthoic acid amide group are exemplified. As the acyloxy group, acyloxy groups having 2 to 20 carbon atoms such as an acetoxy group, a propanoyloxy group, a benzoyloxy group, and a naphthoyloxy group are exemplified. As the ester group, ester groups having 1 to 24 carbon atoms such as a methyl ester group, an ethyl ester group, a propyl ester group, a hexyl ester group, an octyl ester group, a dodecyl ester group, and a stearyl ester group are exemplified. The substituent may be a substituent formed of a combination of two or more substituents described above.

$X^1$ represents a sulfonate group, a sulfane acid monoester salt group, a carboxylate group, or a phosphate group.

$Y^1$ represents a single bond, $-C_nH_{2n}-$, $-C_{n-m}H_{2(n-m)}OC_mH_{2m}-$, $-O-(CH_2CH_2O)_n-$, $-O-(CH_2CH_2CH_2O)_n-$, $-CO-NH-$, or a divalent linking group formed of a combination of two or more thereof and satisfies n≥1 and n≥m≥0.

Among compounds represented by Formula (I), a compound represented by Formula (I-A) or (I-B) is preferred from the viewpoint of scratch stain resistance,

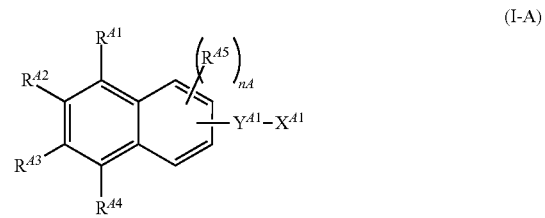

(I-A)

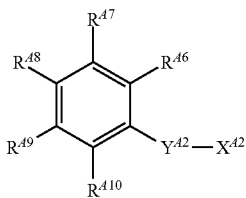 (I-B)

In Formula (I-A) and Formula (I-B), $R^{A1}$ to $R^{A10}$ each independently represent a hydrogen atom or an alkyl group, nA represents an integer of 1 to 3, $X^{A1}$ and $X^{A2}$ each independently represents a sulfonate group, a sulfinic acid monoester salt group, a carboxylate group, or a phosphate group, $Y^{A1}$ and $Y^{A2}$ each independently represents a single bond, $-C_nH_{2n}-$, $-C_{n-m}H_{2(n-m)}OC_mH_{2m}-$, $-O-(CH_2CH_2O)_n-$, $-O-(CH_2CH_2CH_2O)_n-$, $-CO-NH-$, or a divalent linking group formed of a combination of two or more thereof and satisfies n≥1 and n≥m≥0, and the total of the numbers of the carbon atoms in $R^{A1}$ to $R^{A5}$ or $R^{A6}$ to $R^{A10}$ and $Y^{A1}$ or $Y^{A2}$ is three or more.

In the compound represented by Formula (I-A) or Formula (I-B), foe total number of carbon atoms in $R^{A1}$ to $R^{A5}$ and $Y^{1A}$ or $R^{A6}$ to $R^{A10}$ and $Y^{A2}$ is preferably 25 or less and more preferably 4 to 20. The structure of foe above-described alkyl group may be linear or branched.

$X^{A1}$ and $X^{A2}$ in the compound represented by Formula (I-A) or Formula (I-B) are preferably a sulfonate group or a carboxylate group. In addition, the salt structure in $X^{A1}$ and $X^{A2}$ is preferably an alkali metal salt since the alkali metal salt has a favorable solubility particularly in water-based solvents. Among them, a sodium salt or a potassium salt is particularly preferred.

Regarding the compound represented by Formula (I-A) or Formula (I-B), it is possible to refer to foe description of Paragraphs 0019 to 0037 of JP2007-206348A.

As the anionic surfactant, it is possible to preferably use compounds described in Paragraphs 0023 to 0028 of JP2006-065321A.

The amphoteric surfactant that is used in the developer is not particularly limited, and amine oxide-based surfactants such as alkyldimethylamine oxide, betaine-based surfactants such as alkyl betaine, aliphatic acid amidopropyl betaine, and alkyl imidazole, and amino acid-based surfactants such as sodium alkylamino aliphatic acid.

Particularly, alkyldimethylamine oxide that may have a substituent, alkylcarboxybetaine that may have a substituent, and alkyl sulfobetaine that may have a substituent are preferably used. As specific examples thereof, a compound represented by Formula (2) in Paragraph 0256 of JP2008-203359A, compounds represented by Formula (I), Formula (II), and Formula (VI) in Paragraphs 0028 of JP2008-276166A, and compounds described in Paragraphs 0022 to 0029 of JP2009-047927A can be exemplified.

As an amphoteric ionic surfactant that is used in the developer, a confound represented by General Formula (1) or a compound represented by General Formula (2) is preferred

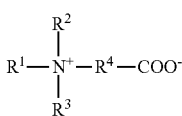 (1)

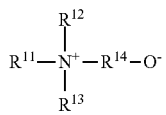 (2)

In General Formulae (1) and (2), $R^1$ and $R^{11}$ each independently represent an alkyl group having 8 to 20 carbon atoms or an alkyl group having a linking group having 8 to 20 carbon atoms in total.

$R^2$, $R^3$, $R^{12}$, and $R^{13}$ each independently represent a hydrogen atom, an alkyl group or a group containing an ethylene oxide.

$R^4$ and $R^{14}$ each independently represent a single bond or an alkylene group.

In addition, two groups of $R^1$, $R^2$, $R^3$, and $R^4$ may be bonded to each other to form a ring structure, and two groups of $R^{11}$, $R^{12}$, $R^{13}$, and $R^{14}$ may be bonded to each other to form a ring structure.

In the compound represented by General Formula (1) or the compound represented by General Formula (2), in a case in which the total number of carbon atoms becomes large, a hydrophobic portion becomes large, and the solubility in water-based developers degrades. In this case, the solubility is improved by mixing an organic solvent such as an alcohol that aids dissolution as a dissolution aid into water; however, in a case in which the total number of carbon atoms becomes too large, it is not possible to dissolve the surfactant in an appropriate mixing range. Therefore, the total of the numbers of carbon atoms in $R^1$ to $R^4$ or $R^{11}$ to $R^{14}$ is preferably 10 to 40 and more preferably 12 to 30.

The alkyl group having a linking group represented by $R^1$ or $R^{11}$ represents a structure in which a linking group is present between alkyl groups. Thai is, in a case in which the number of linking groups is one, the alkyl group can be represented by "-an alkylene group-a linking group-an alkyl group". As the linking group, an ester bond, a carbonyl bond, and an amide bond are exemplified. The number of the linking groups may be two or more, but is preferably ene, and an amide bond is particularly preferred. The total number of carbon atoms in the alkylene group that bonds to the linking group is preferably 1 to 5. This alkylene group may be linear or branched, but is preferably a linear alkylene group. The comber of carbon atoms in the alkyl group that bonds to the linking group is preferably 3 to 19, and the alkyl group may be linear or branched, but is preferably linear alkyl group.

In a case in which $R^2$ or $R^{12}$ is an alkyl group, the number of carbon atoms is preferably 1 to 5 and particularly preferably 1 to 3. The alkyl group may be any of linear or branched, but is preferably a linear alkyl group.

In a case in which $R^3$ or $R^{13}$ is an alkyl group, the number of carbon atoms is preferably 1 to 5 and particularly preferably 1 to 3. The alkyl group may be any of linear or branched, but is preferably a linear alkyl group.

As the group containing an ethylene oxide represented by $R^3$ or $R^{13}$, groups represented by $-R^a(CH_2CH_2O)_nR^b$ can be exemplified. Here, $R^1$ represents a single bond, an oxygen atom, or a divalent organic group (preferably having 10 or less carbon atoms), $R^b$ represents a hydrogen atom or an organic group (preferably having 10 or less carbon atoms), and n represents an integer of 1 to 10.

In a case in which $R^4$ or $R^{14}$ is an alkylene group, the number of carbon atoms is preferably 1 to 5 and particularly preferably 1 to 3. The alkylene group may be any of linear or branched, bat is preferably a linear alkylene group.

The compound represented by General Formula (1) or the compound represented by General Formula (2) preferably has an amide bond and more preferably has an amide bond as the linking group as $R^1$ or $R^{11}$.

Representative of the compound represented by General Formula (1) or the compound represented by General Formula (2) will be illustrated below, but the present invention is not limited thereto.

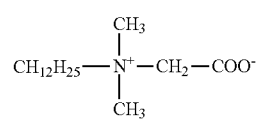
I-a)

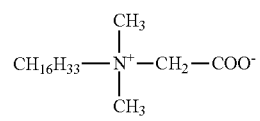
I-b)

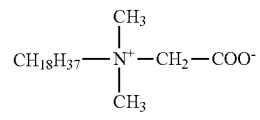
I-c)

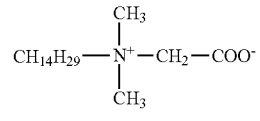
I-d)

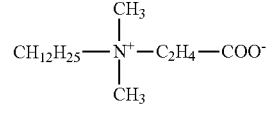
I-e)

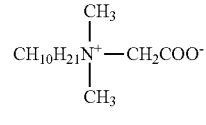
I-f)

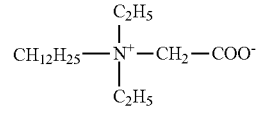
I-g)

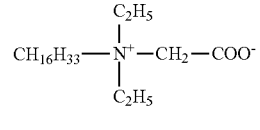
I-h)

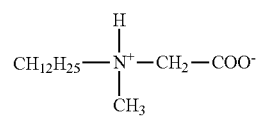
I-i)

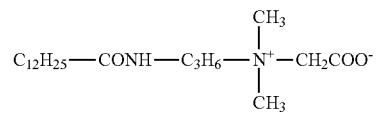
I-j)

-continued

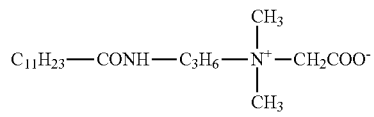
I-k)

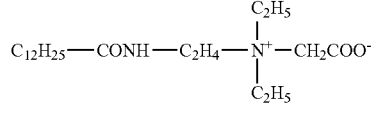
I-l)

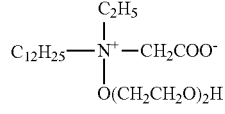
I-m)

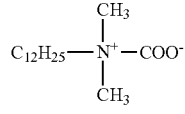
I-n)

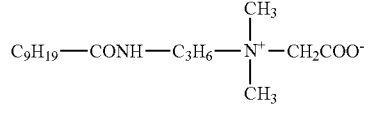
I-o)

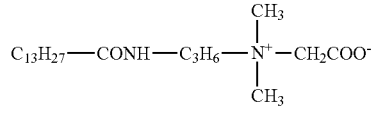
I-p)

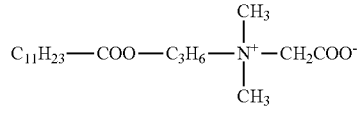
I-q)

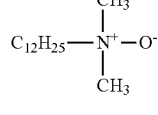
II-a)

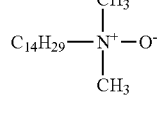
II-b)

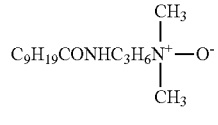
II-c)

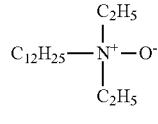
II-d)

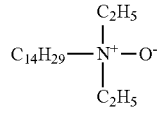
II-e)

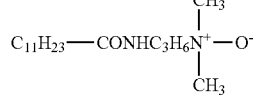
II-f)

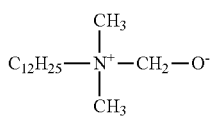

The compound represented by General Formula (1) or (2) can be synthesized using a well-known method. In addition, it is also possible to use commercially available compounds. As the commercially available products of the confound represented by General Formula (1), SOFTAZOLINE LPB, SOFTAZOLINE LPB-R, and BISTA MAP manufactured by Kawaken Fine Chemicals Co., Ltd., TAKESURF C-157L manufactured by Takemoto Oil & Fat Co., Ltd., and the like are exemplified. As the commercially available products of the compound represented by General Formula (2), SOFTAZOLINE LAO manufactured by Kawaken Fine Chemicals Co., Ltd., AMOGEN AOL manufactured by DKS Co., Ltd, and the like are exemplified.

The developer, one amphoteric ionic surfactant may be used singly or two or more amphoteric ionic surfactants may be used in combination.

As nonionic surfactant, polyoxyethylene alkyl ethers, polyoxyethylene alkyl phenyl ethen, polyoxyethylene polystyryl phenyl ether, glycerin aliphatic acid partial esters, sorbitan aliphatic acid partial esters, pentaerythritol aliphatic acid partial esters, propylene glycol mono aliphatic, acid ester, sucrose aliphatic acid partial ester, polyoxyethylene sorbitan aliphatic acid partial esters, polyoxyethylene sorbitol aliphatic acid partial esters, polyethylene glycol aliphatic acid esters, polyglycerin aliphatic acid partial esters, polyoxyethylene glycerin aliphatic acid partial esters, polyoxyethylene diglycerine, aliphatic acid diethanolamides, N,N-bis-2-hydroxyalkylamines, polyoxyethylene alkylamine, triethanolamine aliphatic acid ester, trialkylamine oxide, polyoxyethylene alkyl phenyl ethos, polyoxyethylene-polyoxypropylene blocked copolymers, and the like are exemplified.

In addition, acetylene glycol-based and acetylene alcohol-based oxyethylene adducts and fluorine-based and other surfactants can also be used in the same manner. Two or more surfactants described above can be jointly used.

As the nonionic surfactant, a nonionic aromatic ether-based surfactant represented by Formula (N1) is particularly preferably exemplified.

$X^N—Y^N—O-(A^1)_{nB}-(A^1)_{mB}-H$      (N1)

In the formula, $X^N$ represents an aromatic group dot may have a substituent, $Y^N$ represents a single bond or an alkylene group having 1 to 10 carbon atoms. $A^1$ and $A^2$ are mutually different groups and are represented by any of —$CH_2CH_2O$— or —$CH_2CH(CH_3)O$—, nB and mB each independently represent an integer of 0 to 100; here; nB and mB are not zero at the same time, and, in a case in which any of nB or mB is zero, nB and mB are not one.

In the formula, as the aromatic group as $X^N$, a phenyl group, a naphthyl group, an anthranyl group, and the like are exemplified. These aromatic groups may have a substituent. As the substituent, organic groups having 1 to 100 carbon atoms are exemplified. Meanwhile, in the formula, in a case in which both A and Bare present, the surfactant may be a random or blocked copolymer.

As specific examples of the organic group having 1 to 100 carbon atoms, aliphatic hydrocarbon groups and aromatic hydrocarbon groups which may be saturated or unsaturated and may be linear or branched, for example, an alkyl group, an alkenyl group, an alkynyl group, an aryl group, an aralkyl group, and the like, additionally, an alkoxy group, an aryloxy group, an N-alkylamino group, an N,N-dialkylamino group, an N-arylamino group, an N,N-diarylamino group, an N-alkyl-N-arylamino group, an acyloxy group, a carbamoyloxy group, an N-alkylcarbamoyloxy group, an N-arylcarbamoyloxy group, an N,N-dialkylcarbamoyloxy group, an N,N-diarylcarbamoyloxy group, an N-alkyl-N-arylcarbamoyloxy group, an acylamino group, an N-alkylacylamino group, an N-arylacylamino group, an acyl group, an alkoxycarbonylamino group, an alkoxycarbonyl group, an aryloxycarbonyl group, a carbamoyl group, an N-alkylcarbamoyl group, an N,N-dialkylcarbamoyl group, an N-arylcarbamoyl grasp an N,N-diarylcarbamoyl group, an N-alkyl-N-arylcarbamoyl group, a polyoxyalkylene chain, the above-described organic groups to which a polyoxyalkylene chain bonds, and the like. The alkyl group may be linear or branched.

In addition, as the nonionic surfactant, it is possible to preferably use compounds described in Paragraphs 0030 to 0040 of JP2006-065321A.

The cationic surfactant is not particularly limited, and well-known cationic surfactants in the related art can be used. For example, alkylamine salts, quaternary ammonium salts, alkyllimidazolinium salts, polyoxyethylene alkylamine salts, polyethylene polyamine derivatives, and the like are exemplified.

The surfactant may be used singly or two or mote surfactants may be jointly used. The content of the surfactant is preferably 1% by mass to 25% by mass, more preferably 2% by mass to 20% by mass, still more preferably 3% by mass to 15% by mass, and particularly preferably 5% by mass to 10% by mass of the total mass of the developer. In a case in which the content of the surfactant is in the above-described range, the scratch stain resistance is superior, the dispersibility of development scum is excellent, and the ink-absorbing property of lithographic printing plates to be obtained is excellent.

[Water-Soluble Polymer Compound]

From the viewpoint of adjusting the viscosity of the developer and protecting the plate surface of a lithographic printing plate to be obtained the developer may include a water-soluble polymer.

As a water-soluble polymer, the developer may contain a water-soluble polymer compound such as a soy polysaccharide, modified starch, gum arabic, dextrin, a fibrin derivative (for example, carboxymethyl cellulose, carboxyethyl cellulose, methyl cellulose, or the like) and a modified product thereof pullulan, polyvinyl alcohol and a derivative thereof polyvinyl pyrrolidone, polyacrylamide and an acrylamide copolymer, a vinyl methyl ether/maleic anhydride copolymer, a vinyl acetate/maleic anhydride copolymer, or a styrene/maleic anhydride copolymer.

As the soy polysaccharide, soy polysaccharides known in the related art can be used, and, for example, as commercially available products, there is SOYAFIBE (trade name, manufactured by Fuji Oil Co., Ltd), and it is possible to use a variety of grades of soy polysaccharides. Soy polysaccharides feat can be preferably used have a viscosity of a 10% by mass aqueous solution in a range of 10 mPa·s to 100 mPa·s.

As the modified starch, starch represented by Formula (III) is preferred. As the starch represented by Formula (III), any starch such as corn, potato, tapioca, rice, or wheat can be used. The starch can be modified using a method in which starch is decomposed using an acid, an enzyme, or the like to the number of glucose residues per molecule in a range of 5 to 30 and, furthermore, oxypropylene is added thereto in an alkali

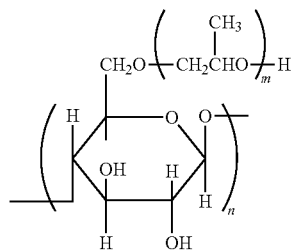

(III)

In the formula, the degree of etherification (degree of substitution) is in a range of 0.05 to 1.2 per glucose unit, n represents an integer of 3 to 30, and m represents an integer of 1 to 3.

Among water-soluble polymer compounds, soy polysaccharides, modified starch, gum Arabic, dextrin, carboxymethyl cellulose, polyvinyl alcohol, and the like are particularly preferred.

Two or more water-soluble polymer compounds can be jointly used.

The developer preferably contains no water-soluble polymer compound or contains a water-soluble polymer compound in a content of more than 0% by mass and 1% by mass or less of toe total mass of the developer, more preferably contains no water-soluble polymer compound or contains a water-soluble polymer compound in a content of more dun 0% by mass and 0.1% by mass or less of the total mass of the developer, still more preferably contains no water-soluble polymer compound or contain a water-soluble polymer compound in a content of more than 0% by mass and 0.05% by mass or less of the total mass of the developer, and particularly preferably contains no water-soluble polymer compound. In the above-described aspect, the viscosity of the developer is appropriate, and it is possible to suppress the deposition of development scum or the like in a roller member such as an automatic developing machine.

[Other Additives]

The developer that is used in the present invention may contain, in addition to the above-described components, a wetting agent, a preservative, a chelate compound a defoamer, an organic acid an organic solvent, an inorganic acid an inorganic salt, or the like.

As the wetting agent, ethylene glycol, propylene glycal, triethylene glycol, butylene glycol, hexylene glycol, diethylene glycol, dipropylene glycol, glycerin, trimethylolpropane, diglycerin, and the like are preferably used. The wetting agent may be used singly or two or more wetting agents may be jointly used. The content of the wetting agent is preferably 0.1% by mass to 5% by mass of the total mass of the developer.

As the preservative, phenol or a derivative thereof, formalin an imidazole derivative, sodium dehydroacetate, a 4-isothiazolin-3-one derivative, benzisothiazolin-3-one, 2-methyl-4-isothiazolin-3-one, a benzotriazole derivative, an amidine guanidine derivative, a quaternary ammonium salt, a derivative of pyridine, quinoline, guanidine, or the like, diazine, a triazole derivative, oxazole, an oxazine derivative, nitrobromo alcohol-based 2-bromo-2-nitropropane-1,3-diol, 1,1-dibromo-1-nitro-2-ethanol, 1,1-dibromo-1-nitro-2-propanol, or the like can be preferably used.

The amount of the preservative added needs to be an amount in which the preservative stably exhibits an effect with respect to bacteria, fungi, yeast, and the like and which varies depending cm the kind of bacteria, fungi, and yeast and is preferably in a range of 0.01% by mass to 4% by mass of the total mass of the developer. In addition, two or more preservatives are preferably jointly used so as to be effective to a variety of fungi and bacteria.

As the chelate compound, for example, ethylenediaminetetraacetic acid, potassium salts thereof and sodium salts thereof diethylenetriaminepentaaceitc acid, potassium salts thereof and sodium salts thereof; triethylenetetraminehexaacetic acid, potassium salts thereof and sodium salts thereof hydroxyethylethylenediaminetriacetic acid, potassium salts thereof and sodium salts thereof nitrilotriacetic acid, and sodium salts thereof; 1-hydroxyethane-1,1-diphosphonic acid, potassium salts thereof and sodium salts thereof; and organic phosphonic acids such as aminotri (methylene phosphonate), potassium salts thereof and sodium salts thereof can be exemplified. Instead of sodium salts and potassium salts of chelating agents, salts of organic amines are also effective.

The chelating agent is preferably a chelating agent that is stably present in a process liquid composition and does not impair a printing property. The content of the chelating agent is preferably 0.001% by mass to 1.0% by mass of the total mass of the developer.

As the defoamer, it is possible to use an ordinary silicone-based self-emulsification-type, emulsification-type, or non-ionic compound having a hydrophilic-lipophilic balance (HLB) of 5 or less. A silicone defoamer is preferred.

Meanwhile, a silicone-based surfactant is regarded as the defoamer.

The content of the defoamer is preferably in a range of 0.001% by mass to 1.0% by mass of the total mass of the developer.

As the organic acid, citric acid, acetic acid, oxalic acid, malonic acid, salicylic acid, caprylic acid, tartaric acid, malic acid, lactic acid, levulinic acid, p-toluenesulfonic acid, xylenesulfonic acid, phytic acid, organic phosphonic acid, and the like are exemplified. The organic acid can also be used in a form of an alkali metal salt or ammonium salt thereof. The content of the organic acid is preferably 0.01% by mass to 0.5% by mass of the total mass of the developer.

As the organic solvent, for example, aliphatic hydrocarbons (hexane, heptane, "ISOPAR E, H, G" (manufactured by Esso Chemical Co., Ltd.) and the like), aromatic hydrocarbons (toluene, xylene, and the tike), halogenated hydrocarbons (methylene dichloride, ethylene dichloride, trichloroethylene, monochlorobenzene, and the like), polar solvents, and the like are exemplified.

As the polar solvents, alcohols (methanol, ethanol, propanol, isopropanol, benzyl alcohol, ethylene glycol monomethyl ether, 2-ethoxyethanol, diethylene glycol monoethyl ether, diethylene glycol monohexyl ether, triethylene glycol monomethyl ether, propylene glycol monoethyl ether, propylene glycol monomethyl ether, polyethylene glycol monomethyl ether, polypropylene glycol, tetraethylene glycol, ethylene glycol monobutyl ether, ethylene glycol monobenzyl ether, ethylene glycol monophenyl ether, methyl phenyl carbinol, n-amyl alcohol, methyl amyl alcohol, and the hire), ketones (acetone, methyl ethyl ketone, ethyl butyl ketone, methyl isobutyl ketone, cyclohexanone, and the tike), esters (ethyl acetate, propyl acetate, butyl acetate, amyl acetate, benzyl acetate, methyl lactate, butyl lactate, ethylene glycol monobutyl acetate, propylene glycol monomethyl ether acetate, diethylene glycol acetate, diethyl phthalate, butyl levulinate, and the like), other polar solvents (triethyl phosphate, tricresyl phosphate, N-phenylethanolamine, N-phenyldiethanolamine, and the like), and the like are exemplified.

In a case in which the organic solvent is not soluble in water, it is also possible to make the organic solvent soluble in water using a surfactant or the like and then use the organic solvent, and, in a case in which the developer contains the organic solvent, from the viewpoint of safety and inflammability the concentration of the solvent in the developer is preferably less than 40% by mass.

As the inorganic acid and the inorganic salt, phosphoric acid, metaphosphoric acid, primary ammonium phosphate, secondary ammonium phosphate, primary sodium phosphate, secondary sodium phosphate, primary potassium phosphate, secondary potassium phosphate, sodium tripolyphosphate, potassium pyrophosphate, sodium hexametaphosphate, magnesium nitrate, sodium nitrate, potassium nitrate, ammonium nitrate, sodium sulfate, potassium sulfate, ammonium sulfate, sodium sulfite, ammonium sulfite, sodium hydrogen sulfate, nickel sulfite, and the like are exemplified. The content of the inorganic salt is preferably 0.01% by mass to 0.5% by mass of the total mass of the developer.

The developer is prepared by dissolving or dispersing the respective components described above in water as necessary. The concentration of the solid content of the developer is preferably 2% by mass to 25% by mass. As the developer, it is also possible to produce a concentrated liquid and, at the time of being used, dilute the concentrated liquid with water.

The developer is preferably an aqueous developer.

From the viewpoint of the dispersibility of development scum, the developer preferably contains an alcohol compound.

As the alcohol compound, methanol, ethanol, propanol, isopropanol, benzyl alcohol, and the like are exemplified. Among these, benzyl alcohol is preferred.

The content of the alcohol compound is preferably 0.01% to 5% by mass, more preferably 0.1% to 2% by mass, and particularly preferably 0.2% to 1% by mass of the total mass of the developer from the viewpoint of the dispersibility of development scum, Examples Hereinafter, the present invention will be described in detail using examples, but the present invention is not limited thereto. Meanwhile, for polymer compounds, unless particularly otherwise described, the molecular weight refers to the weight-average molecular weight (Mw) converted to a polystyrene equivalent value by the gel permeation chromatography (GPC) method, and the ratio of a repeating unit refers to the molar percentage. In addition, "parts" and "%" indicate "parts by mass" and "% by mass" unless particularly otherwise described. Meanwhile, Me represents a methyl group.

Synthesis Example 1: Synthesis of Compound 1

(Synthesis of Intermediate SM-5)
The synthesis scheme of an intermediate SM-5 will be illustrated below.

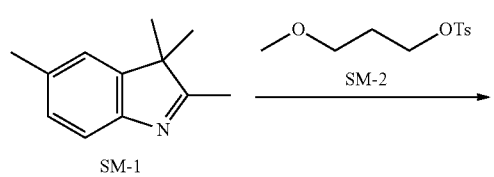

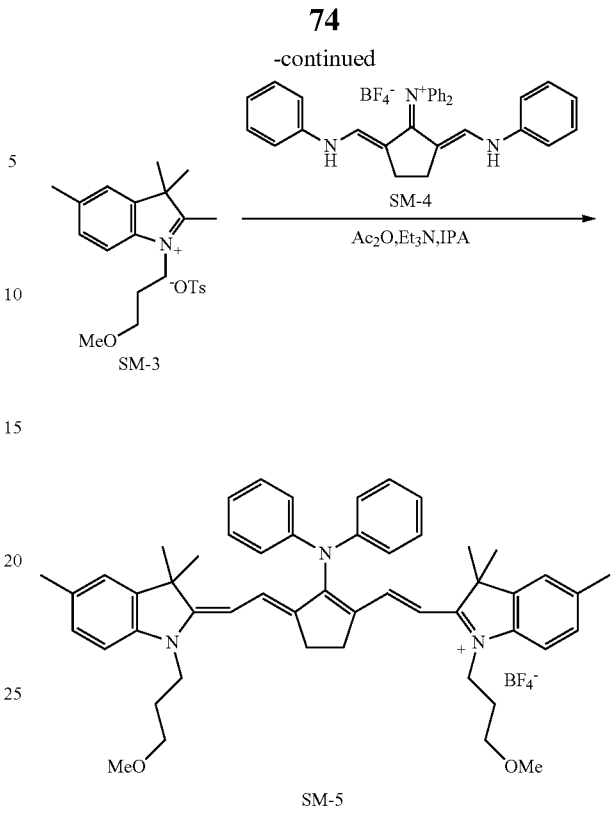

5-Methyl-2,3,3-trimethylindolenine (SM-1) (2172 g, 1.12 mol) and 3-methoxypropyl tosylate (SM-2) (305.7 g, 1-25 mol) were added to a 3 L three-neck flask and stirred at 120° C. for 3.5 hours, thereby obtaining an intermediate SM-3. This reaction liquid was cooled to 60° C., and then isopropanol (976.3 g) was added thereto and stirred at 40° C., Furthermore, SM-4 (265.0 g, 0.50 mol) and an acetic anhydride (127.8 g, 1.25 mol) were added thereto. After triethylamine (316.6 g, 3.13 mol) was added dropwise (hereto and stirred at 80° C. for two hours. This reaction liquid was cooled to 5° C., and distilled water (500 g) was added thereto and stirred for one hour. The precipitated solid was collected by filtration, washed with distilled water (1,000 g), and then dried in an air blast dryer set to 50° C. for eight hours, thereby obtaining an intermediate SM-5 (336.4 g, 0.40 mol).

(Synthesis of Intermediate SM-6)

The synthesis scheme of an intermediate SM-6 will be illustrated below

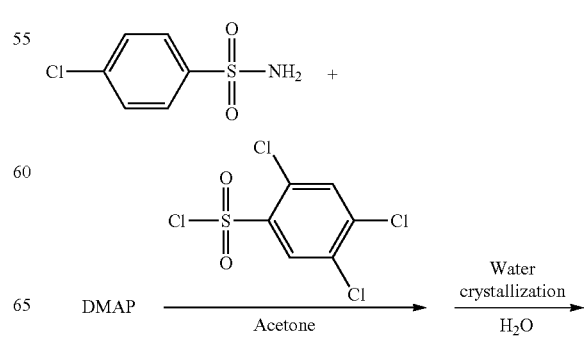

-continued

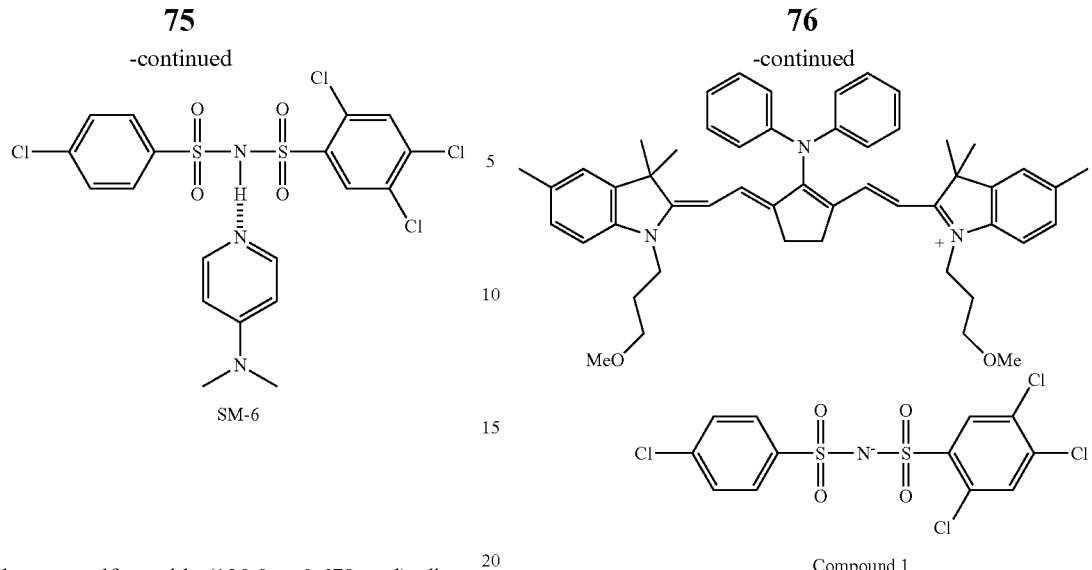

Compound 1 p-Chlorobenzenesulfonamide (130.0 g, 0.678 mol), dimethylaminopyridine (165.8 g, 1.36 mol), and acetone (590 ml) were added to a 3 L three-neck flask and dissolved al 35° C. Next, 2,4,5-trichiorobenzenesulfonic acid chloride (189.9 g, 0.678 mol) was dissolved in acetone (400 ml), added dropwise thereto while maintaining an inner temperature al 50° C. or lower, and, after the end of the dropwise addition, stirred at the timer temperature of 50° C. for two hours.

After the end of the reaction, water (1,600 ml) was added thereto and stirred at room temperature for one hour. After that, the precipitated solid was collected by filtration, washed with distilled water (1,000 g), and then dried in an air Mart dryer set to 50° C. for eight hours, thereby obtaining an intermediate SM-6 (317.4 g, 0.57 mol).

(Synthesis of Compound 1)

The synthesis scheme of a compound 1 will be illustrated below.

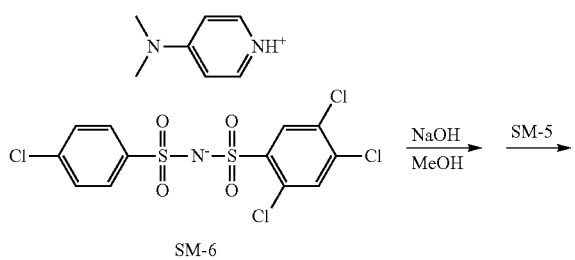

The intermediate SM-6 (189.7 g, 0.34 mM) and methanol (1,200 g) were added to a 3 L three-neck flask and stirred al 60° C. A 50% by mass aqueous solution of sodium hydroxide (24.8 g, 0.31 mol) was added thereto and stored for 30 minutes, and foe reaction temperature was set to 40° C. The intermediate SM-5 (258.0 g, 0.31 mol) and methanol (638 g) were further added thereto and stirred at 40° C. for 30 minutes. The reaction liquid was added dropwise to a 12 L stainless steel beaker to which distilled water (2,700 g) and methanol (300 g) weir added and, after the end of the dropwise addition, stirred for 30 minutes. The precipitated solid was collected by filtration and washed with distilled water (2 LX an acetone/distilled water-mixed liquid (volume ratio: 2/3) (5 L), and, furthermore, an ethyl acetate/hexane-mixed liquid (volume ratio: 1/3) (5 L). The obtained solid was dried in an air blast dryer set to 50° C. for 48 hours, thereby obtaining a compound 1 (358.0 g, 0.30 mol). The structure of the obtained compound 1 was identified by NMR. The identification result will be described below.

$^1$H-NMR (400 MHz, heavy dimethyl sulfoxide) δ=1.10 (s, 12H), 1.83-1.94 (m, 4H), 2.30 (s, 6H), 2.88 (s, 4H), 3.20 (s, 6H), 3.29-3.33 (m, 4H), 4.04 (t, 4H), 5.84 (d, 2H), 7.06-7.16 (m, δH), 7.18-7.25 (m, δH), 7.37-7.47 (m, 8H), 7.56 (d, 2H), 7.74 (s, 1H), 7.77 (s, 1H)

Synthesis Example 2: Synthesis of Compound 2

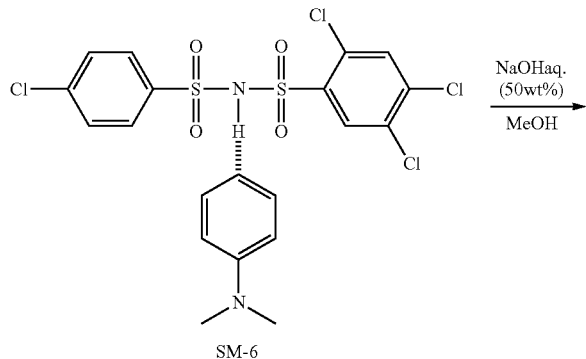

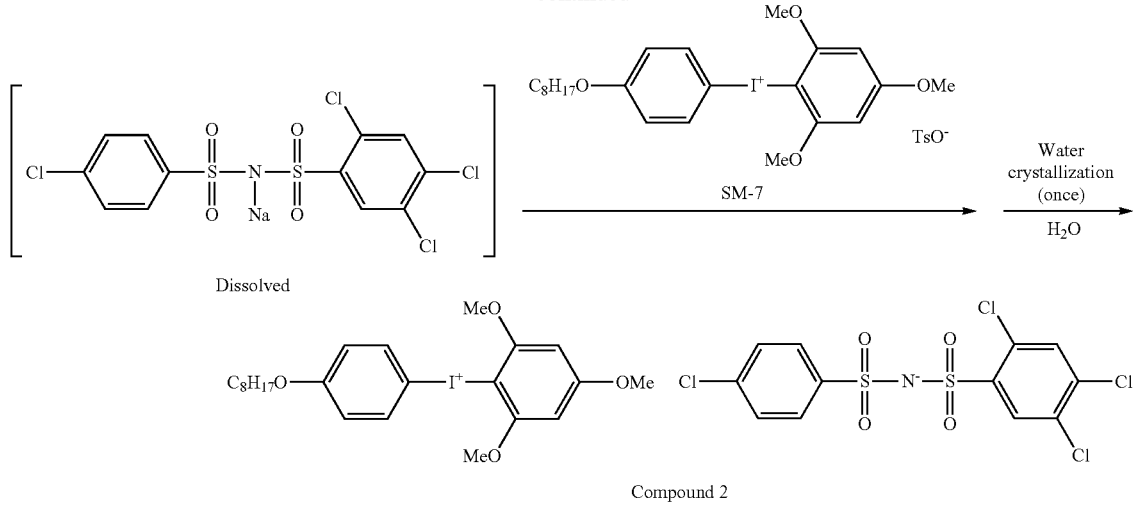

Compound 2

The intermediate SM-6 (2.23 g, 0.004 mol) and methanol (20 ml) were added to a 100 L three-neck flask, and, furthermore, a 50% by mass aqueous solution of sodium hydroxide (0.32 g, 0.008 mol) was added thereto and stirred for 30 minutes, thereby dissolving SM-6. Next SM-7 foal could be synthesized using a well-known method (1.34 g, 0.002 mol) was added thereto and dissolved. Wider (10 ml) was added thereto and stirred for one hour. After that foe precipitated solid was collected by filtration, washed with distilled water (20 g), and dried at room temperature, thereby obtaining a compound 2 (1.8 g, 0.0019 mol).

The structure of the obtained compound 2 was identified by NMR. The identification result will be described below.

$^1$H-NMR (400 MHz, heavy dimethyl sulfoxide) δ=0.85 (m, 3H), 1.17-1.4 (m, 10H), 1.67 (m, 2H), 3.16 (d, 4H), 3.85 (s, 3H), 3.90-4.00 (m, δH), 4.10 (q, 4H), 6.44 (s, 2H), 6.98 (d, 2H), 7.39 (m, 2H), 7.55 (m, 2H), 7.76 (d, 2H), 7.82 (d, 2H)

Example 101 to 118 and Comparative Examples 101 to 104

[Production of Lithographic Printing Plate Precursor A]
<Production of Support>

In order to remove rolling oil on the surface of a 0.3 mm-thick aluminum plate (material JIS A 1050), a defatting process was earned out thereon using a 10% by mass aqueous solution of sodium aluminate at 50° C. for 30 seconds. After that, the surface of the aluminum plate was grained using three implanted nylon brushes having hair diameter of 0.3 mm and a suspension of pumice having a median diameter of 25 μm and water (specific gravity: 1.1 g/cm$^3$) and well washed with water. The aluminium plate was etched by being immersed in a 25% by mass aqueous solution of sodium hydroxide at 4° C. for nine seconds, was washed with water, then, was further immersed in a 20% by mass aqueous solution of nitric acid at 60° C. for 20 seconds, and was washed with water. The etched amount of the grained surface was approximately 3 g/m$^2$.

Next, an electrochemical roughening process was continuously carried out thereon using an alternating current voltage of 60 Hz. An electrolytic solution was a 1% by mass aqueous solution of nitric acid (including 0.5% by mass of aluminum ions), and the liquid temperature was 50° C. The electrochemical roughening process was carried out thereon using an alternating current power supply waveform in which the time TP taken for the current value to reach the peak from zero was 0.8 msec and the duty ratio was 1:1, and the electrochemical roughening process was carried out using a trapezoidal rectangular wave alternating current and a carbon electrode as a counter electrode. As an auxiliary anode, ferrite was used. The current density was 30 A/dm$^2$ in terms of the peak value of the current, and 5% of the current coming from the power supply was divided into the auxiliary anode. Regarding the quantity of electricity during nitric acid electrolysis, the quantity of electricity was 175 C/dm$^2$ in a case in which the aluminium plate served as the positive electrode. After that, the plate was washed with water by means of spraying.

Subsequently, an electrochemical roughening process was carried out thereon using the same method as nitric acid electrolysis in a 0.5% by mass aqueous solution of hydrochloric acid (including 0.5% by mass of aluminium ions) and an electrolytic solution having a liquid temperature of 50° C. under a condition of the quantity of electricity of 50 C/dm$^2$ in a case in which the aluminum plate served as the positive electrode, and then, the plate was washed wife water by means of spraying.

Next, 2.5 g/m$^2$ of a direct current anodized film was formed on the aluminum plate at a current density of 15 A/dm$^2$ using a 15% by mass aqueous solution of sulfane acid (including 0.5% by mass of aluminum ions) as an electrolytic solution, and water washing and drying were carried out thereon, thereby producing a support A. The average pore diameter of the surface layer of the anodized film (surface average pore diameter) was 10 nm.

The pore diameter of the surface layer of the anodized film was measured using a method in which the surface was observed an ultrahigh resolution SEM (S-900 manufactured by Hitachi, Ltd.) at a relatively low acceleration voltage of 12 V at a magnification of 150,000 times without carrying out a vapor deposition process or the like for imparting conductive properties, 50 pores woe randomly extracted, and the average value was obtained. The standard deviation error was ±10% or less.

After that, in order to ensure the hydrophilicity of a non-image area, a silicate process was carried out on the support A using a 2.5% by mass aqueous solution of No. 3 sodium silicate at 60° C. for ten seconds, and the support was washed with water, thereby producing a support B. The attached amount of Si was 10 mg/m². The center line average roughness (Ra) of the support B was measured using a needle having a diameter of 2 μm and was found to be 0.51 μm.

A support C was produced in the same manner as in the method for producing the support A except for the fact that, in the production of the support A, the electrolytic solution in the formation of the direct current anodized film was changed to a 22% by mass aqueous solution of phosphoric acid. The average pore diameter on the surface layer of the anodized film (surface average pore diameter) was measured using the same method as described above and found out to be 25 nm.

After that, a silicate process was carried out on the support C using a 2.5% by mass aqueous solution of No. 3 silicate soda at 60° C. for 10 seconds in order to ensure the hydrophilicity of a non-image area and then washed wife water, thereby producing a support D. The amount of Si attached was 10 mg/m². The center line average roughness (Ra) of the support D was measured using a needle having a diameter of 2 μm and found out to be 0.52 μm Formation of Undercoat Layer>

A coating fluid for an undercoat layer (1) having the following composition was applied onto the support A so that the dried coating amount reached 20 mg/m², thereby forming an undercoat layer.

(Coating Fluid for Undercoat Layer (1))
Polymer (P-1) [illustrated below]: 0.18 g
Hydroxyethyl iminodiacetic acid: 0.10 g
Water: 614 g to a stainless steel beaker, ethyl acetate (3,320 parts), methyl-tert butyl ether (MTBE) (1,120 parts), and distilled water (650 parts) were added thereto, and the components were strongly stirred and then left to stand. The upper layer (organic layer) was disposed of then, ethyl acetate (1,610 parts, 1.8 L) was added thereto, the components were strongly stirred and then left to stand, and the upper layer was disposed of. Furthermore, ethyl acetate (1,350 parts) was added thereto, the components were strongly stirred and then left to stand, and the upper layer was disposed of. Next, MTBE (1,190 parts) was added thereto, the components were strongly stirred and then left to stand, and the upper layer was disposed of, 4-OH-TEMPO (0.063 parts) was added to the obtained aqueous solution, thereby obtaining an aqueous solution of a monomer M-1 (12,000 parts, 20.1% by mass in terms of the solid content).

(Purification of Monomer M-2)

LIGHT ESTER P-1M (2-methacryloyloxyethyl acid phosphate, manufactured by Kyoeisha Chemical Co., Ltd.) (420 parts), diethylene glycol dibutyl ether (1,050 parts), and distilled water (1,050 parts) were added to a separating funnel, strongly stirred, and then left to stand. The upper layer was disposed of diethylene glycol dibutyl ether (1,050 parts) was added thereto, and the components wens strongly stirred and then left to stand. The upper layer was disposed of thereby obtaining an aqueous solution of a monomer M-2 (13,000 parts, 10.5% by mass in terms of the solid content).

(Synthesis of Polymer P-1)

Distilled water (600.6 parts), the aqueous solution of the monomer M-1 (33.1 parts), and a monomer M-3 described below (46.1 parts) were added to a three-neck flask and healed to 55° C. in a nitrogen atmosphere. Next, the fol-

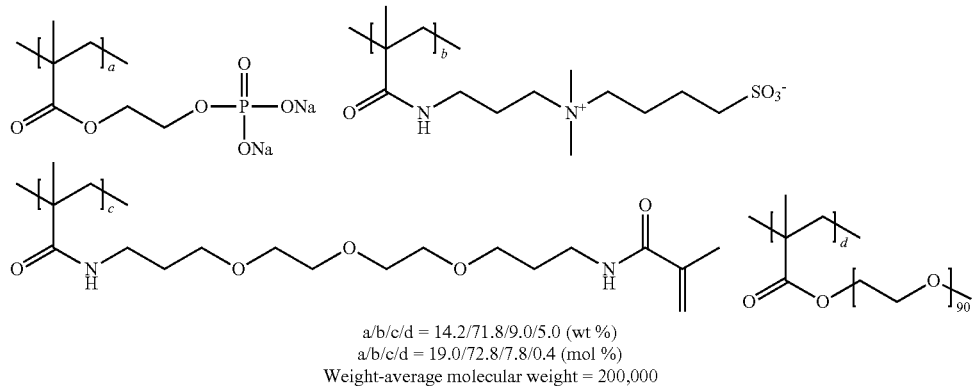

(P-1)

a/b/c/d = 14.2/71.8/9.0/5.0 (wt %)
a/b/c/d = 19.0/72.8/7.8/0.4 (mol %)
Weight-average molecular weight = 200,000

A method for synthesizing the polymer (P-1) will be described below.

(Synthesis of Monomer M-1)

ANCAMINE 1922A (diethylene glycol diaminopropyl) ether, manufactured by Air Products) (200 parts), distilled water (435 parts), and methanol (410 parts) were added to a three-neck flask and cooled to 5° C. Next, benzoic acid (222.5 parts) and 4-hydroxy-2,2,6,6-tetramethylpiperidine-1-oxyl (4-OH-TEMPO) (0.025 parts) were added thereto, and a methacrylic anhydride (280 parts) was added dropwise thereto so that foe inner temperature of foe reaction liquid reached 10° C. or lower. The reaction liquid was starred at 5° C. for six hours and, subsequently, stirred at 25° C. for 12 hours, and then phosphoric acid (70 parts) was added thereto so as to adjust the pH to 3.3. The reaction liquid was moved lowing dropwise addition liquid 1 was added dropwise thereto for two hours, the components were stirred for 30 minutes, then, VA-046B (manufactured by Wako Pure Chemical Corporation) (3.9 parts) was added thereto, and the components were heated to 80° C. and stirred for 1.5 hours. The reaction liquid was returned to room temperature (25° C., which shall apply below), and then a 30% by mass aqueous solution of sodium hydroxide (175 parts) was added thereto, thereby adjusting the pH to 8.3. Next, 4-QH-TEMPO (0.152 parts) was added thereto, and the components were heated to 53° C. A methacrylic anhydride (66.0 parts) was added thereto, and the components were stirred at 53° C. for three hours. The components were returned to room temperature, then, the reaction liquid was moved to a stainless steel beaker, MTBE (1,800 parts) was added thereto, the components were strongly stirred and then left to stand, and the upper layer was disposed of. A washing operation using MTBE (1,800 parts) was further repeated twice in the same manner, and then distilled water (1,700 parts) and 4-OH-TEMPO (0.212 parts) were added to the obtained water layer, thereby obtaining a polymer P-1 (41,000 parts, 11.0% in terms of the solid content) as a homogeneous solution. The weight-average molecular weight (Mw) converted to a polyethylene glycol equivalent value by the gel permeation chromatography (GPC) method was 200,000.

Dropwise Addition Liquid 1
The aqueous solution of the monomer M-1: 132.4 g
The aqueous solution of the monomer M-2: 376.9 g
Monomer M-3 [illustrated below]: 184.3 g
BREMMER PME 4000 (manufactured by NOF Corporation): 15.3 g
VA-046B (manufactured by Wako Pure Chemical Corporation): 3.9 g
Distilled water 717.4 g
BREMMER PME 4000: Methoxy polyethylene glycol methacrylate (the number of the oxyethylene unit repeated: 90)
VA-046B: 2,2'-Azobis[2-(2-imidazolin-2-yl)propane]disulfide dihydrate Monomer M-3

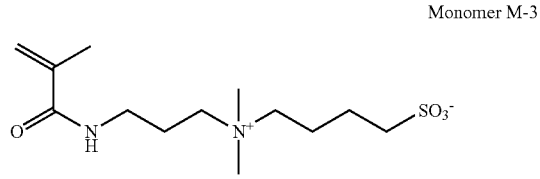

<Formation of Image-Recording Layer>

A coating fluid for an image-recording layer (1) having the following composition was applied onto the undercoat layer by means of bar coating and was dried in an oven at 100° C. for 60 seconds, thereby forming an image-recording layer having a dried coating amount of 1.0 g/m².

The coating fluid for the image-recording layer (1) was prepared by mixing and stirring the following photosensitive liquid (I) and a micro gel liquid immediately before the application.

| <Photosensitive liquid (1)> | |
|---|---|
| Binder polymer (1) [illustrated below] | 0.240 g |
| Infrared absorber (D-I) [illustrated below] | 0.024 g |
| Specific compound shown in Table I or well-known compound (polymerization initiator) | 0.245 g |
| Polymerizable compound | 0.192 g |
| Tris(arryloyloxyetlayl)isocyanurate (NK ester A-9300: manufactured by Shin-Nakamura Chemical Co., Ltd.) | |
| Low-molecular-weight hydrophilic compound: Tris(2-hydroxyethyl)isocyanurate | 0.062 g |
| Fluurine-based surfactant (1) [illustrated below] | 0.008 g |
| 2-Butanone | 1.091 g |
| 1-Methoxy-2-propanol | 8.609 g |

<Micro Gel Liquid>
Micro gel (1): 2.640 g
Distilled water: 2.425 g

The structures of the infrared absorber (D-1), the binder polymer (1), and the fluorine-based surfactant (1) which were used for the photosensitive liquid (1) will be illustrated below. In the binder polymer (1), numbers on the lower right side of parentheses of individual constitutional units represent molar ratios.

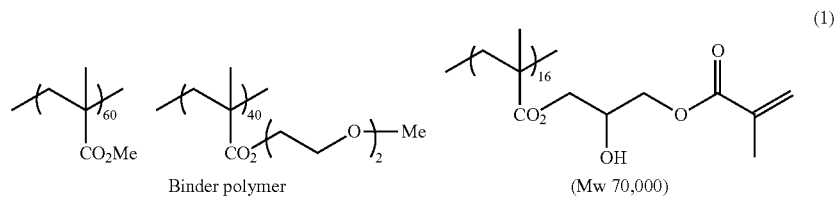

Binder polymer (1) (Mw 70,000)

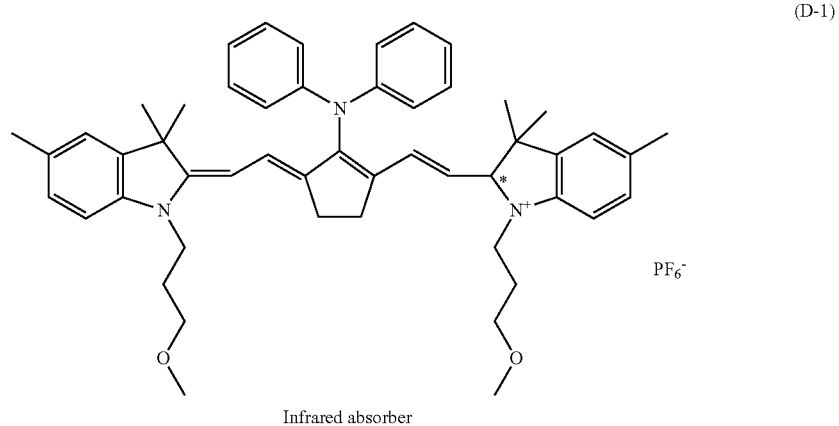

Infrared absorber (D-1)

-continued

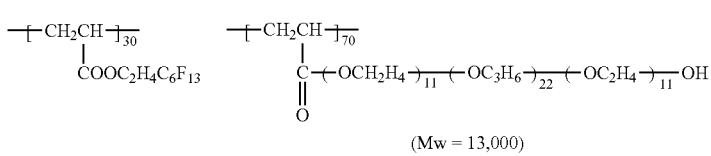

(Mw = 13,000)

Fluorine-based surfactant

A method for preparing a micro gel (1) used for the micro gel liquid will be described below.

<Preparation of Polyhydric Isocyanate Compound (1)>

Bismuth tris(2-ethylhexanoate) (NEOSTAN U-600, manufactured by Nitto Kasei Co., Ltd) (43 mg) was added to an ethyl acetate (25.31 g) suspended solution of isophorone diisocyanate (17.78 g, 80 mmol) and the following polyhydric phenol compound (1) (7.35 g, 20 mmol), and the components were stirred. The reaction temperature was set to 50° C. in a case in which the generation of heat settled, and the components were stored for three hours, thereby obtaining an ethyl acetate solution of a polyhydric isocyanate compound (1) (50% by mass).

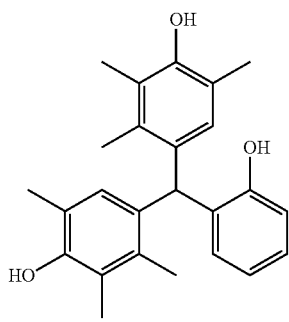

compound (1)

Polyhydric phenol

<Preparation of Micro Gel (1)>

Oil-phase components described below and a water-phase component described below were mixed together and emulsified at 12,000 rpm for 10 minutes using a homogenizer. The obtained emulsion was stored at 45° C. for four hours, a 10% by mass aqueous solution of 1,8-diazabicyclo[5.4.0] undec-7-ene-octanoic acid salt (U-CAT SA102, manufactured by San-Apro Ltd.) (5.20 g) was added thereto, and the components were stirred at room temperature for 30 minutes and left to stand at 45° C. for 24 hours. Adjustment was made using distilled water so that the concentration of the solid content reached 20% by mass, thereby obtaining a water dispersion liquid of a micro gel (1). The volume average particle diameter was measured using a dynamic light scattering-type particle size distribution analyzer LB-500 (manufactured by Horiba Ltd.) and the light scattering method and found out to be 0.28 μm.

(Oil-Phase Components)

(Component 1) Ethyl acetate: 12.0 g (Component 2) An adduct obtained by adding trimethylolpropane (6 mol) and xylene diisocyanate (18 mol) and adding methyl single polyoxy ethylene (1 mol, the number of the oxyethylene unit repeated: 90) thereto (a solution of 50% by mans of ethyl acetate, manufactured by Mitsui Chemicals Inc.): 3.76 g (Component 3) Polyhydric isocyanate compound (1) (as a solution of 50% by mass of ethyl acetate): 15.0 g (Component 4) An ethyl acetate solution of 65% by mass of dipentaerythritol pentaacrylate (SR-399, Sartomer Japan Inc.), 11.54 g (Component 5) An ethyl acetate solution of 10% of a sulfonate-type surfactant (BIONINE A-41-C, manufactured by Takcmoto Oil & Fat Co., Ltd.): 4.42 g (Water-Phase Component)

Distilled water 46.87 g

[Evaluation of Lithographic Printing Plate Precursors]

For the respective lithographic printing plate precursors A described above, the on-machine developability, the thermal and temporal stability (1), and the printing resistance were evaluated using the following evaluation methods. The evaluation results are shown in Table 1.

<On-Machine Developability>

The lithographic printing plate precursors were exposed using a LUXEL PLATESETTER T-6000III manufactured by Fujifilm Corporation which was equipped with an infrared semiconductor laser under conditions of an external surface dram rotation speed of 1.000 rpm, a laser output of 70%, and a resolution of 2,400 dpi. Exposed images were provided with solid images and 50% halftone dot charts of 20 μm dot FM screens.

Without carrying out a development process on the exposed lithographic printing plate precursors, the lithographic printing plate precursors were attached to the plate trunk of a printer LITHRONE 26 manufactured by Komori Corporation. Dampening water and ink were supplied using dampening water of ECOLTTY-2 (manufactured by Fujifilm Corporation)/tap water=2/98 (capacity ratio) and Values-G (N) BLACK INK (manufactured by DIC Graphics Corporation) and using the standard automatic printing start method of LITHRONE 26, and then printing was carried out on 100 pieces of TOKUBISHI art paper (76.5 kg) (manufactured by Mitsubishi Paper Mills limited) at a printing rate of 10,000 pieces per hour.

The on-machine development of non-exposed portions in the image-recording layer was completed on the printer, and the number of pieces of printing paper required until ink was not transferred to the non-image areas was measured and evaluated as the on-machine developability. A smaller number of pieces of printing paper indicates superior on-machine developability.

<Thermal and Temporal Stability (1)>

The lithographic printing plate precursor was adjusted in humidity in an environment of 25° C. and 60% for one hour and then packed. Next, the packed matter was thermally aged at 60° C. for four days. After the end of the thermal aging, in the same manner as in the evaluation of the on-machine developability, image exposure and on-machine development were carried out, the number of pieces of printing paper was measured, and the thermal and temporal stability (1) was evaluated. A smaller number of pieces of printing paper indicates superior thermal and temporal stability.

[Printing Resistance]

After the on-machine developability were evaluated, printing was further continued. As the number of pieces of printed paper increased, the image-recording layer gradually wore, and thus the ink concentration on printed matters decreased. The number of pieces of printed paper until the value of the halftone dot area ratio of FM screen 50% halftone dots on printed matters measured using a gretag density meter decreased to be 5% lower than the measurement value of a $100^{th}$ piece of paper was measured. The printing resistance was evaluated using relative printing resistance for which the number of pieces of printed paper of 50,000 was considered as 100 as shown in the following expression. A larger numerical value indicates superior printing resistance.

Relative printing resistance=((the number of pieces of printed paper of the subject lithographic priming plate precursor)/50,000)×100

TABLE 1

| | Specific compound (polymerization initiator) | On-machine developability (number of pieces) | Thermal and temporal stability (1) (number of pieces) | Printing resistance |
|---|---|---|---|---|
| Example 101 | I-1-j-1 | 25 | 35 | 80 |
| Example 102 | I-3-j-1 | 35 | 25 | 75 |
| Example 103 | I-7-j-1 | 23 | 28 | 80 |
| Example 104 | I-9-j-1 | 12 | 30 | 83 |
| Example 105 | I-10-j-1 | 15 | 25 | 82 |
| Example 106 | I-12-j-1 | 18 | 21 | 85 |
| Example 107 | I-16-j-1 | 19 | 21 | 85 |
| Example 108 | I-19-j-1 | 22 | 36 | 74 |
| Example 109 | I-23-j-1 | 28 | 30 | 79 |
| Example 110 | I-24-j-1 | 28 | 30 | 80 |
| Example 111 | I-26-j-2 | 13 | 25 | 82 |
| Example 112 | I-10-j-2 | 13 | 25 | 83 |
| Example 113 | I-10-j-3 | 18 | 21 | 85 |
| Example 114 | I-10-j-4 | 22 | 36 | 74 |
| Example 115 | I-10-j-9 | 28 | 30 | 79 |
| Example 116 | I-7-j-3 | 18 | 21 | 85 |
| Example 117 | I-7-j-9 | 22 | 36 | 74 |
| Example 118 | I-12-j-9 | 28 | 30 | 79 |
| Comparative Example 101 | H-1 | 50 | 100< | 70 |
| Comparative Example 102 | H-2 | 20 | 45 | 62 |
| Comparative Example 103 | H-3 | 25 | 42 | 68 |
| Comparative Example 104 | H-4 | 100< | 55 | 60 |

In Table 1, I-1-j-1, I-3-j-1, I-7-j-1, I-9-j-1, I-10-j-1, I-12-j-1, I-16-j-1, I-19-j-1, I-23-j-1, I-24-j-1, I-26-j-2, I-10-j-2, I-10-j-3, I-10-j-4, I-10-j-9, I-7-j-3, I-7-j-9, and I-12-j-9 shown in the column of "specific compound" indicate the specific compound of the present invention, and the structures thereof are as illustrated above. In addition, H-1, H-2, H-3, and H-4 are well-known compounds, and the structures thereof are as illustrated below. In the TfO⁻ represents a trifluoromethanesulfonate anion, and TsO⁻ represents a tosylate anion. The compounds H-1 to H-4 were synthesized using a well-known method.

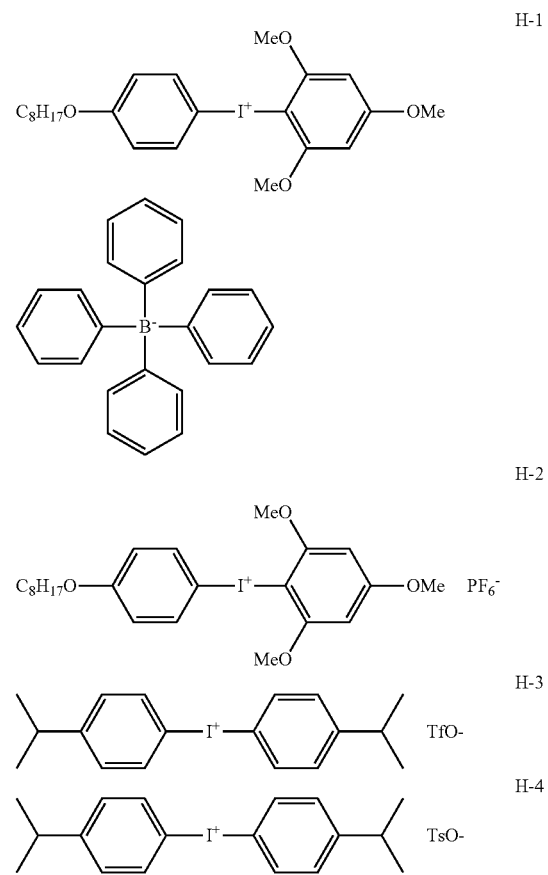

From the results shown in Table 1, it is found that the lithographic printing plate precursors having the image-recording layer containing the specific compound according to the present invention as the polymerization initiator are excellent in terms of all of the thermal and temporal stability (1), the on-machine developability, and the printing resistance.

The lithographic printing plate precursors of the comparative examples containing a well-known compound as the polymerization initiator are poor in terms of any one or more of the thermal and temporal stability (1) the on-machine developability and the printing resistance.

Examples 201 to 215 and Comparative Examples 201 to 206

[Production of Lithographic Printing Plate Precursor B]

A lithographic printing plate precursor B was produced in the same manner as in the production of the lithographic printing plate precursor A except fin the fact that, in the production of the lithographic plating plate precursor A, the support B was used instead of the support A, an image-recording layer coating fluid (2) described below was used instead of the image-recording layer coating fluid (1), and, furthermore, a protective layer described below was formed on the image-recording layer. The image-recording layer coating fluid (2) was prepared by mixing and stirring a photosensitive liquid (2) described below and a micro gel liquid immediately before being applied. Infrared absorbers, specific compounds, and polymerization initiators in the image-recording layer coating fluid (2) which were used to produce the respective lithographic printing plate precursors are summarized in Table 2.

<Photosensitive Liquid (2)> Amount Added
Binder polymer (1) [illustrated above]: 0.240 g
Infrared absorber (D-1) [illustrated above] or infrared absorber (D-2) [illustrated below] 0.024 g
Specific compound (polymerization initiator) shown in Table 2, well-known polymerization initiator, or parameter-regulating compound. Amount shown in Table 2
Specific compound shown in Table 2 (non-onium salt-type) Amount shown in Table 2
Polymerizable compound: Tris(acryyoyloxyethyl) isocyanurate, (NK ESTER A-9300, manufactured by Shin Nakamura Chemical Co., Ltd.) 0.192 g
Add color-developing agent 2'-Anilino-6'-(N-ethyl-N-isopentylamino)-3'-methylspiro[phthalide-3,9'-xanthene] (S-205, manufactured by Fukui Yamada Chemical Co., Ltd.) 0.080 g
Fluorine-based surfactant (1) [illustrated above]: 0.008 g
2-Butanone: 1.091 g
1-Methoxy-2-propanol: 8.609 g
<Micro Gel Liquid>
Micro gel (1) [illustrated above]: 2.640 g
Distilled water 2.425 g The structure of the infrared absorber (D-2) used in the photosensitive liquid (2) will be illustrated below. Meanwhile, the infrared absorber (D-2) is the compound 1.

Infrared absorber (D-2)

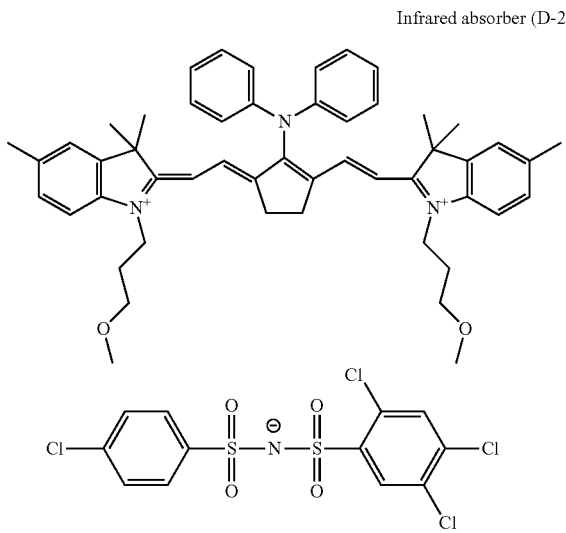

<Formation of Protective Layer>
A coating fluid for a protective layer having the following composition was applied onto the image-recording layer by means of bar coating and dried in an oven at 120° C. for 60 seconds, thereby forming a protective layer having a dried coating amount of 0.15 g/m².

<Coating fluid for protective layer>

| | |
|---|---|
| Inorganic lamellar compound dispersion liquid (1) [illustrated below] | 1.5 g |
| Six percent by mass aqueous solution of polyvinyl alcohol (CKS50 manufactured by The Nippon Synthetic Chemical Industry Co., Ltd., sulfonic acid-modified degree of saponification: 99% by mol or higher, degree of polymerization: 300) | 0.55 g |

-continued

<Coating fluid for protective layer>

| | |
|---|---|
| Six percent by mass aqueous solution of polyvinyl alcohol (PVA-405 manufactured by Kuraray Co., Ltd., degree of saponification: 81.5 mol %, degree of polymerization: 500) | 0.03 g |
| One percent by mass & aqueous solution of a surfactant (polyoxyethylene lauryl ether, EMALEX 710, manufactured by Nihon Emulsion Co., Ltd.) | 0.86 g |
| Ion exchange water | 6.0 g |

A method for preparing the inorganic lamellar compound dispersion liquid (1) will be described below.
<Preparation of Inorganic Lamellar Compound Dispersion Liquid (1)>
Synthetic mica (SOMASIF MEXICO manufactured by Co-op Chemical Co., Ltd.) (6.4 g) was added to ion exchange water (193.6 g) and dispersed using a homogenizer until the average particle diameter (laser scattering method) reached 3 µm. The aspect ratio of the obtained dispersed particle was 100 or higher.

[Evaluation of Lithographic Printing Plate Precursors]
For the respective lithographic printing plate precursors B, the on-machine developability, the thermal and temporal stability (1), and the printing resistance were evaluated in the same manner as those of the lithographic printing plate precursor A. Furthermore, the odor developability and the thermal and temporal stability (2) (ring-shaped color development prevention property) were evaluated using the following evaluation method. The results are shown in Table 2.

<Color Developability>
The lithographic printing plate precursor was exposed using a TRENDSETTER 3244VX manufactured by Creo Co., Ltd. which was equipped with a water coding-type 40 W infrared semiconductor laser under conditions of an output of 11.7 W, an external surface dram rotation speed of 250 rpm, and a resolution of 2,400 dpi (dot per inch, 1 inch=25.4 mm). The exposure was carried out in an environment of 25° C. and 50% RH.

The color development of the lithographic printing plate precursor was measured immediately after the exposure. The color development was measured using a spectrophotometer CM2600d and operation software CM-S100W manufactured by Konica Minolta. Inc. by means of a specular component excluded (SCH) method. The color developability were evaluated using foe difference ΔL between foe. If value of an exposed portion and foe L* value of a non-exposed portion using L* values (tightness) in foe L*a*b* color system. The numerical values of ΔL are shown in Table 2. A larger value of ΔL indicates superior color developability and also indicates a superior plate inspection property of the lithographic printing plate by color development <Thermal and Temporal Stability (2) (Ring-Shaped Color Development Prevention Property)>
The lithographic printing plate precursor was adjusted in humidity in an environment of 25° C. and 60% for one hour and then packed. Next, the packed matter was thermally aged at 60° C. for four days. After the end of the thermal aging, the number of dots that developed color in a ring shape in a 50×300 mm area range was visually counted. The ring-shaped color development prevention property was evaluated by rating a lithographic printing plate precursor having no color-developed points as A, a lithographic printing plate precursor having 1 to 10 color-developed points as B, and a lithographic printing plate precursor having more than 10 color-developed points as C. The lithographic printing plate precursor are demanded not to develop color in a ring shape (B and C are indexes for expressing the difference in degree of ring-shaped color development).

TABLE 2

|  | Infrared absorber | Specific compound (polymerization initiator) | | Specific compound (non-onium salt) | | Polymerization initiator | |
|---|---|---|---|---|---|---|---|
|  |  | Kind | Amount added (g) | Kind | Amount added (g) | Kind | Amount added (g) |
| Example 201 | D-1 | I-1-j-1 | 0.245 | — | — | — | — |
| Example 202 | D-1 | I-7-j-1 | 0.245 | — | — | — | — |
| Example 203 | D-1 | I-9-j-1 | 0.245 | — | — | — | — |
| Example 204 | D-1 | I-10-j-1 | 0.245 | — | — | — | — |
| Example 205 | D-1 | I-12-j-1 | 0.245 | — | — | — | — |
| Example 206 | D-1 | I-16-j-1 | 0.245 | — | — | — | — |
| Example 207 | D-1 | — | — | I-1-h-1 | 0.06 | H-4 | 0.18 |
| Example 208 | D-1 | — | — | I-7-h-1 | 0.06 | H-4 | 0.18 |
| Example 209 | D-1 | — | — | I-10-h-1 | 0.06 | H-4 | 0.18 |
| Example 210 | D-1 | — | — | I-12-h-1 | 0.06 | H-4 | 0.18 |
| Example 211 | D-1 | I-9-j-3 | 0.245 | — | — | — | — |
| Example 212 | D-1 | I-13-j-3 | 0.245 | — | — | — | — |
| Example 213 | D-1 | I-1-j-9 | 0.245 | — | — | — | — |
| Example 214 | D-2 | I-7-j-1 | 0.245 | — | — | — | — |
| Comparative Example 201 | D-1 | — | — | — | — | H-1 | 0.245 |
| Comparative Example 202 | D-1 | — | — | — | — | H-2 | 0.245 |
| Comparative Example 203 | D-1 | — | — | — | — | H-3 | 0.245 |
| Comparative Example 204 | D-1 | — | — | — | — | H-4 | 0.245 |
| Example 215 | D-2 | B-2-j-1 | 0.245 | — | — | — | — |
| Comparative Example 205 | D-1 | — | — | — | — | H-5 | 0.245 |
| Comparative Example 206 | D-1 | — | — | — | — | H-6 | 0.245 |

|  | Color developability | Thermal and temporal stability (2) | On-machine developability (number of pieces) | Thermal and temporal stability (1) (number of pieces) | Printing resistance |
|---|---|---|---|---|---|
| Example 201 | 5.3 | A | 20 | 30 | 75 |
| Example 202 | 5.8 | A | 30 | 20 | 70 |
| Example 203 | 5.6 | A | 20 | 25 | 75 |
| Example 204 | 5.4 | A | 8 | 25 | 78 |
| Example 205 | 5.5 | A | 10 | 20 | 80 |
| Example 206 | 5.2 | A | 15 | 20 | 82 |
| Example 207 | 5.3 | A | 20 | 30 | 75 |
| Example 208 | 5.6 | A | 22 | 27 | 75 |
| Example 209 | 5.4 | A | 15 | 20 | 80 |
| Example 210 | 5.4 | A | 15 | 20 | 80 |
| Example 211 | 5.5 | A | 20 | 18 | 78 |
| Example 212 | 5.6 | A | 25 | 25 | 75 |
| Example 213 | 5.9 | A | 18 | 22 | 78 |
| Example 214 | 5.4 | A | 15 | 18 | 85 |
| Comparative Example 201 | 5.0 | A | 50 | 100< | 75 |
| Comparative Example 202 | 3.5 | C | 20 | 35 | 65 |
| Comparative Example 203 | 4.0 | B | 25 | 32 | 65 |
| Comparative Example 204 | 3.0 | A | 100< | 30 | 65 |
| Example 215 | 5.2 | A | 10 | 20 | 83 |
| Comparative Example 205 | 4.2 | C | 35 | 40 | 70 |
| Comparative Example 206 | 3.5 | A | 100< | 45 | 65 |

In Table 2, I-1-j-1, I-7-j-1, I-9-j-1, I-10-j-1, T-12-j-1, I-16-j-1, I-9-J-3, I-13-j-3, I-1-j-9, I-7-j-1, I-1-b-1, I-7-h-1, I-10-h-1, and I-12-h-1 shown in the column of "specific compound" indicate the specific compound of the present invention, and the structures thereof are as illustrated above. In addition, H-1, H-2, H-3, and H-4 are well-known compounds, and the structures thereof are as illustrated above.

In addition, H-5 and H-6 are well-known compounds, and the structures thereof are as illustrated below,

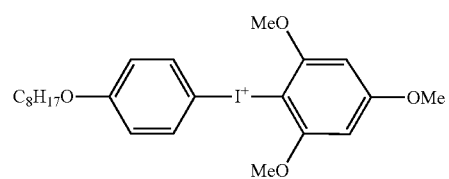

H-5

CFSO₂N⁻SO₂CF₃

H-6

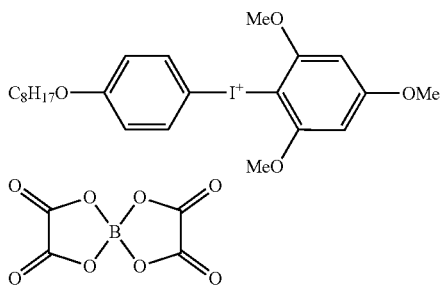

For the anion portions of the compounds H-1 and H-3 to H-6, δd, δp, δH, and the percentage (%) of δH to δp (δH/δp×100) in Hansen solubility parameter are shown in the following table.

|  | Δd | δp | δH | δH/δp |
|---|---|---|---|---|
| Anion portion of H-1 | 19.2 | 1.7 | 3.1 | 182% |
| Anion portion of H-3 | 16.9 | 18.1 | 21 | 116% |
| Anion portion of H-4 | 19.8 | 14.6 | 17.7 | 121% |
| Anion portion of H-5 | 15.8 | 24.2 | 10.6 | 44% |
| Anion portion of H-6 | 18 | 49 | 13.2 | 27% |

From the results shown in Table 2, it is found that the lithographic printing plate precursors having the image-recording layer containing the specific compound or the parameter-regulating compound according to the present invention are excellent in terms of all of the thermal and temporal stability (1), the on-machine developability, the printing resistance, the color developability, and the thermal and temporal stability (2).

The lithographic printing plate precursors of the comparative examples containing a well-known polymerization initiator are poor in terms of any one or more of the thermal and temporal stability (1), the on-machine developability, the color developability, and the thermal and temporal stability (2).

Examples 301 to 314 and Comparative Examples 301 to 306

[Production of Lithographic Printing Plate Precursor C]

A lithographic printing plate precursor C was produced by using the support C instead of the support A, applying an image-recording layer coating fluid (3) having the following composition by means of bar coating instead of the image-recording layer coating fluid (1) and drying the coating fluid in an oven at 70° C. for 60 seconds, thereby forming an image-recording layer having a dried coating amount of 0.6 g/m² in the production of the lithographic printing plate precursor A. Infrared absorbers, specific compounds, and polymerization initiators in the image-recording layer coating fluid (3) which were used to produce the respective lithographic printing plate precursors are summarized in Table 3.

| <Image-recording layer coating fluid (3)> | |
|---|---|
| Infrared absorber (D-3) or (D-4) | 0.018 g |
| Specific compound shown in Table 3 | |

| <Image-recording layer coating fluid (3)> | |
|---|---|
| (polymerization initiator), well-known polymerization initiator, or parameter-regulating compound Amount shown in Table 3 | |
| Specific compound shown in Table 3 (non-onium salt-type) Amount shown in Table 3 | |
| Borate compound: | 0.010 g |
| TPB [illustrated below] | |
| Polymer particle water dispersion liquid (1) (22% by mass) [illustrated below]: | 10.0 g |
| Polymerizable compound: | 1.50 g |
| SR-399 (manufactured by Sartomer Japan Inc.) | |
| Acid color-developing agent: 2'-Anilino-6'-(N-ethyl-N-isopentylamino)-3'-methylspipro[phthalide-3,9'-xanthene] (S-205, manufactured by Fukui Yamada Chemical Co., Ltd.) | 0.080 g |
| Mercapto-3-triazole: | 0.2 g |
| Byk 336 (manufactured by BYK Additives & Instruments): | 0.4 g |
| Klucel M (manufactured by Hercules Incorporated): | 4.8 g |
| ELVACITE 4026 (manufactured by Ineos Acrylics): | 2.5 g |
| n-Propanol: | 55.0 g |
| 2-Butanone: | 17.0 g |

The infrared absorbers (D-3) and (D-4), TPB, and the confounds expressed using trade names which were used for the image-recording layer coating fluid (3) are as described below.

Infrared absorber (D-3)

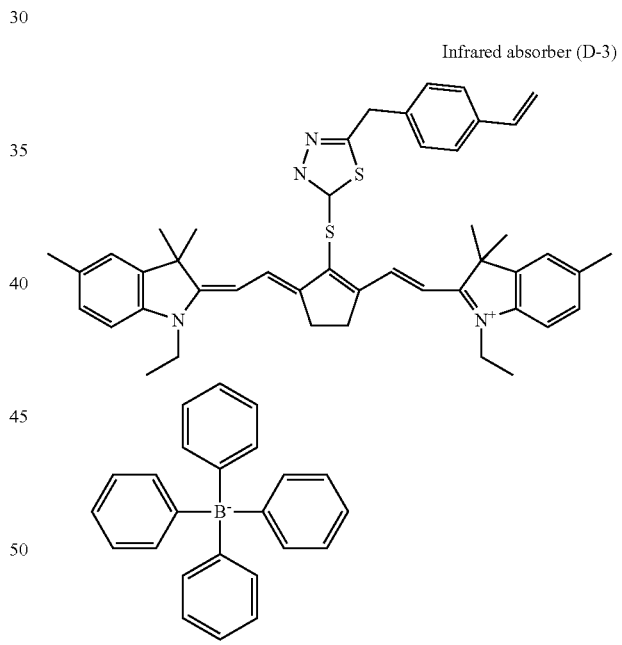

Infrared absorber (D-4)

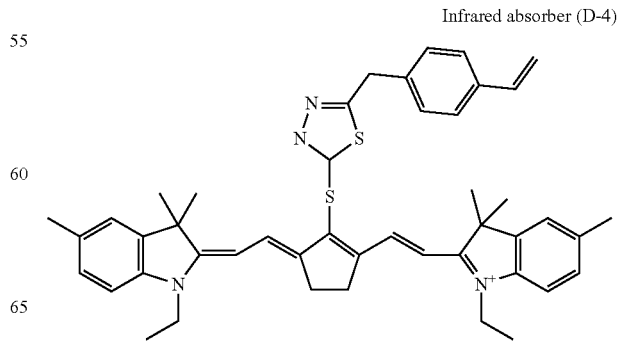

-continued

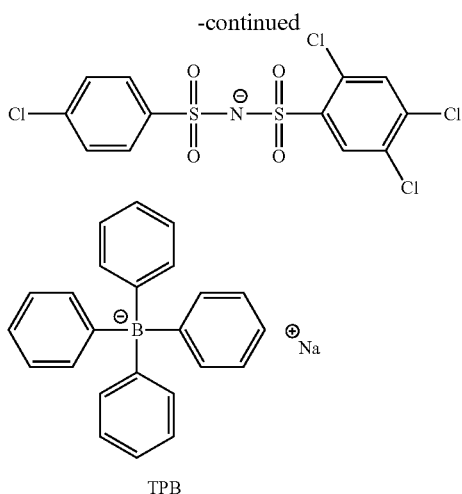

TPB

SR-399: Dipentaerythritol pentaacrylate
Byk 336: Modified dimethyl polysiloxane copolymer (a solution of 25% by mass of xylene and methoxypropyl acetate)
Klucel M: Hydroxypropyl cellulose (2% by mass aqueous solution)
ELVACITE 4026: Highly branched polymethyl methacrylate (a solution of 10% by mass of 2-butanone)

A method for preparing the polymer particle water dispersion liquid (1) used for the image-recording layer coating fluid (3) will be described below.

<Preparation of Polymer Particle Water Dispersion Liquid (1)>

A stirrer, a thermometer, a dropping funnel, a nitrogen introduction pipe, and a reflux cooler were provided to a four-neck flask, nitrogen gas was introduced thereinto, polyethylene glycol methyl ether methacrylate (PEGMA, the average repeating unit number of ethylene glycol: 50) (10 g), distilled water (200 g), and n-propanol (200 g) were added thereto while carrying out deoxidation by introducing nitrogen gas, and the components were heated until the inner temperature reached 70° C. Next, a mixture obtained by mixing styrene (St) (10 g), acrylonitrile (AN) (80 g), and 2,2'-azobisuobutyronitrile (0.8 g) in advance was added dropwise thereto for one hour A reaction continued for five hours after the end of the dropwise addition, then, 2,2'-azobisisobutyronitiile (0.4 g) was added thereto, and the inner temperature was increased op to 80° C., Subsequently, 2,2-azobisisobutyronitrile (0.5 g) was added thereto for six boors. Al a stage of continuing the reaction for a total of 20 hours, 98% or more of polymerization had progressed, and a polymer particle water dispersion liquid (1) including PEGMA/St/AN in a mass ratio of 10/10/80 was prepared. The particle size distribution of the polymer particles had the maximum value al a particle diameter of 150 nm.

The particle size distribution was obtained by capturing an electron micrograph of the polymer particles, measuring the particle diameters of a total of 5,000 particles on the photograph, dividing the range of the obtained particle diameter measurement values from zero to the value into 50 sections using a logarithmic scale, and plotting the appearance frequency of the respective particle diameters. Meanwhile, for a non-spherical particle, the particle diameter value of a spherical particle having the same particle area as the particle area on the photograph was considered as the particle diameter:

[Evaluation of Lithographic Printing Plate Precursors]

For the respective lithographic printing plate precursors C, the thermal and temporal stability (1), the on-machine developability, the printing resistance, the color developability, and the thermal and temporal stability (2) were evaluated in the same manner as diose of the lithographic printing plate precursor B. The evaluation results are shown in Table 3.

TABLE 3

|  | Infrared absorber | Specific compound (polymerization initiator) | | Specific compound (non-onium salt) | | Polymerization initiator | |
|---|---|---|---|---|---|---|---|
|  |  | Kind | Amount added (g) | Kind | Amount added (g) | Kind | Amount added (g) |
| Example 301 | D-3 | I-1-j-1 | 0.16 | — | — | — | — |
| Example 302 | D-3 | I-7-j-1 | 0.16 | — | — | — | — |
| Example 303 | D-3 | I-9-j-1 | 0.16 | — | — | — | — |
| Example 304 | D-3 | I-10-j-1 | 0.16 | — | — | — | — |
| Example 305 | D-3 | I-12-j-1 | 0.16 | — | — | — | — |
| Example 306 | D-3 | I-16-j-1 | 0.16 | — | — | — | — |
| Example 307 | D-3 | — | — | I-1-h-1 | 0.04 | H-4 | 0.12 |
| Example 308 | D-3 | — | — | I-7-h-1 | 0.04 | H-4 | 0.12 |
| Example 309 | D-3 | — | — | I-10-h-1 | 0.04 | H-4 | 0.12 |
| Example 310 | D-3 | I-9-j-3 | 0.16 | — | — | — | — |
| Example 311 | D-3 | I-13-j-3 | 0.16 | — | — | — | — |
| Example 312 | D-3 | I-1-j-9 | 0.16 | — | — | — | — |
| Example 313 | D-4 | I-9-j-1 | 0.16 | None | — | — | — |
| Comparative Example 301 | D-3 | — | — | — | — | H-1 | 0.12 |
| Comparative Example 302 | D-3 | — | — | — | — | H-2 | 0.12 |
| Comparative Example 303 | D-3 | — | — | — | — | H-3 | 0.12 |
| Comparative Example 304 | D-3 | — | — | — | — | H-4 | 0.12 |
| Example 314 | D-3 | B-2-j-1 | 0.16 | None | — | — | — |
| Comparative Example 305 | D-3 | — | — | — | — | H-5 | 0.12 |
| Comparative Examole 306 | D-3 | — | — | — | — | H-6 | 0.12 |

TABLE 3-continued

|  | Color developability | Thermal and temporal stability (2) | On-machine developability (number of pieces) | Thermal and temporal stability (1) (number of pieces) | Printing resistance |
|---|---|---|---|---|---|
| Example 301 | 4.3 | A | 25 | 35 | 75 |
| Example 302 | 4.2 | A | 32 | 25 | 73 |
| Example 303 | 4.5 | A | 22 | 27 | 70 |
| Example 304 | 4.4 | A | 12 | 20 | 75 |
| Example 305 | 4.0 | A | 15 | 25 | 78 |
| Example 306 | 4.2 | A | 15 | 25 | 79 |
| Example 307 | 4.1 | A | 30 | 30 | 76 |
| Example 308 | 4.2 | A | 15 | 22 | 75 |
| Example 309 | 4.2 | A | 20 | 27 | 80 |
| Example 310 | 4.6 | A | 25 | 23 | 78 |
| Example 311 | 4.4 | A | 28 | 29 | 75 |
| Example 312 | 4.8 | A | 25 | 29 | 73 |
| Example 313 | 4.3 | A | 15 | 20 | 80 |
| Comparative Example 301 | 4.6 | A | 55 | 100< | 78 |
| Comparative Example 302 | 3.2 | C | 25 | 38 | 68 |
| Comparative Example 303 | 3.5 | B | 30 | 37 | 60 |
| Comparative Example 304 | 2.5 | A | 100< | 35 | 63 |
| Example 314 | 4.8 | A | 12 | 25 | 85 |
| Comparative Example 305 | 3.6 | C | 45 | 45 | 68 |
| Comparative Examole 306 | 2.7 | A | 100< | 60 | 63 |

In Table 3, I-1-j-1, I-7-j-1, I-9-j-1, I-10-j-1, I-12-j-1, I-16-j-1, I-9-j-3, I-13-j-3, I-1-j-9, I-9-j-1, I-1-b-1, I-7-h-1, and I-10-H-1 shown in the column of "specific compound" indicate the specific compound of the present invention, and the structures thereof are as illustrated above. In addition, H-1, H-2, H-3, and H-4 were well-known compounds, and the structures thereof are as illustrated above.

From the remits shown in Table 3, it is found that the lithographic printing plate precursors having the image-recording layer containing the specific compound or the parameter-regulating compound according to the present invention are excellent in terms of all of the thermal and temporal stability (1), the on-machine developability; the printing resistance, the color developability, and the thermal and temporal stability (2).

The lithographic printing plate precursors of the comparative examples containing a well-known polymerization initiator are poor in terms of any one or more of the thermal and temporal stability (1), the on-machine developability, the color developability, and the thermal and temporal stability (2).

Examples 401 to 415 and Comparative Examples 401 to 406

[Production of Lithographic Printing Plate Precursor D]

A lithographic printing plate precursor D was produced by using the support D instead of the support A, applying an image-recording layer coating aqueous solution (4) having a composition that became as described below after coating by means of bar coating rnstead of the image-recording layer coating fluid (1), and drying the coating aqueous solution in an oven at 50° C. for 60 seconds, thereby forming an image-recording layer having a dried coating amount of 0.93 g/m$^2$ in the production of the lithographic printing plate precursor A. Infrared absorbers, specify compounds, and acid-generating agents in the image-recording layer coating fluid (4) which were used to produce the respective lithographic printing plate precursors are summarized in Table 4.

| <Image-Recording Layer Coating Fluid (4)> | |
|---|---|
| Infrared absorber (D-3), (D-5), or (D-6) | 0.045 g/m$^2$ |
| Specific compound Shown in Table 4 (acid-generating agent), well-known acid-generating agent, or parameter-regulating compound shown in Table 4 | |
| Specific compound shown in Table 4 (non-onium salt-type) shown in Table 4 | |
| Borate compound: TPB [illustrated above] | 0.010 g/m$^2$ |
| Acid color-developing agent: 2'-Anilino-6'-(N-ethyl-N-isopentylamino)-3'-methylspiro[phthalide-3,9'-xanthene] (S-205, mantifactured by Fukui Yamada Chemical Co., Ltd.) | 0.080 g/m$^2$ |
| Polymer particle water dispersion liquid (2): | 0.693 g/m$^2$ |
| Glascol E15: (manufactured by Allied Colloids Manufacturing GMBH) | 0.09 g/m$^2$ |
| ERKOL WX48/20 (manufactured by ERKOL): | 0.09 g/m$^2$ |
| Zonyl FSO100 (manufactured by DuPont): | 0.0075 g/m$^2$ |

The compounds which were used for the image-recording layer coating fluid (4) and are expressed using trade names, the polymer particle water dispersion liquid (2), and the infrared absorbers (D-5) and (D-6) are as described below.

Glascol E15: Polyacrylic acid

ERKOL WX48/20: Polyvinyl alcohol/polyvinyl acetate copolymer

Zonyl FSO100: Surfactant

Polymer particle water dispersion liquid (2): A styrene/acrylonitrile copolymer stabilized with an anionic wetting agent (the molar ratio: 50/50, the average particle diameter 61 nm, and the solid content: approximately 20%)

Infrared absorber (D-5)

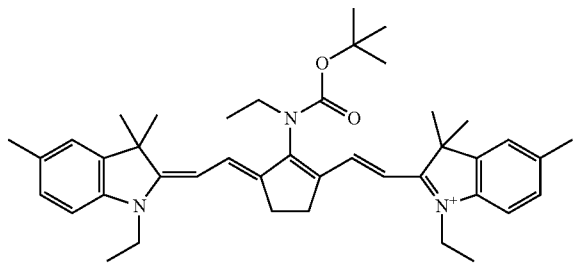

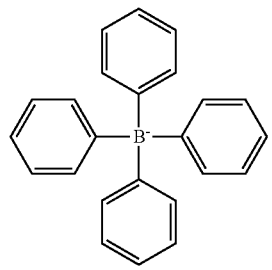

Infrared absorber (D-6)

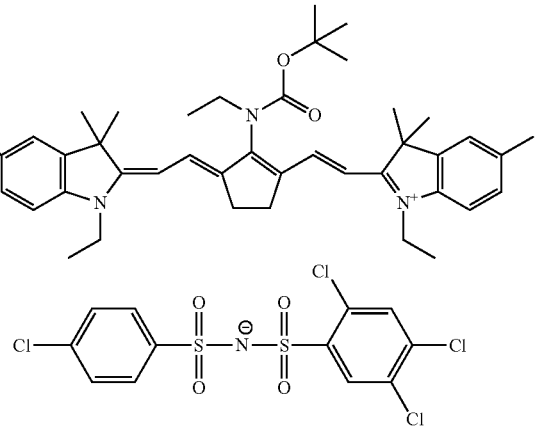

[Evaluation of Lithographic Printing Plate Precursors]

For the respective lithographic printing plate precursors D, the thermal and temporal stability (1), the on-machine developability, the printing resistance, the color developability, and the thermal and temporal stability (2) were evaluated in the same manner as diose of using the lithographic printing plate precursor B. The evaluation results are shown in Table 4.

TABLE 4

| | Infrared absorber | Specific compound (acid-generating agent) | | Specific compound (non-onium salt) | | Acid-generating agent | |
|---|---|---|---|---|---|---|---|
| | | Kind | Amount added (g/m$^2$) | Kind | Amount added (g/m$^3$) | Kind | Amount added (g/m$^2$) |
| Example 401 | D-5 | I-1-i-1 | 0.3 | — | — | — | — |
| Example 402 | D-5 | I-7-j-1 | 0.3 | — | — | — | — |
| Example 403 | D-5 | I-9-j-1 | 0.3 | — | — | — | — |
| Example 404 | D-5 | I-10-j-1 | 0.3 | — | — | — | — |
| Example 405 | D-5 | I-12-j-1 | 0.3 | — | — | — | — |
| Example 406 | D-5 | I-16-j-1 | 0.3 | — | — | — | — |
| Example 407 | D-5 | — | — | I-1-h-1 | 0.06 | H-4 | 0.24 |
| Example 408 | D-5 | — | — | I-7-h-1 | 0.06 | H-4 | 0.24 |
| Example 409 | D-5 | — | — | I-10-h-1 | 0.06 | H-4 | 0.24 |
| Example 410 | D-5 | — | — | I-12-h-1 | 0.06 | H-4 | 0.24 |
| Example 411 | D-5 | I-9-i-3 | 0.3 | — | — | — | — |
| Example 412 | D-5 | I-13-j-3 | 0.3 | — | — | — | — |
| Example 413 | D-5 | I-1-j-9 | 0.3 | — | — | — | — |
| Example 414 | D-6 | I-9-j-1 | 0.3 | — | — | — | — |
| Comparative Example 401 | D-5 | — | — | — | — | H-1 | 0.3 |
| Comparative Example 402 | D-5 | — | — | — | — | H-2 | 0.3 |
| Comparative Example 403 | D-5 | — | — | — | — | H-3 | 0.3 |
| Comparative Example 404 | D-5 | — | — | — | — | H-4 | 0.3 |
| Example 415 | D-3 | B-2-j-1 | 0.3 | — | — | — | — |
| Comparative Example 405 | D-5 | — | — | — | — | H-5 | 0.3 |
| Comparative Example 406 | D-5 | — | — | — | — | H-6 | 0.3 |

TABLE 4-continued

|  | Color developability | Thermal and temporal stability (2) | On-machine developability (number of pieces) | Thermal and temporal stability (1) (number of pieces) | Printing resistance |
|---|---|---|---|---|---|
| Example 401 | 5.8 | A | 22 | 32 | 75 |
| Example 402 | 6.0 | A | 28 | 25 | 73 |
| Example 403 | 6.1 | A | 25 | 30 | 70 |
| Example 404 | 6.3 | A | 24 | 36 | 75 |
| Example 405 | 6.4 | A | 20 | 29 | 75 |
| Example 406 | 5.9 | A | 24 | 26 | 73 |
| Example 407 | 5.7 | A | 25 | 32 | 75 |
| Example 408 | 5.9 | A | 28 | 25 | 73 |
| Example 409 | 5.8 | A | 24 | 30 | 75 |
| Example 410 | 5.8 | A | 24 | 30 | 75 |
| Example 411 | 5.9 | A | 24 | 20 | 77 |
| Example 412 | 6.3 | A | 29 | 30 | 70 |
| Example 413 | 6.3 | A | 22 | 28 | 80 |
| Example 414 | 6.1 | A | 24 | 36 | 75 |
| Comparative Example 401 | 5.5 | A | 48 | 100< | 70 |
| Comparative Example 402 | 4.5 | C | 21 | 50 | 70 |
| Comparative Example 403 | 3.5 | B | 25 | 40 | 60 |
| Comparative Example 404 | 2.5 | A | 100< | 35 | 63 |
| Example 415 | 5.9 | A | 23 | 30 | 88 |
| Comparative Example 405 | 3.2 | C | 60 | 55 | 68 |
| Comparative Example 406 | 2.2 | A | 80 | 50 | 65 |

In Table 4, I-1-j-1, I-7-j-1, I-9-j-1, I-10-j-1, I-12-j-1, I-16-j-1, I-9-J-3, I-13-J-3, I-1-j-9, I-9-j-1, I-1-h-1, I-7-h-1, I-10-h-1 and I-12-h-1 shown in the column of "specific compound" indicate the specific compound of the present invention, and the structures thereof are as illustrated above. In addition, H-1, H-2,H-3, and H-4 were well-known confounds, and the structures thereof are as illustrated above. In Table 4, numerical values as the content indicate the dried coating amounts, and the unit is g/m$^2$.

From the results shown in Table 4, it is found that the lithographic printing plate precursors having the image-recording layer containing the specific compound or the parameter-regulating compound according to the present invention are excellent in terms of all of the thermal and temporal stability (1), the on-machine developability, the printing resistance, the color developability, and the thermal and temporal stability (2).

The lithographic printing plate precursors of the comparative examples containing a well-known acid-generating agent are poor in terms of any one or more of the thermal and temporal stability (1), the on-machine developability, the color developability, and the thermal and temporal stability (2).

Examples 501 to 505 and Comparative Examples 501 and 502

[Production of Lithographic Printing Plate Precursor E]
<Production of Support E>

On a 0 J mm-thick aluminum plate (material: JIS A 1050), individual processes of (a) to (i) below were continuously carried out, thereby carrying out a surface treatment. Meanwhile, after each process and water washing, liquid was drained using a nip roller.

(a) Alkali Etching Process

On the aluminum plate, an etching process was carried out by means of spraying using an aqueous solution having a sodium hydroxide concentration of 2.6% by mass, an aluminum ion concentration of 6.5% by mass, and a temperature of 70° C., thereby dissolving 6 g/m$^3$ of the aluminum plate. After that, the plate was washed with water by means of spraying.

(b) Desmut Process

On the aluminum plate, a desmut process was carried out by means of spraying using an aqueous solution having a temperature of 30° C. and a nitric acid concentration of 1% by mass (including 0.5% by mass of aluminum ions) and then the plate was washed with water by means of spraying. As the nitric acid aqueous solution used in the desmut process, a waste liquid of a step of carrying out an electro-chemical roughening process in a nitric acid aqueous solution using an alternating current was used.

(c) Electrochemical Roughening Process

An electrochemical roughening process was continuously carried oat using an alternating current voltage of 60 Hz. An electrolytic solution was a 10.5 g/L aqueous solution of nitric acid (including 5 g/L of aluminum ions and 0.007% by mass of ammonium ions), and the liquid temperature was 50° C. The electrochemical roughening process was carried out thereon using an alternating current power supply waveform in which the time TP taken for the current value to reach the peak from zero was 0.8 msec and the duty ratio was 1:1, and the electrochemical roughening process was carried out using a trapezoidal rectangular wave alternating current and a carbon electrode as a counter electrode. As the auxiliary anode, ferrite was used. The current density was 30 A/dm$^2$ in terms of the peak value of the current, and the quantity of electricity was 220 C/dm$^2$ in terms of the sum of the quantities of electricity in a case in which the aluminum plate was the positive electrode. Five percent of the current coming from the power supply was divided into the auxiliary anode. After that, the plate was washed with water by means of spraying.

(d) Alkali Etching Process

On the aluminum plate, an etching process was carried out at 32° C. by spraying an aqueous solution having a sodium hydroxide concentration of 26% by mass, an aluminum ion concentration of 6.5% by mass, 0.25 g/m² of the aluminum plate was dissolved, a smut component including, as a main body, aluminum hydroxide generated at the time of the electrochemical roughening process was removed, and, additionally, the edge portion of the generated pit was dissolved to smoothen the edge portion. After that, the plate was washed with water by means of spraying.

(e) Desmut Process

A desmut process was carried out by spraying an aqueous solution having a sulfuric acid concentration of 15% by mass of a temperature of 30° C. (including 4.5% by mass of aluminum ions) and then the plate was washed with water by means of spraying. As the nitric acid aqueous solution used in the desmut process, the waste liquid of the step of carrying out the electrochemical roughening process in the nitric acid aqueous solution using an alternating current was used.

(f) Electrochemical Roughening Process

An electrochemical roughening process was continuously carried out using an alternating current voltage of 60 Hz. An electrolytic solution was a 2.5 g/L aqueous solution of hydrochloric acid (including 5 g/L of aluminum ions), and the temperature was 35° C. The electrochemical roughening process was carried out thereon using an alternating current power supply waveform in which the time TP taken for the current value to reach the peak from zero was 0.8 msec and the duty ratio was 1:1, and the electrochemical roughening process was earned out using a trapezoidal rectangular wave alternating current and a carbon electrode as a counter electrode. As the auxiliary anode, ferrite was used. The current density was 25 A/dm² in terms of the peak value of the current, and the quantity of electricity was 50 C/dm² in terms of the sum of the quantities of electricity in a case in which the aluminum plate was the positive electrode. After that, the plate was washed with water by means of spraying.

(g) Alkali Etching Process

On the aluminum plate, an etching process was carried out at 32° C. by spraying an aqueous solution having a sodium hydroxide concentration of 26% by mass, an aluminum ion concentration of 6.5% by mass, 0.1 g/m² of the aluminum plate was dissolved, a smut component including, as a main body, aluminum hydroxide generated at the time of the electrochemical roughening process was removed, and, additionally, the edge portion of the generated pit was dissolved to smoothen the edge portion. After that, the plate was washed with water by means of spraying.

(h) Anodization Process 2.5 g/m² of a direct current anodized film was formed on the aluminum plate at a current density of 15 A/dm² using a 15% by mass aqueous solution of sulfinic acid (including 0.5% by mass of aluminum ions) as an electrolytic solution, washed with water, and dried. The average pore diameter of the surface layer of the film (surface-average pore diameter) was 10 nm.

The pore diameter of the surface layer of the anodized film was measured using a method in which the surface was observed an ultrahigh resolution SEM (S-900 manufactured by Hitachi, Ltd) at a relatively low acceleration voltage of 12 V at a magnification of 150,000 times without carrying out a vapor deposition process or the like for imparting conductive properties, 50 pores were randomly extracted md the average value was obtained. The standard deviation error was ±10% or less.

(i) Hydrophilization Process

In order to ensure the hydrophilicity of a non-image area, a silicate process was carried out on the aluminum plate using a 2.5% by mass aqueous solution of No. 3 sodium silicate at 60° C. for ten seconds, and the aluminum plate was washed with water, thereby producing a support E. The attached amount of Si was 9.5 mg/m². The center line average roughness (Ra) of the support E was measured using a needle having a diameter of 2 μm and was found to be 0.27 μm.

<Formation of Undercoat Layer>

A coating fluid for an undercoat layer (2) having the following composition was applied onto the support E so that the dried coating amount reached 20 mg/m², thereby forming an undercoat layer.

| (Coating fluid for undercoat Layer (2)) | |
| --- | --- |
| Polymer (P-2) [illustrated below] | 0.18 g |
| Tetrasodium ethylenediaminetetraacetate | 0.10 g |
| Polyoxyethylene lauryl ether | 0.03 g |
| Water | 61.39 g |

Polymer (P-2)  Mw 100,000

Meanwhile, numerical values on be lower rigid side of parentheses of individual constitutional units in the polymer (P-2) represent mass ratios, and a numerical value on the lower right side of the ethyleneoxy unit represents the number of times of repetition.

<Formation of Image-Recording Layer>

A coating fluid for an image-recording layer (5) having the following composition was applied onto the undercoat layer by means of bar coating and then dried in an oven at 100° C. for 60 seconds, thereby forming an image-recording layer having a dried coating amount of 1.0 g/m².

The coating fluid for the image-recording layer (5) was prepared by mixing and stirring the following photosensitive liquid (5) and a micro gel liquid immediately before the application.

<Photosensitive Liquid (5)>

Binder polymer (2) [structure illustrated below]: 0.240 g

Infrared absorber (D-2) [illustrated above] 0.024 g

Specific compound shown in Table 5 (polymerization initiator) or well-known polymerization initiator 0,245 g Polymerizable compound: Tris(acryloyloxyethyl)isocyanurate, (NK ester A-9300, manufactured by Shin-Nakamura Chemical Co., Ltd.) 0.192 g Coloring agent [illustrated below]: 0.030 g Fluorine-based surfactant (1) [illustrated above]: 0.008 g 2-Butanone: 1.091 g 1-Methoxy-2-propanol: 8.609 g <Micro gel Liquid>

Micro gel (1) [illustrated above]: 2.640 g

Distilled water 2.425 g

The structures of the binder polymer (2) and the coloring agent which were used for the photosensitive liquid (5) will be illustrated below.

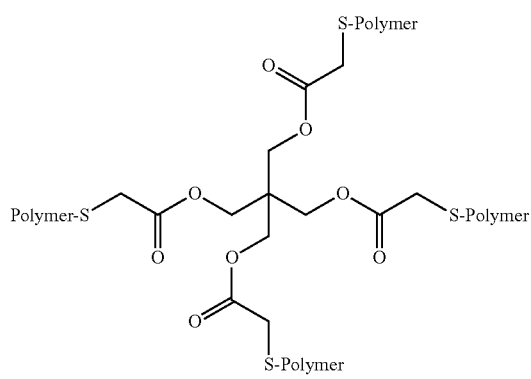

Polymer portion described above

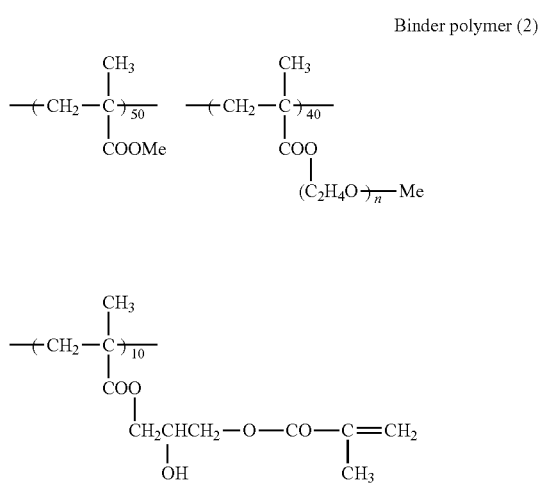

Binder polymer (2)

Meanwhile, Me represents a methyl group, and numbers on the lower right side of parentheses of individual constitutional units in the binder polymer (2) represent molar ratios.

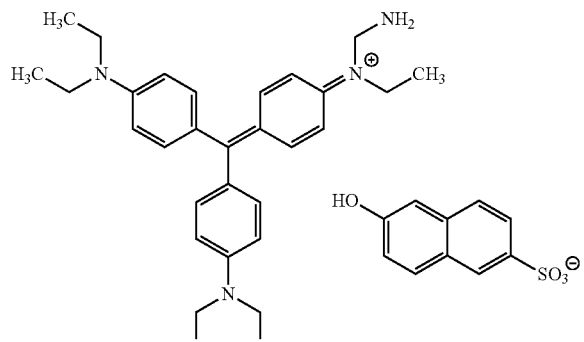

Coloring agent

<Formation of protective Layer>

The coating Stud for a protective layer was applied onto the image-recording layer by means of bar coating and dried in an oven at 120° C. for 60 seconds, thereby forming a protective layer having a dried coating amount of 0.15 g/m$^2$.

[Evaluation of Lithographic Printing Plate Precursors]

For the respective lithographic printing plate precursors E, the printing resistance and the thermal and temporal stability (3) were evaluated using the following evaluation methods. The evaluation results are shown in Table 5.

<Printing Resistance>

[Image Exposure]

The lithographic printing plate precursors were exposed using a LUXEL PLATESETTER T-6000DI manufactured by Fujifilm Corporation which was equipped with an inflated semiconductor laser under conditions of an external surface drum rotation speed of 1,000 rpm, a laser output of 70%, and a resolution of 2,400 dpi. Exposed images were provided with solid images and 50% halftone dot charts.

[Development Process]

A development process was carried out on the exposed lithographic printing plates using Clean Out Unit+ C85 manufactured by Glunz & Jensen at a transportation rate of 60 cm/min and 20° C., thereby producing lithographic printing plates. In the development process, a developer having the following composition was used. This developer is a developer capable of carrying out the removal of the protective layer, development, and gum pulling with a single liquid <Developer>

PELEX NBL (sodium alkyl naphthalene sulfonate, anionic surfactant manufactured by KAO Corporation): 7.8 parts by mass NEWCOL B13 (polyoxyethylene aryl ether, nonionic surfactant manufactured by Nippon Nyukazai Co., Ltd): 2.00 parts by mass SURFYNOL 2502 (manufactured by Air Products and Chemicals, Lac.): 0.6 parts by mass Benzyl alcohol (manufactured by Wako Pure Chemical Corporation): 0.8 parts by mass Sodium gluconate (manufactured by Fuso Chemical Co., Ltd.): 3.0 parts by mass Sodium hydrogen phosphate (manufactured by Wako Pure Chemical Corporation), 0-3 parts by mass Sodium hydrogen carbonate (manufactured by Wako Pure Chemical Corporation): 0.3 parts by mass Defoamer (SILCOLAPSE 432 manufactured by Bluester Silicones): 0.01 parts by mass
Water 85.49 parts by mass (pH: 8.6)
[Printing]

The developed lithographic printing plates were attached to the plate trunk of a printer LITHRONE 26 manufactured by Komori Corporation. Dampening water and ink were supplied using dampening water of ECOLTTY-2 (manufactured by Fujifilm Corporation)/tap water=2/98 (capacity ratio) and Values-G(N) BLACK INK (manufactured by DIC Graphics Corporation) and using the standard automatic printing start method of LITHRONE 26, and then printing was carried out on TOKUBISHI art paper (76.5 kg) (manufactured by Mitsubishi Paper Mills limited) at a printing rate of 10,000 pieces per hour. As the number of printed pieces increased, the image-recording layer gradually wore, and thus the ink concentration on printed matters decreased. The number of pieces of printed paper until the value of the halftone dot area ratio of FM screen 50% halftone dots on printed matters measured using a gretag density meter decreased to be 5% lower than the measurement value obtained in a case in which pruning was carried out on a $100^{th}$ piece of paper was measured. The printing resistance was evaluated using relative printing resistance for which the number of pieces of printed paper of 50,000 was considered as 100 as shown in the following expression. A larger numerical value indicates superior printing resistance.

Relative printing resntance=(the number of pieces of printed paper of the subject lithographic printing plate precursor)/50,000×100

<Thermal and Temporal Stability (3)>

The lithographic printing plate precursor was adjusted in humidity in an environment of 25° C. and 60% for one hour and then packed. Neat, the packed matter was thermally aged at 60° C. far five days. After the end of the thermal aging, in the same manner as in the evaluation of the printing resistance, image exposure and a development process were carried out, and the concentration in a non-exposed portion after the development process was measured Regarding the measurement of the concentration, the cyan concentration was measured using a spectrophotometer (SpectroEye manufactured by X-Rite. Incorporated). The difference (ΔD) between the obtained value of the cyan concentration and the value of the cyan concentration of the support Eon which the application was not carried out was computed, and the thermal and temporal stability was evaluated as A to C. As AD decreases, the area of the image-recording layer remaining in the non-image area after the development process becomes smaller, and the thermal and temporal stability is more favorable.

| | Specific compound | Thermal and temporal stability (3) | Printing resistance |
|---|---|---|---|
| Example 501 | I-1-j-1 | A | 77 |
| Example 502 | I-5-j-1 | A | 79 |
| Example 503 | I-7-j-1 | A | 77 |
| Example 504 | I-12-j-1 | A | 82 |
| Example 505 | I-16-j-1 | A | 82 |
| Comparative Example 501 | H-1 | C | 67 |
| Comparative Example 502 | H-2 | B | 60 |

A: ΔD ≤ 0.01
B: 0.01 < ΔD ≤ 0.03
C: 0.03 < ΔD

In Table 5, I-1-j-1, I-5-j-1, I-7-j-1, I-12-j-1, I-16-j-1 shown in the column of "specific compound" indicate the specific compound of the present invention, and the structures thereof are as illustrated above. In addition, H-1 and H-2 are well-known compounds, and the structures thereof are as illustrated above.

From the results shown in Table 5, it is found that the lithographic printing plate precursors having the image-recording layer containing the specific compound according to the present invention are excellent in terms of all of the thermal and temporal stability (3) and the printing resistance.

According to the present invention, it is possible to provide a curable composition that can be used to produce lithographic printing plate precursors having excellent on-machine developability.

In addition, according to the present invention, it is possible to provide a curable composition having favorable thermal and temporal stability.

In addition, according to the present invention, it is possible to provide a lithographic printing plate precursor which has favorable thermal and temporal stability, is excellent in terms of on-machine developability, and can be used to produce lithographic printing plates having excellent printing resistance.

Furthermore, according to the present invention, it is possible to provide a lithographic printing plate precursor which has favorable thermal and temporal stability, is excellent in teams of a plate inspection property and on-machine developability, and can be used to produce lithographic printing plates having excellent printing resistance.

Furthermore, according to the present invention, it is possible to protide a lithographic printing plate precursor which has favorable thermal and temporal stability and can be used to produce lithographic printing plates having excellent printing resistance.

Furthermore, according to the present invention, it is possible to provide a method for producing a lithographic printing plate using the lithographic printing plate precursor and a compound that is used in an image-recording layer in the lithographic printing plate precursor. The present invention has been described in detail with reference to specific embodiments, but it is evident to a person dolled in the art that a variety of modifications or corrections can be added within the scope of the concept and scope of the present invention.

What is claimed is:
1. A lithographic printing plate precursor comprising:
  an image-recording layer containing a curable composition for a lithographic printing plate comprising:
  a salt compound having
    (A) an organic anion which is any one of the following organic anions I-2, I-4 to I-7, I-9 to I-10, and I-12 to I-26 or is an organic anion represented by the following General Formula (IV), and
    (B) a counter cation;
  an infrared absorber; and
  a polymerizable compound,

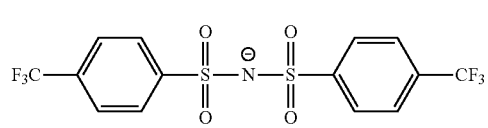

I-2

I-4
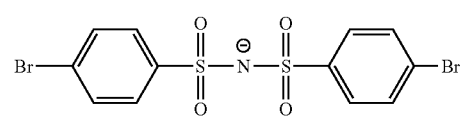
I-5
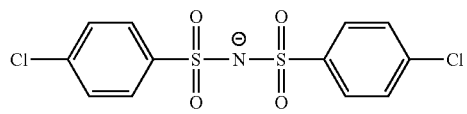
I-6
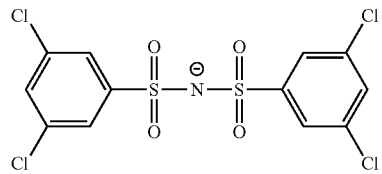
I-7
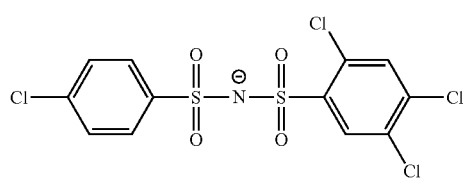
I-9
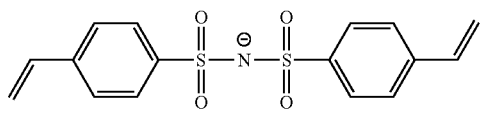
I-10
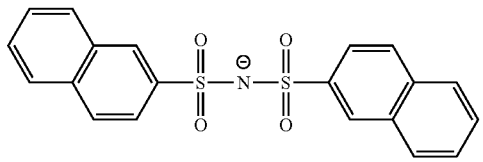
I-12
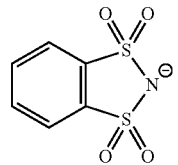
I-13
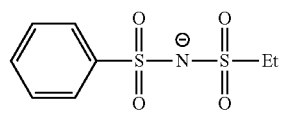
I-14
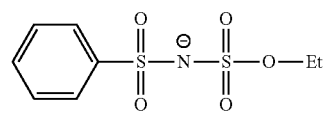
I-15
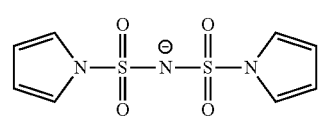
I-16
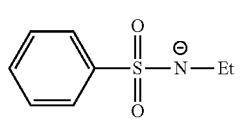
I-17
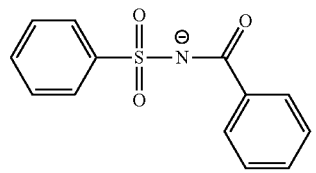
I-18
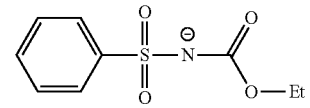
I-19
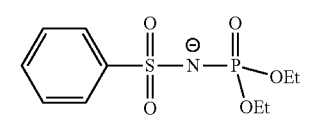
I-20
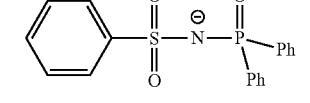
I-21
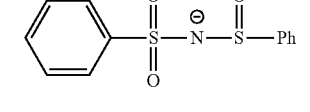
I-22
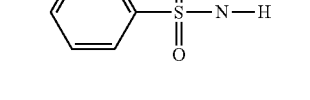
I-23
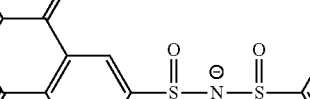
I-24
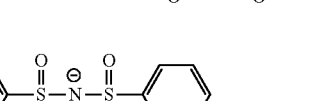
I-25
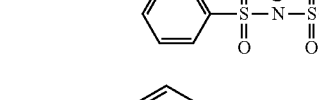
I-26
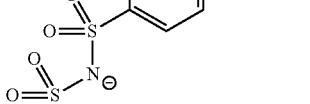
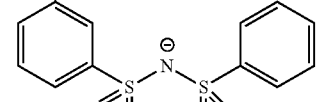

-continued
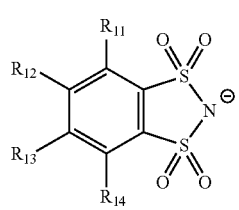
(IV)
in General Formula (IV), $R_{11}$ to $R_{14}$ each independently represents a hydrogen atom or a monovalent substituent.
* * * * *